United States Patent
Gonzalez et al.

(10) Patent No.: US 12,403,235 B2
(45) Date of Patent: *Sep. 2, 2025

(54) WOUND THERAPY SYSTEM WITH INTERNAL ALTERNATING ORIFICE

(71) Applicant: Solventum Intellectual Properties Company, Maplewood, MN (US)

(72) Inventors: Javier Gonzalez, San Antonio, TX (US); Shannon C. Ingram, Bulverde, TX (US)

(73) Assignee: Solventum Intellectual Properties Company, Maplewood, MN (US)

( * ) Notice: Subject to any disclaimer, the term of this patent is extended or adjusted under 35 U.S.C. 154(b) by 301 days.

This patent is subject to a terminal disclaimer.

(21) Appl. No.: 17/957,739

(22) Filed: Sep. 30, 2022

(65) Prior Publication Data
US 2023/0016336 A1   Jan. 19, 2023

Related U.S. Application Data

(62) Division of application No. 16/363,928, filed on Mar. 25, 2019, now Pat. No. 11,491,054.
(Continued)

(51) Int. Cl.
*A61M 1/00* (2006.01)
*A61B 5/00* (2006.01)
(Continued)

(52) U.S. Cl.
CPC .............. *A61M 1/742* (2021.05); *A61B 5/445* (2013.01); *A61F 13/05* (2024.01); *A61M 1/71* (2021.05);
(Continued)

(58) Field of Classification Search
CPC .... A61M 1/0023; A61M 1/0058; A61M 1/73; A61M 1/742; A61M 1/85; A61M 1/962;
(Continued)

(56) References Cited

U.S. PATENT DOCUMENTS 1,355,846 A   10/1920   Rannells
2,547,758 A    4/1951   Keeling
(Continued)

FOREIGN PATENT DOCUMENTS

AU   550575 B2   3/1986
AU   745271 B2   3/2002
(Continued)

OTHER PUBLICATIONS

Japanese Office Action for corresponding application 2021-545678, dated Jan. 31, 2023.
(Continued)

*Primary Examiner* — Kai H Weng

(57) ABSTRACT

A wound therapy system includes a dressing sealable over a wound and defining a wound space between the dressing and the wound, tubing fluidly communicable with the wound space, and a canister fluidly communicable with the tubing. The canister, the tubing, and the dressing define a sealed space that includes the wound space. The wound therapy system also includes a therapy unit coupled to the canister. The therapy unit includes a sensor configured to measure a pressure in the sealed space, a valve positioned between the sealed space and a surrounding environment and controllable between an open position and a closed position, and a control circuit. The control circuit is configured to control the valve to alternate between the open position and the closed position to allow airflow through the valve, receive measurements from the sensor, and determine a volume of the wound space based on the measurements.

12 Claims, 25 Drawing Sheets

Related U.S. Application Data

(60) Provisional application No. 62/802,034, filed on Feb. 6, 2019.

(51) Int. Cl.
*A61F 13/05* (2024.01)
*A61M 3/02* (2006.01)
*A61F 13/00* (2006.01)
*A61F 13/84* (2006.01)
*A61M 35/00* (2006.01)

(52) U.S. Cl.
CPC .............. *A61M 1/77* (2021.05); *A61M 1/777* (2021.05); *A61M 1/90* (2021.05); *A61M 1/92* (2021.05); *A61M 1/96* (2021.05); *A61M 1/962* (2021.05); *A61M 3/0258* (2013.01); *A61F 2013/00174* (2013.01); *A61F 2013/8494* (2013.01); *A61M 1/73* (2021.05); *A61M 1/74* (2021.05); *A61M 1/964* (2021.05); *A61M 1/966* (2021.05); *A61M 3/0202* (2021.05); *A61M 35/006* (2013.01); *A61M 2205/3337* (2013.01); *A61M 2205/3344* (2013.01)

(58) Field of Classification Search
CPC .......... A61M 1/964; A61M 2205/3334; A61M 2205/3337; A61M 2205/3344; A61M 2205/52; A61M 3/022; A61M 3/0258; A61M 35/006; A61F 13/0216; A61F 2013/00174; A61F 2013/8494; A61B 5/1073; A61B 5/445
See application file for complete search history.

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 7,846,141 B2 | 12/2010 | Weston |
| 8,062,273 B2 | 11/2011 | Weston |
| 8,216,198 B2 | 7/2012 | Heagle et al. |
| 8,251,979 B2 | 8/2012 | Malhi |
| 8,257,327 B2 | 9/2012 | Blott et al. |
| 8,398,614 B2 | 3/2013 | Blott et al. |
| 8,449,509 B2 | 5/2013 | Weston |
| 8,529,548 B2 | 9/2013 | Blott et al. |
| 8,535,296 B2 | 9/2013 | Blott et al. |
| 8,551,060 B2 | 10/2013 | Schuessler et al. |
| 8,568,386 B2 | 10/2013 | Malhi |
| 8,679,081 B2 | 3/2014 | Heagle et al. |
| 8,834,451 B2 | 9/2014 | Blott et al. |
| 8,926,592 B2 | 1/2015 | Blott et al. |
| 9,017,302 B2 | 4/2015 | Vitaris et al. |
| 9,198,801 B2 | 12/2015 | Weston |
| 9,211,365 B2 | 12/2015 | Weston |
| 9,289,542 B2 | 3/2016 | Blott et al. |
| 2002/0077661 A1 | 6/2002 | Saadat |
| 2002/0115951 A1 | 8/2002 | Norstrem et al. |

(56) References Cited

U.S. PATENT DOCUMENTS

| | | |
|---|---|---|
| 2002/0120185 A1 | 8/2002 | Johnson |
| 2002/0143286 A1 | 10/2002 | Tumey |
| 2014/0163491 A1 | 6/2014 | Schuessler et al. |
| 2015/0080788 A1 | 3/2015 | Blott et al. |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |
| GB | 2195255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/20041 A1 | 9/1994 |
| WO | 96/05873 A1 | 2/1996 |
| WO | 97/18007 A1 | 5/1997 |
| WO | 99/13793 A1 | 3/1999 |
| WO | 2008036360 A2 | 3/2008 |
| WO | 2017011204 A1 | 1/2017 |
| WO | 2019023311 A1 | 1/2019 |

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.
Susan Mendez-Eatmen, RN; "When wounds Won't Heal" RN Jan. 1998, vol. 61 (1); Medical Economics Company, Inc., Montvale, NJ, USA; pp. 20-24.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; Nov. 23, 1995.
PCT International Search Report for PCT International Application PCT/GB98/02713; Jan. 8, 1999.
PCT Written Opinion; PCT International Application PCT/GB98/02713; Jun. 8, 1999.
PCT International Examination and Search Report, PCT International Application PCT/GB96/02802; Jan. 15, 1998 & Apr. 29, 1997.
PCT Written Opinion, PCT International Application PCT/GB96/02802; Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu.N., et al; "Active Wound Drainage", Vestnki Khirurgi, vol. 138, Issue 4, 1987, and 7 page English translation thereof.
Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, ?. Maksimovi?, ?. Radak, and P. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

(56) References Cited

OTHER PUBLICATIONS

C.E. Tennants, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians; Jul. 2007.
1 Japanese Notice of Rejection for corresponding application 2021-545678, dated Dec. 24, 2024.

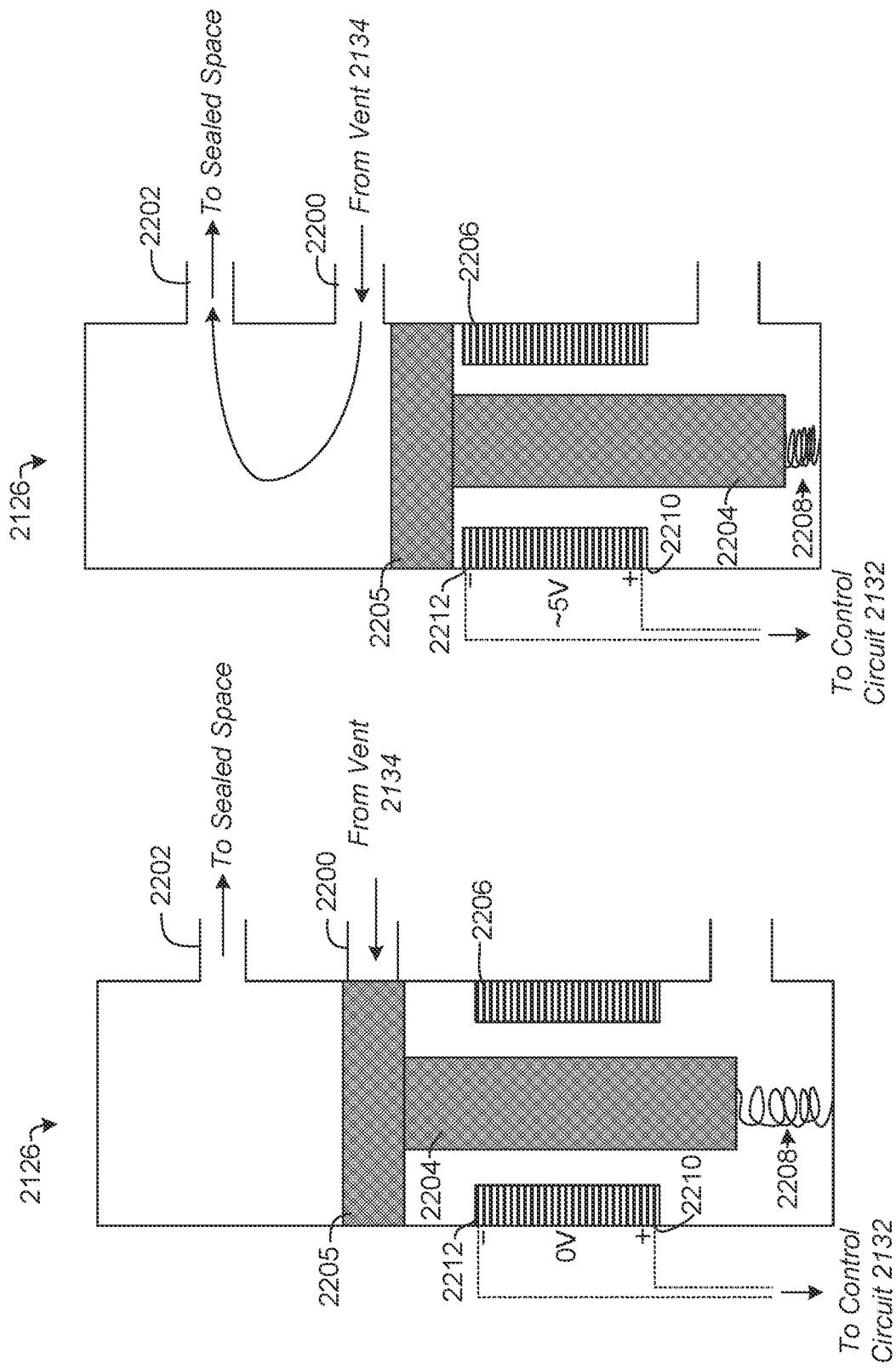

WOUND THERAPY SYSTEM WITH INTERNAL ALTERNATING ORIFICE

CROSS-REFERENCE TO RELATED APPLICATIONS

This application is a divisional of U.S. patent application Ser. No. 16/363,928, filed on Mar. 25, 2019, which claims the benefit of priority to U.S. Provisional Application No. 62/802,034, filed on Feb. 6, 2019, all of which are incorporated herein by reference in their entirety.

BACKGROUND

The present disclosure relates generally to a wound therapy system, and more particularly to a wound therapy system that provides negative pressure wound therapy (NPWT). NPWT refers to the creation of negative pressure (relative to atmospheric pressure) at a wound to promote healing of the wound. In a wound therapy system configured to provide NPWT, a dressing is typically sealed over a wound bed and placed in fluid communication with a pump operable to draw a negative pressure at the wound bed (i.e., in a wound space between the wound bed and the dressing). Because the dressing is sealed over the wound bed, often for a period of multiple days, it may be difficult to ascertain and monitor the progress of wound healing. One way to determine an amount of wound healing is based on a change in the amount of volume between the wound bed and the dressing (i.e., as the wound heals into the volume to occupy/consume part of the volume). Accordingly, systems and methods for volume determination in a wound therapy system may be advantageous.

In some cases, NPWT may be provided in coordination with instillation therapy and described as negative pressure and instillation wound therapy (NPIWT). Instillation therapy refers to the provision of instillation fluid (e.g., saline, antibiotic fluid) to the wound. One challenge in instillation therapy may be determining how much fluid to provide to the wound. It may be preferable to determine an amount of fluid to provide based on a size of the wound and/or a volume of available space adjacent the wound (i.e., between the dressing and the wound). Accordingly, systems and methods for volume determination in a wound therapy system may facilitate instillation therapy.

SUMMARY

One implementation of the present disclosure is a wound therapy system. The wound therapy system includes a dressing sealable over a wound and defining a wound space between the dressing and the wound, tubing coupled to the dressing and fluidly communicable with the wound space, and a canister fluidly communicable with the tubing. The canister, the tubing, and the dressing define a sealed space that includes the wound space. A therapy unit is coupled to the canister. The therapy unit includes a pneumatic pump fluidly communicable with the sealed space, a sensor configured to measure a pressure in the sealed space, a valve positioned between the sealed space and a surrounding environment and controllable between an open position and a closed position, and a control circuit. The control circuit is configured to control the pneumatic pump to remove air from the sealed space to establish a negative pressure in the sealed space, control the valve to repeatedly alternate between the open position and the closed position to allow a controlled rate of airflow through the valve, receive measurements of the pressure in the sealed space from the sensor, and determine a volume of the wound space based on the measurements of the pressure.

In some embodiments, the controlled rate of airflow is less than a restriction rate of a filter positioned between the valve and the canister.

In some embodiments, valve includes a solenoid valve. The control circuit is configured to control the valve to repeatedly alternate between the open position and the closed position by providing a voltage pattern to the solenoid valve. The voltage pattern includes a step function repeatedly stepping between approximately zero voltage and a non-zero voltage. The voltage pattern may remain at the non-zero voltage for no more than a maximum continuous duration of approximately 500 milliseconds.

In some embodiments, the voltage pattern includes a repeating pattern of approximately 400 milliseconds at a non-zero voltage, approximately 100 milliseconds at approximately zero voltage, approximately 400 milliseconds at the non-zero voltage, and approximately 100 milliseconds at approximately zero voltage. The voltage pattern includes a first set of two periods of the repeating pattern, approximately one second at approximately zero voltage, and a second set of two periods of the repeating pattern. The voltage pattern may cause the solenoid valve to alternate between the open position and the closed position with a period of approximately 500 milliseconds.

In some embodiments, the control circuit is further configured to customize a customized wound therapy based on the volume of the wound space and control the therapy unit to provide the customized wound therapy. The customized wound therapy may include instillation therapy.

In some embodiments, the control circuit is configured to customize the instillation therapy by determining an amount of instillation fluid to supply to the wound space based on the volume of the wound space. The wound therapy system may include instillation tubing coupled to the dressing and fluidly communicable with the wound space, a source of the instillation fluid fluidly communicable with the instillation tubing, and an instillation pump controllable by the control circuit to provide the amount of the instillation fluid from the source to the wound space.

Another implementation of the present disclosure is a method of treating a wound. The method includes establishing a sealed space defined by a dressing, tubing, and a canister of a wound therapy system. The sealed space includes a wound space defined by the dressing and the wound. The method includes removing, with a pneumatic pump, air from the sealed space to establish a negative pressure in the sealed space and causing a solenoid valve to alternate between an open position and a closed position. The solenoid valve allows an airflow from a surrounding environment to the sealed space in the open position and prevents the airflow from the surrounding environment to the sealed space in the closed position. The method also includes measuring the pressure in the sealed space to generate pressure measurements, determining, based on the pressure measurements, a volume of the wound space, customizing a customized wound therapy based on the volume of the wound space, and providing the customized wound therapy to the wound.

In some embodiments, customizing a customized wound therapy includes determining an amount of an instillation fluid to be supplied to the wound space based on the volume of the wound space. Providing the customized wound therapy to the wound includes controlling an installation pump to supply the amount of the installation fluid to the wound space.

In some embodiments, causing the solenoid valve to alternate between the open position and the closed position provides a controlled rate of airflow from the surrounding environment to the sealed space. The controlled rate of airflow is less than a restriction rate of a filter positioned between the canister and the solenoid valve.

In some embodiments, causing the solenoid valve to alternate between the open position and the closed position includes providing a voltage pattern to the solenoid valve. The voltage pattern may include a step function repeatedly stepping between approximately zero voltage and a non-zero voltage. The voltage pattern may include a repeating pattern of approximately 400 milliseconds at a non-zero voltage, approximately 100 milliseconds at approximately zero voltage, approximately 400 milliseconds at the non-zero voltage, and approximately 100 milliseconds at approximately zero voltage.

In some embodiments, the voltage pattern includes a first set of two periods of the repeating pattern, approximately one second at approximately zero voltage, and a second set of two periods of the repeating pattern. The non-zero voltage causes the solenoid valve to be in the open position. A positive pressure of approximately 5 mmHg is provided to the sealed space during each 400 milliseconds at the non-zero voltage.

Another implementation of the present disclosure is a wound therapy system. The wound therapy system includes a dressing sealable over a wound and defining a wound space between the dressing and the wound, first tubing coupled to the dressing and fluidly communicable with the wound space, a canister fluidly communicable with the first tubing, wherein the canister, the first tubing, and the dressing define a sealed space that includes the wound space, a pneumatic pump fluidly communicable with the sealed space, a sensor configured to measure a pressure in the sealed space, and a solenoid valve controllable between an open position and a closed position. The solenoid valve is configured to allow air to flow from a surrounding environment to the sealed space in the open position and prevent air from flowing from the surrounding environment to the sealed space in the closed position. The wound therapy system also includes installation tubing coupled to the dressing and fluidly communicable with the wound space and a source of installation fluid, an installation pump coupled to the installation tubing and controllable to supply an amount of the installation fluid to the wound space, and a control circuit. The control circuit is configured to control the pneumatic pump to remove air from the sealed space to establish a negative pressure in the sealed space and provide a voltage pattern to the solenoid valve. The voltage pattern causes the solenoid valve to repeatedly alternate between the open position and the closed position. The control circuit is also configured to receive measurements of the pressure from the sensor, determine a volume of the wound space based on the measurements of the pressure, determine the amount of the installation fluid based on the volume of the wound space, and control the installation pump to supply the amount of the installation fluid to the wound space.

In some embodiments, causing the solenoid valve to alternate between the open position and the closed position allows a controlled rate of airflow through the solenoid valve from the surrounding environment to the sealed space.

In some embodiments, the solenoid valve is positioned to allow the air to enter one or more outer lumens of the first tubing. In some embodiments, a filter is positioned between the solenoid valve and the one or more outer lumens. Causing the solenoid valve to alternate between the open position and the closed position allows a controlled rate of airflow through the solenoid valve from the surrounding environment to the channel, and the controlled rate is less than a restriction rate of the filter.

In some embodiments, the installation pump, the pneumatic pump, and the control circuit are housed within a therapy unit. In some embodiments, the solenoid valve is positioned within the therapy unit. In some embodiments, the solenoid valve is positioned outside the therapy unit and coupled to the first tubing.

Another implementation of the present disclosure is a therapy unit. The therapy unit includes a pneumatic pump fluidly communicable with a sealed space, a sensor configured to measure a pressure in the sealed space, a valve positioned between the sealed space and a surrounding environment and controllable between an open position and a closed position, and a control circuit. The control circuit is configured to control the pneumatic pump to remove air from the sealed space to establish a negative pressure in the sealed space, control the valve to repeatedly alternate between the open position and the closed position to allow a controlled rate of airflow through the valve, receive measurements of the pressure in the sealed space from the sensor, and determine a volume of the sealed space based on the measurements of the pressure and the controlled rate, and provide a customized wound therapy based on the volume of the sealed space.

In some embodiments, the control circuit is configured to allow the controlled rate of airflow through the valve by controlling the valve to the open position for no longer than a maximum continuous duration of approximately 500 milliseconds.

Another implementation of the present disclosure is a wound therapy system. The wound therapy system includes a pneumatic pump fluidly communicable with a canister and tubing comprising a first lumen and a second lumen. The first lumen is configured to facilitate the flow of fluid from a dressing to the canister and the second lumen configured to facilitate measurement of a pressure at the dressing. The wound therapy system also includes a sensor configured to measure a pressure in the second lumen, a valve positioned between a second lumen and a surrounding environment and controllable between an open position and a closed position, a filter positioned between the valve and the second lumen, and a cap removeably coupleable to the tubing. The cap provides fluid communication between the first lumen and the second lumen when the cap is coupled to the tubing. The wound therapy system also includes a control circuit configured to, while the cap is coupled to the tubing, operate the pump to remove air from the canister, control the valve to the open position, receive measurements of the pressure in the second lumen from the sensor, and determine, based on the measurements of the pressure in the second lumen, a flow rate through the filter.

In some embodiments, the control circuit is configured to, while the cap is removed from the tubing and the dressing is coupled to the tubing, determine a volume of a wound space based on the flow rate through the filter and additional measurements of the pressure from the sensor. In some embodiments, the control circuit is configured to provide a customized wound therapy based on the volume of the wound space.

BRIEF DESCRIPTION OF THE FIGURES

Various objects, aspects, features, and advantages of the disclosure will become more apparent and better understood by referring to the detailed description taken in conjunction with the accompanying drawings, in which like reference characters identify corresponding elements throughout. In the drawings, like reference numbers generally indicate identical, functionally similar, and/or structurally similar elements.

FIG. 19 is a cross-sectional illustration of a solenoid valve of the NPIWT system of FIG. 18 in a closed position, according to an exemplary embodiment.

FIG. 20 is a cross-sectional illustration of the solenoid valve of FIG. 19 in an open position, according to an exemplary embodiment.

DETAILED DESCRIPTION OF THE FIGURES

Overview

Figure 1:
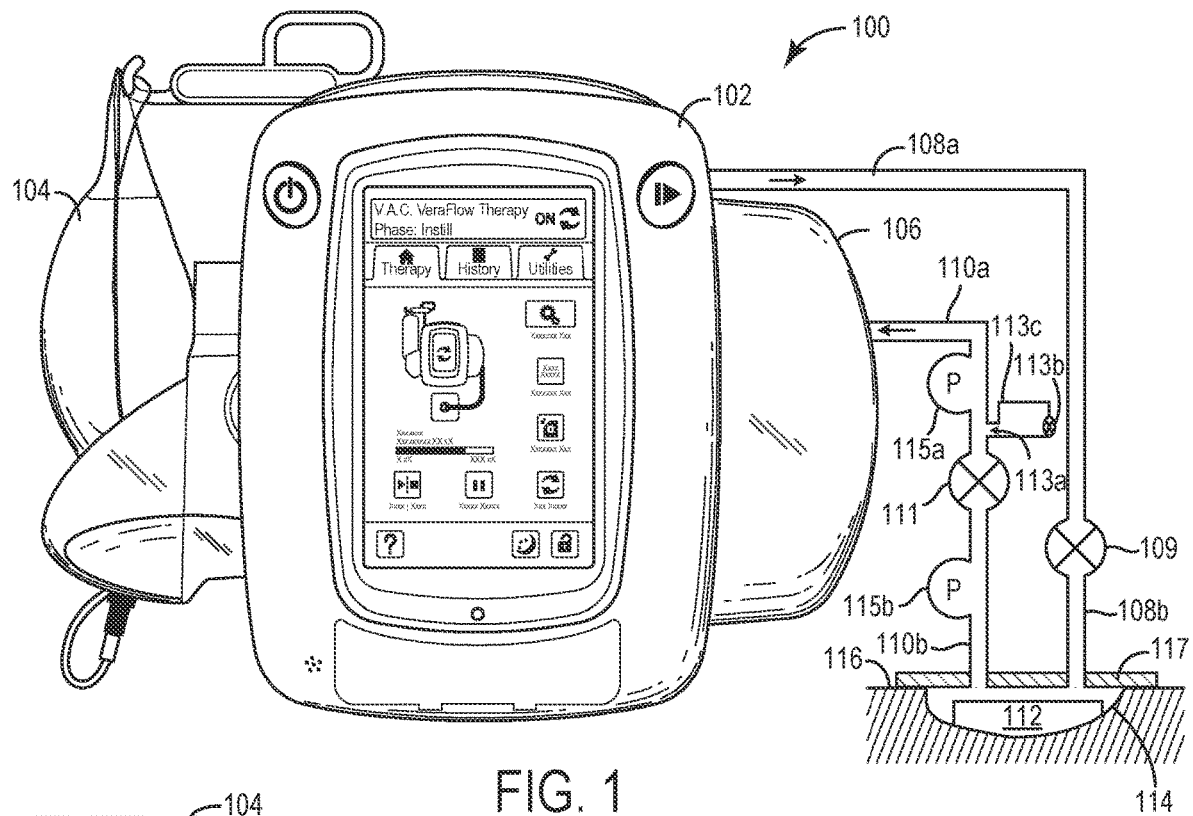
FIG. 1 is a partial block diagram of a negative pressure wound therapy system including a therapy device coupled to a wound dressing via tubing, according to an exemplary embodiment.

Referring generally to FIGS. 1-17, a wound therapy system is shown according to various exemplary embodiments. The wound therapy system may include a therapy device and a wound dressing. The therapy device may include an instillation fluid canister, a removed fluid canister, a valve, a pneumatic pump, an instillation pump, a tubeset module and a controller. The wound dressing can be applied to a patient's skin surrounding a wound. The therapy device can be configured to deliver instillation fluid to the wound and provide negative pressure wound therapy (NPWT) by maintaining the wound at negative pressure. Components of the wound therapy device, the wound dressing, and the wound site form a negative pressure circuit.

The controller can be configured to operate the pneumatic pump, the instillation pump, the tubeset module and/or other controllable components of the therapy device. In some embodiments, the controller estimates the volume of the wound based on a comparison of observed dynamic pressure responses to negative pressure being applied to the entirety of the negative pressure circuit and negative pressure being applied to a selected portion of the negative pressure circuit. Based on the comparison of the observed dynamic responses, the controller may be configured to determine a quantity of instillation fluid to be delivered to the wound site.

The tubeset module comprises one or more elements that are actuatable, controllable or which may otherwise be engaged by the controller, with the selective communication of the controller with the tubeset module being configured to allow the controller to, among other functions, effectuate and monitor various dynamic pressure responses in all of and/or in parts of the negative pressure circuit as needed to estimate the volume of the wound, determine a quantity of instillation fluid to be delivered to the wound site and/or perform any other number of functions that may be related to the use of the NPWT system 100.

According to some embodiments, the volume relative to the wound site determined by the controller may relate to the dead space at the wound site (i.e. the available space within a drape layer applied about the wound site into which instillation fluid may be delivered). In some such embodiments, the controller may be configured to determine a quantity of instillation fluid to be delivered to the wound site based on a predetermined percentage of the calculated dead space volume at the wound site (e.g., 20%, 50%, 80%, etc.). The controller can then operate the tubeset module and instillation pump to deliver the determined volume of instillation fluid to the wound. By basing the quantity of instillation fluid to be delivered to the wound site on a calculated volume of the dead space at the wound site, the negative pressure system may be configured to provide for more efficient and more precise delivery of instillation fluid, which may reduce the risk of leakage resulting from over-delivery of instillation fluid and the risk of ineffective wound site treatment resulting from under-delivery of instillation fluid.

In some embodiments, the controller may additionally, or alternatively, measure and monitor volumes relative to the wound site at a plurality of times during wound treatment, with the controller determining healing progression of the wound site based on changes in the measured volume relative to the wound site over the course of NPWT treatment. By monitoring the healing progression of the wound site, the controller may be configured to alert a user if the healing of the wound site is not progressing as intended or expected. These and other features of the wound therapy system are described in detail below.

Wound Therapy System

Referring now to FIG. 1, a negative pressure wound therapy (NPWT) system 100 is shown according to an exemplary embodiment. NPWT system 100 is shown to include a therapy device 102 fluidly connected to a wound dressing 112 via tubing 108 and 110. As will be described in more detail below, according to various embodiments a tubeset module 300 may be operably connected to the tubing 108 and/or 110.

According to various embodiments, a wound dressing 112 may be placed on or within the wound site 114 and adhered or sealed to a patient's skin 116 surrounding a wound site 114 using drape layer 117. Several examples of wound dressings 112 which can be used in combination with NPWT system 100 are described in detail in U.S. Pat. No. 7,651,484 granted Jan. 26, 2010, U.S. Pat. No. 8,394,081 granted Mar. 12, 2013, and U.S. patent application No. 14/087,418 filed Nov. 22, 2013. The entire disclosure of each of these patents and patent applications is incorporated by reference herein.

Figure 2:
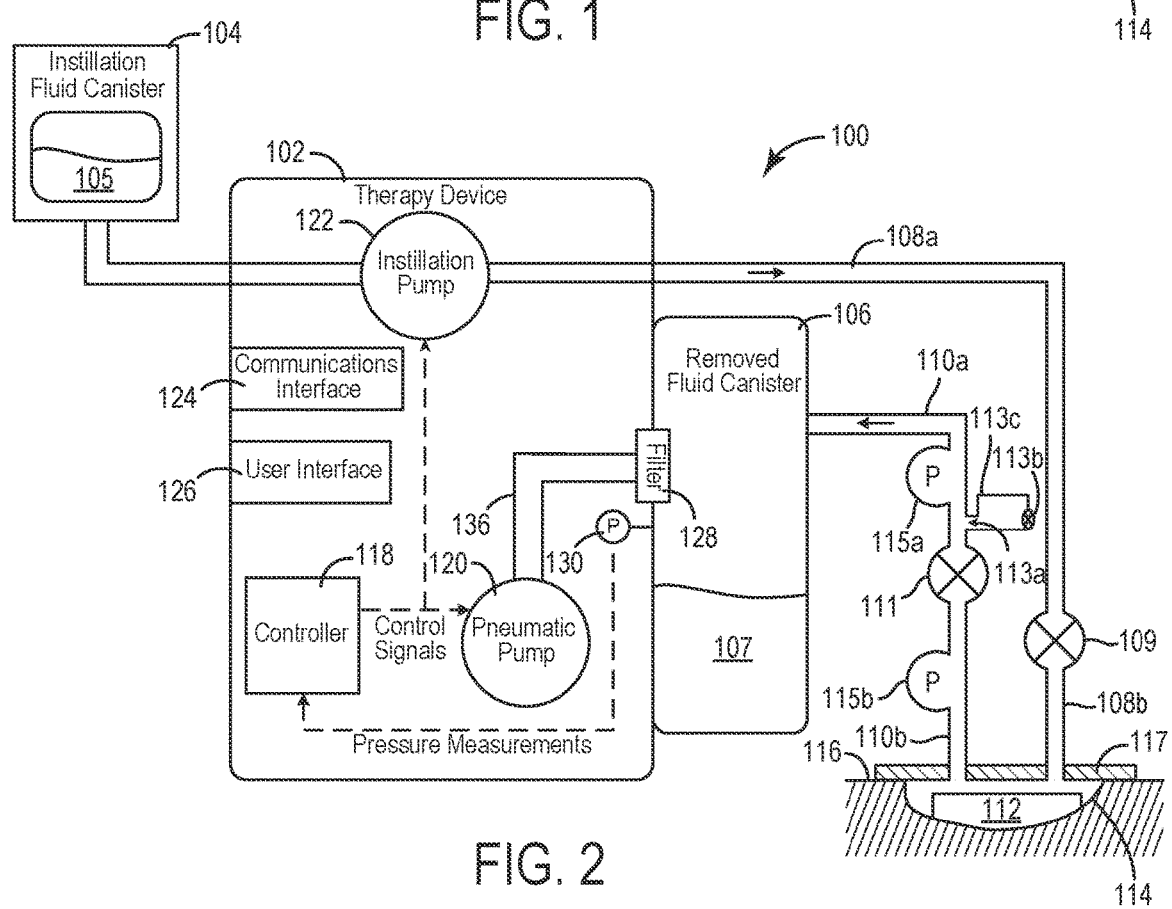
FIG. 2 is a block diagram illustrating the negative pressure wound therapy system of FIG. 1 in greater detail, according to an exemplary embodiment.

As illustrated by the block diagram of FIG. 2, in general the therapy device 102 includes a pneumatic pump 120, an instillation pump 122, a filter 128, and a controller 118. Pneumatic pump 120 can be fluidly coupled to removed fluid canister 106 (e.g., via conduit 136) and can be configured to draw a vacuum within removed fluid canister 106 by pumping air out of removed fluid canister 106. In some embodiments, pneumatic pump 120 is configured to operate in both a forward direction and a reverse direction. For example, pneumatic pump 120 can operate in the forward direction to pump air out of removed fluid canister 106 and decrease the pressure within removed fluid canister 106. Pneumatic pump 120 can operate in the reverse direction to pump air into removed fluid canister 106 and increase the pressure within removed fluid canister 106. Pneumatic pump 120 can be controlled by controller 118, described in greater detail below.

Therapy device 102 can be configured to provide negative pressure wound therapy by reducing the pressure at wound site 114. Therapy device 102 can draw a vacuum at wound site 114 (relative to atmospheric pressure) by removing wound exudate, air, and other fluids from wound site 114. Wound exudate may include fluid that filters from a patient's circulatory system into lesions or areas of inflammation. For example, wound exudate may include water and dissolved solutes such as blood, plasma proteins, white blood cells, platelets, and red blood cells. Other fluids 121 removed from wound site 114 may include instillation fluid 105 previously delivered to wound site 114. Instillation fluid 105 can include, for example, a cleansing fluid, a prescribed fluid, a medicated fluid, an antibiotic fluid, or any other type of fluid which can be delivered to wound site 114 during wound treatment. Instillation fluid 105 may be held in an instillation fluid canister 104 and controllably dispensed to wound site 114 via tubing 108. In some embodiments, instillation fluid canister 104 is detachable from therapy device 102 to allow removed fluid canister 106 to be refilled and replaced as needed.

Instillation pump 122 can be fluidly coupled to instillation fluid canister 104 via upstream instillation tubing 108a and fluidly coupled to wound dressing 112 via downstream instillation tubing 108b. Instillation pump 122 can be operated to deliver instillation fluid 105 to wound dressing 112 and wound site 114 by pumping instillation fluid 105 through upstream instillation tubing 108a and downstream instillation tubing 108b. Instillation pump 122 can be controlled by controller 118, described in greater detail below. According to some embodiments, an instillation tubing valve 109 valve configured to allow for flow only in the direction from the instillation fluid canister 104 to the wound site 114 (e.g. via a one-way valve or a via valve configured to be selectively switched by a user and/or by the controller 118 to a closed position prior to the application of negative pressure to the wound site 114) may generally be provided at a location along a portion of the downstream instillation tubing 108b. As will be described in more detail below, according to various embodiments, the instillation tubing valve 109 may be provided as part of the tubeset module 300.

Filter 128 can be positioned between removed fluid canister 106 and pneumatic pump 120 (e.g., along conduit 136) such that the air pumped out of removed fluid canister 106 passes through filter 128. Filter 128 can be configured to prevent liquid or solid particles from entering conduit 136 and reaching pneumatic pump 120. Filter 128 may include, for example, a bacterial filter that is hydrophobic and/or lipophilic such that aqueous and/or oily liquids will bead on the surface of filter 128. Pneumatic pump 120 can be configured to provide sufficient airflow through filter 128 that the pressure drop across filter 128 is not substantial (e.g., such that the pressure drop will not substantially interfere with the application of negative pressure to wound site 114 from therapy device 102).

Removed fluid canister 106 may be a component of therapy device 102 configured to collect wound exudate and other fluids 121 removed from wound site 114. In some embodiments, removed fluid canister 106 is detachable from therapy device 102 to allow removed fluid canister 106 to be emptied and replaced as needed. A lower portion of removed fluid canister 106 may be filled with wound exudate and other fluids 107 removed from wound site 114, whereas an upper portion of removed fluid canister 106 may be filled with air. Therapy device 102 can be configured to draw a vacuum within removed fluid canister 106 by pumping air out of removed fluid canister 106. The reduced pressure within removed fluid canister 106 can be translated to wound dressing 112 and wound site 114 via tubing 110.

As shown in FIG. 1, disposed along tubing 110 at a location between the removed fluid canister 106 and the wound site 114 is a tubing valve 111 configured to selectively permit and prevent fluid flow between the removed fluid canister 106 and the wound site 114. The tubing valve 111 may be defined by any number of different structures (e.g. spring-biased; duck-bill; clamp; check-valve, etc.) configured to allow for the selective control of fluids through the tubing 110, and may include valves that are configured to be selectively opened and/or closed by a user, in response to a sensed stimulus (e.g. a predetermined threshold pressure), or by the controller 118. As will be described in more detail below, according to various embodiments, the tubing valve 111 may be provided as part of the tubeset module 300.

Figure 3:
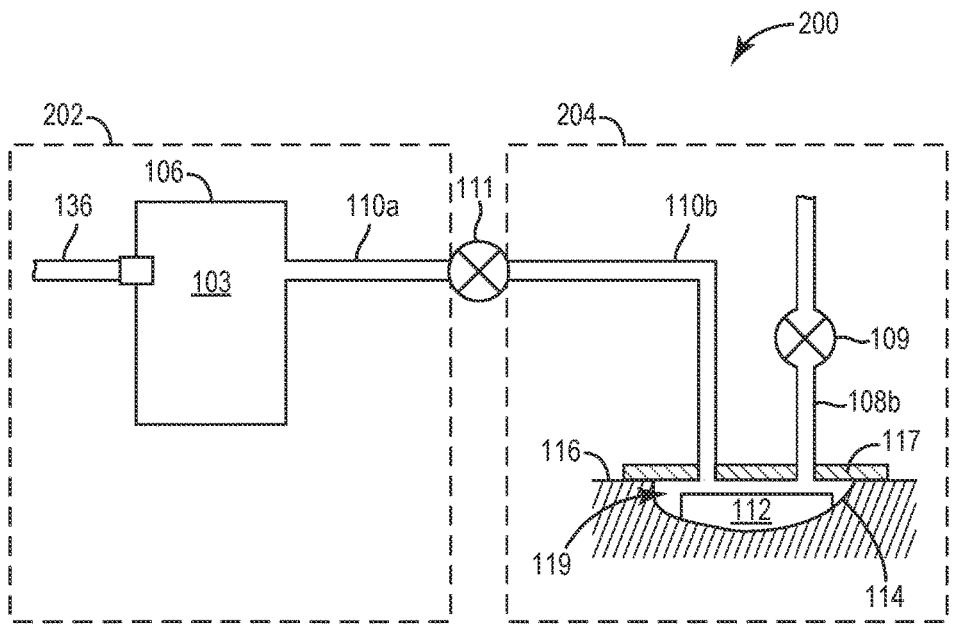
FIG. 3 is a block diagram illustrating the negative pressure circuit, the removed fluid canister circuit and the wound site circuit of the negative pressure wound therapy system of FIG. 1 in greater detail, according to an exemplary embodiment.

Referring to the block diagram of FIG. 3, when the tubing valve 111 is in an open, flow configuration, removed fluid canister 106, tubing 110 (i.e. both upstream tubing portion 110a and downstream tubing portion 110b), conduit 136 extending between pneumatic pump 120 and removed fluid canister 106, the portion of downstream instillation tubing 108b extending between the drape layer 117 and instillation tubing valve 109, and wound site 114 are fluidly connected to define a negative pressure circuit 200. Referring further to FIG. 3, when the tubing valve 111 is in a closed, no-flow configuration, the removed fluid canister 106, conduit 136 and an upstream tubing portion 110a of the tubing 110 extending between the removed fluid canister 106 and the tubing valve 111 define a removed fluid canister circuit 202 that is fluidly isolated from a wound site circuit 204 defined by the wound site 114, a downstream tubing portion 110b of tubing 110 extending between the tubing valve 111, a portion of downstream instillation tubing 108b extending between the drape layer 117 and instillation tubing valve 109, and the wound site 114. As will be discussed in more detail below, the volumes of the tubing 110, conduit 136, and portion of downstream instillation tubing 108b extending between the drape layer 117 and instillation tubing valve 109 define known volumes which can be easily subtracted from or otherwise factored into calculations of volume(s) relative to the wound site 114.

Referring again to FIG. 1, according to some embodiments, also provided along and operably fluidly connected to tubing 110 at a location upstream of tubing valve 111 and downstream of removed fluid canister 106 is a calibrated leak system 113 defined by a vent 113a formed through an outer wall of the tubing 110, the vent 113a being selectively closeable by a vent valve 113b. Also forming a part of calibrated leak system 113 may be a flow detector 113c configured to measure airflow through the vent 113a. As will be described in more detail below, calibrated leak system 113 is configured to selectively control and measure airflow between tubing 110 and the ambient environment surrounding therapy device 102. According to various embodiments, calibrated leak system 113 can be selectively opened to allow airflow into tubing 110 at a known, predetermined rate. As will be described in more detail below, according to various embodiments, calibrated leak system 113 may be provided as part of the tubeset module 300.

As will be described in more detail below, when both the vent valve 113b and the tubing valve 111 are closed, operation of the pneumatic pump 120 may be configured to draw a vacuum in only the removed fluid canister circuit 202 portion of the negative pressure circuit 200 (such as, e.g., illustrated in FIG. 6E). When the vent valve 113b is closed and the tubing valve 111 is open, operation of the pneumatic pump 120 may be configured to draw a vacuum in the entirety of the negative pressure circuit 200 (such as, e.g., illustrated in FIG. 6C). When the vent valve 113b is open and the tubing valve 111 is closed, airflow from the environment around therapy device 102 may enter through the vent 113a of the calibrated leak system 113 and fill the vacuum within the removed fluid canister circuit 202 (such as, e.g., illustrated in FIG. 6F). As illustrated, e.g., by FIG. 6D, when both the vent valve 113b and the tubing valve 111 are open, airflow from the environment around therapy device 102 may enter through the vent 113a of the calibrated leak system 113 and fill the vacuum within the entirety of the negative pressure circuit 200. As will be understood, according to various embodiments, the opening and/or closing of the vent valve 113b and/or tubing valve 111 may be effectuated manually or automatically, e.g., using tubeset module 300.

Figure 4:
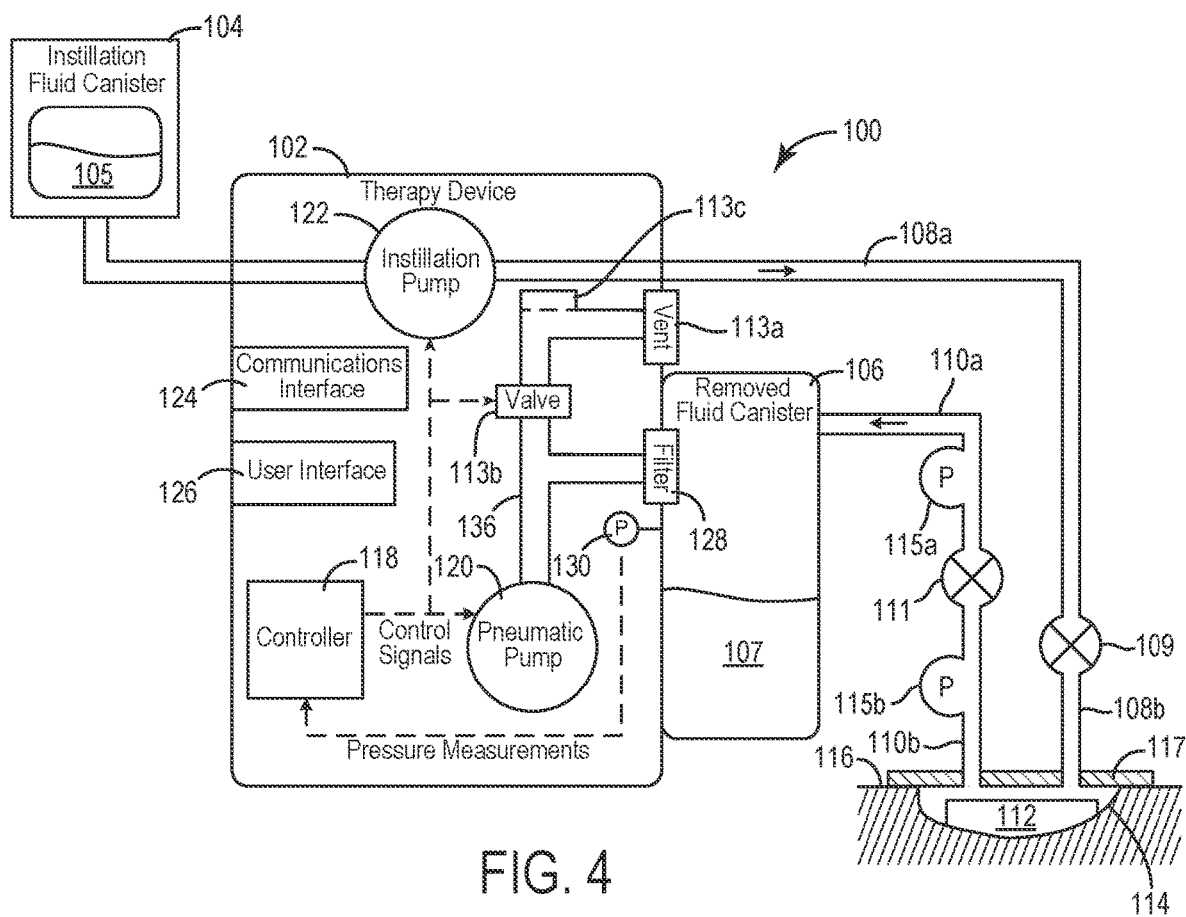
FIG. 4. is a block diagram illustrating a negative pressure wound therapy system, according to an exemplary embodiment.

Although the calibrated leak system 113 has been disclosed as being positioned in-line with a portion of the tubing 110 extending between the wound site 114 and the removed fluid canister 106, according to some embodiments, such as, e.g., illustrated in FIG. 4, the calibrated leak system 113 may be instead formed in-line with conduit 136. The operation of the calibrated leak system 113 of the embodiment of FIG. 4 is similar to the operation of the calibrated leak system 113 illustrated in FIG. 1, with the calibrated leak system 113 of FIG. 4 being configured to provide a path through which air from the ambient environment may flow into and fill portions or the entirety of the negative pressure circuit 200 following the creation of a vacuum within a portion or entirety of the negative pressure circuit 200. As will be understood, according to various embodiments, any of the methods or systems illustrated or disclosed herein which incorporate a calibrated leak system 113 embodiment as illustrated in FIG. 1 may be modified with a calibrated leak system 113 embodiment as illustrated in FIG. 4.

As illustrated by the block diagram of FIG. 2, according to various embodiments, the controller 118 may be configured to operate various components of therapy device 102. In particular, as will be described in more detail below, according to various embodiments, the controller 118 may be configured to control the various components of the NPWT system 100 to execute one or more volume determination procedures via which, e.g., a quantity of instillation fluid 105 to be delivered to the wound site 114 may be determine, the healing progression of the wound site 114 may be tracked, etc. According to various embodiments, the controller 118 may be configured such that these procedures may be performed with minimal user intervention and/or input.

According to various embodiments, therapy device 102 may include a variety of sensors. For example, in some embodiments, therapy device 102 may include pressure sensor 115a and/or 115b located in-line in the upstream tubing portion 110a and/or downstream tubing portion 110b, which are configured to measure pressure at the removed fluid canister 106 and/or wound site 114. Pressure measurements recorded by pressure sensor(s) 115a and/or 115b can be communicated to controller 118. According to various embodiments, controller 118 may use the pressure measurements from pressure sensor(s) 115a and/or 115b as inputs to various pressure testing operations and control operations performed by controller 118. As will be described in more detail below, according to various embodiments, the pressure sensor(s) 115a and/or 115b may be provided as part of the tubeset module 300.

In some embodiments, therapy device 102 includes a user interface 126. User interface 126 may include one or more buttons, dials, sliders, keys, or other input devices configured to receive input from a user. User interface 126 may also include one or more display devices (e.g., LEDs, LCD displays, etc.), speakers, tactile feedback devices, or other output devices configured to provide information to a user. User interface 126 can also display alerts generated by controller 118. For example, controller 118 can generate a "no canister" alert if removed fluid canister 106 is not detected.

In some embodiments, therapy device 102 includes a data communications interface 124 (e.g., a USB port, a wireless transceiver, etc.) configured to receive and transmit data. Communications interface 124 may include wired or wireless communications interfaces (e.g., jacks, antennas, transmitters, receivers, transceivers, wire terminals, etc.) for conducting data communications external systems or devices. In various embodiments, the communications may be direct (e.g., local wired or wireless communications) or via a communications network (e.g., a WAN, the Internet, a cellular network, etc.). For example, communications interface 124 can include a USB port or an Ethernet card and port for sending and receiving data via an Ethernet-based communications link or network. In another example, communications interface 124 can include a Wi-Fi transceiver for communicating via a wireless communications network or cellular or mobile phone communications transceivers.

Methods of Use

Figure 5:
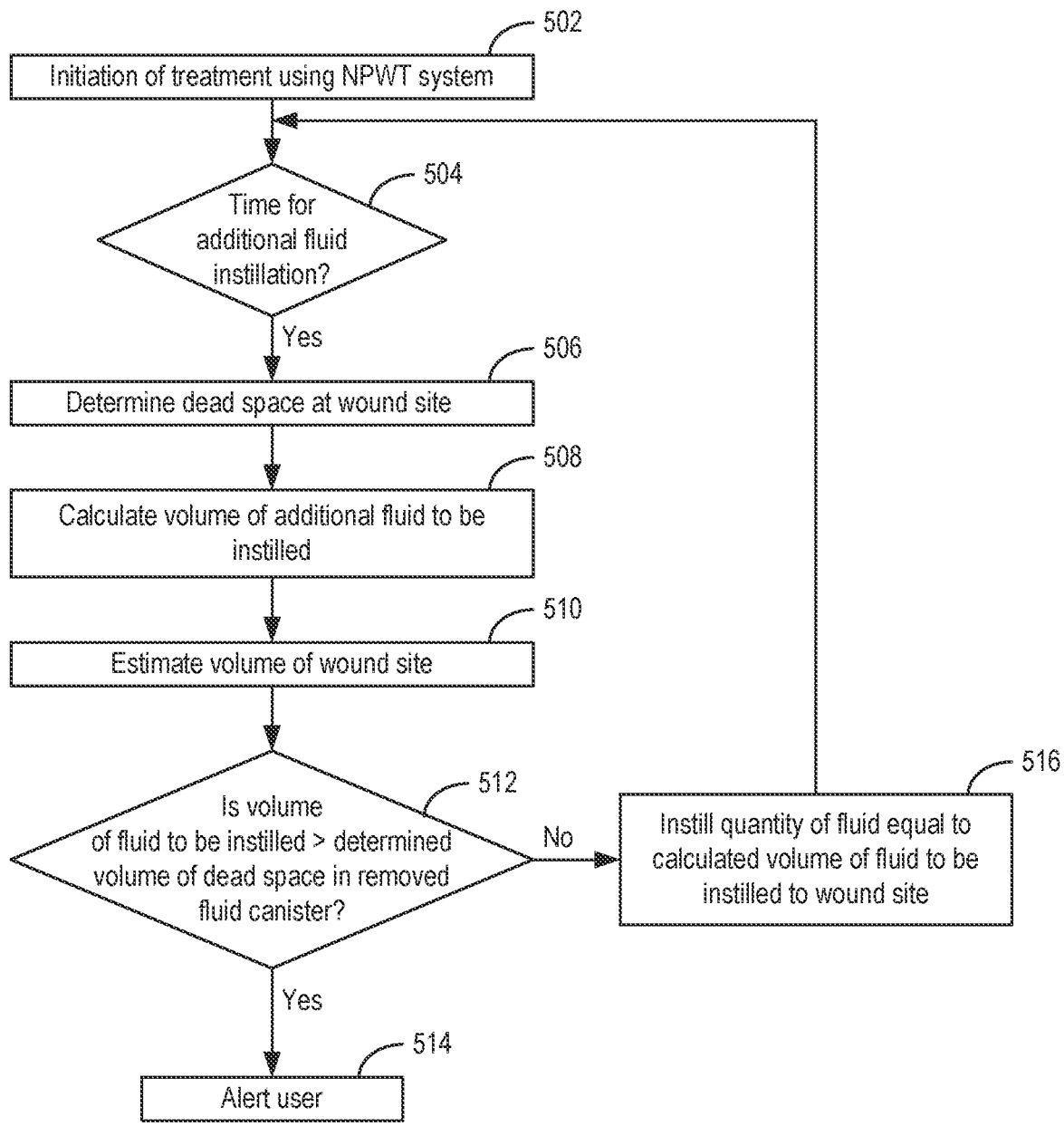
FIG. 5 is a flowchart of a method of using a negative pressure wound therapy system, according to an exemplary embodiment.

Referring to FIG. 5, a flowchart of a method 500 of using NPWT system 100 according to an exemplary embodiment is shown. As will be discussed in more detail with reference to FIGS. 6A-6G, initial set up of the NPWT system 100 and a delivery of an initial amount of instillation fluid 105 to a wound site 114 being treated by the NPWT system 100 occurs at step 502.

As shown at step 504, according to various embodiments, it may be desirable to deliver additional instillation fluid 105 to the wound site 114 following the instillation of an initial amount of instillation fluid 105 to the wound site 114. As will be understood, the determination at step 504 of when and if additional instillation fluid 105 is to be delivered to the wound site 114 may be based on any number of various factors, including e.g. elapsed time from a prior instillation; type of wound site 114; desired course of wound site 114 treatment; sensed conditions related to the wound site 114, etc., and may be decided automatically by the controller 118, or may be based on user input.

If it is determined at step 504 that additional fluid is to be delivered, at step 506 the dead space 119 at the wound site 114 is determined according to any of the methods as will be described below. According to various embodiments (described in more detail below), at step 506, the controller 118 may be configured to determine the dead space 103 at the wound site 114 prior to such delivery of additional instillation fluid 105, irrespective of: whether the quantity of instillation fluid 105 previously instilled to the wound site 114 is known; the presence of non-absorbed instillation fluid 105 and/or wound exudate in the space defined between the wound site 114 and the drape layer 117; whether the volume of any contents 107 in the removed fluid canister 106, the volume of the removed fluid canister 106 itself, and/or the volume of any contents 107 previously emptied from the removed fluid canister 106 are known; whether the removed fluid canister 106 has been replaced with a different-sized removed fluid canister 106 during the course of the NPWT treatment; changes to the shape/size/volume of the wound site 114; etc.

At step 508, the quantity of additional instillation fluid 105 to be delivered to the wound site 114 is calculated. According to various embodiments, the quantity of additional instillation fluid 105 delivered to the wound site 114 may be based on the volume of the dead space determined at step 506. For example, in some embodiments, the controller 118 may calculate the volume of instillation fluid 105 to be delivered to wound site 114 by multiplying the volume if dead space determined at step 506 by a fluid instillation factor. The fluid instillation factor may be equal to or less than one (i.e., between zero and one) such that the volume of instillation fluid 105 delivered to the wound site 114 does not exceed the available space within the drape layer 117 (i.e. dead space), thereby minimizing the risk of inadvertent leakage from the wound dressing 112/drape layer 117. In some embodiments, the fluid instillation factor is between approximately 0.2 and approximately 0.8.

In addition to being used to calculate instillation fluid 105 volumes, in some embodiments, the NPWT system 100 may be additionally, or alternatively, used to monitor and track the progress of healing of the wound site 114 over time. Accordingly, in some embodiments, method 500 may optionally include the step 510 of estimating wound site 114 volume, and using the estimated volume to track healing progress of the wound site 114, discussed in more detail with reference to FIG. 11 below.

In some embodiments, it may be desired to remove instillation fluid 105 previously instilled to a wound site 114 from the wound site 114 at some time following the delivery of the instillation fluid 105 to the wound site 114. Accordingly, it may be advantageous to confirm, prior to instilling instillation fluid 105 to the wound site 114, that the dead space in the removed fluid canister 106 will be sufficient to receive the removed instillation fluid 105 and/or any additional fluid 121 (e.g. wound exudate) from the wound site 114 prior to delivering the additional instillation fluid 105 to the wound site 114. As such, method 500 may optionally include step 512 at which the volume of additional instillation fluid 105 calculated at step 508 is compared to the dead space of the removed fluid canister 106 (measured, e.g., during the determination of dead space at the wound site 114 at step 506), with an alarm being presented to the user at step 514 if the instillation fluid 105 to be delivered exceeds the dead space of the removed fluid canister 106. If the instillation fluid 105 to be delivered does not exceed the dead space of the removed fluid canister 106 (or if step 512 is not included as part of method 500), the calculated instillation fluid 105 is delivered to the wound site 114, with some or all of steps 504, 506, 508, 510, 512, 514, 516 being repeated any number of additional times over the course of the NPWT treatment.

Figure 6A:
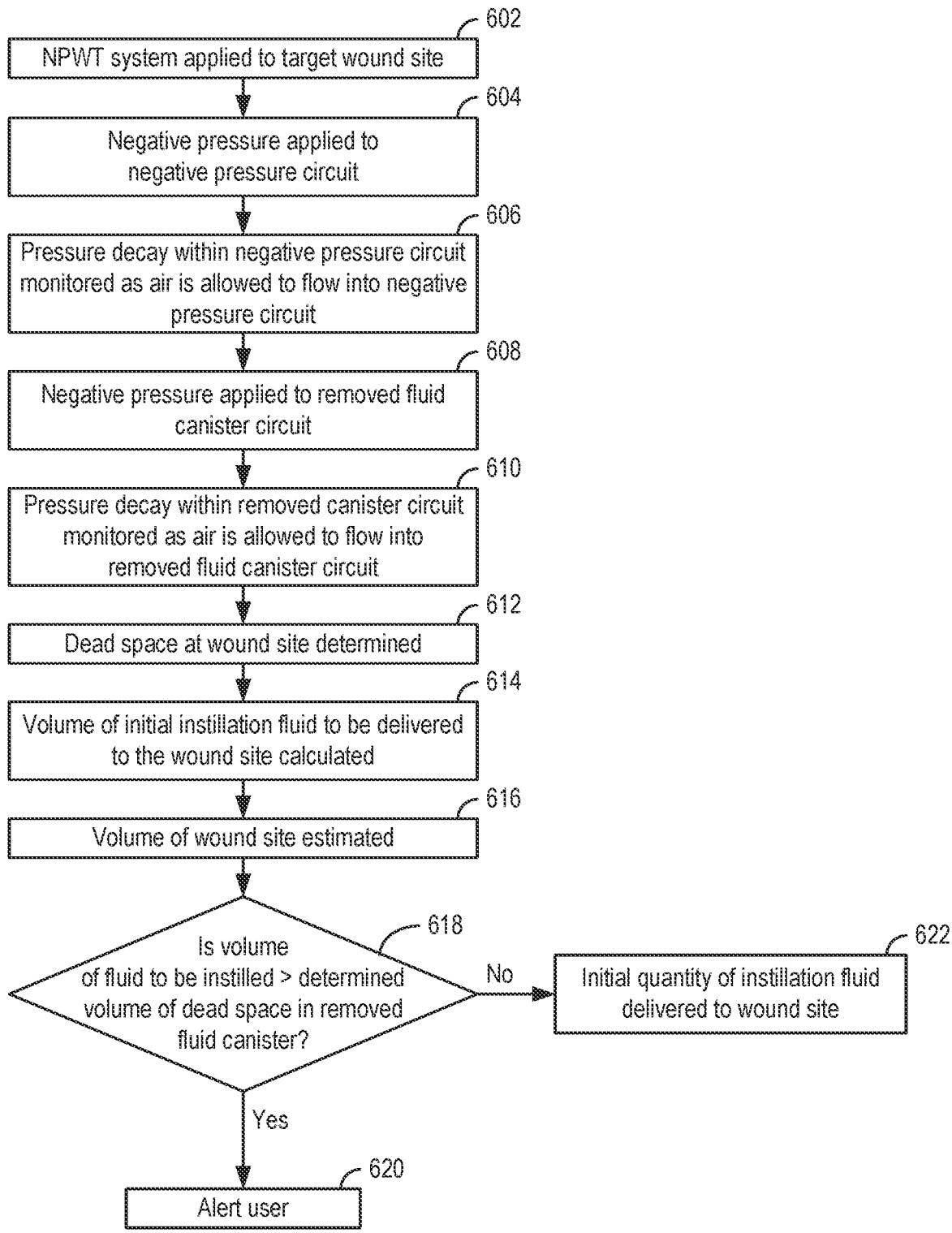
FIG. 6A is a flowchart of method of instilling an initial quantity of fluid to a wound site using the negative pressure wound therapy system, according to an exemplary embodiment.
Figure 6B:
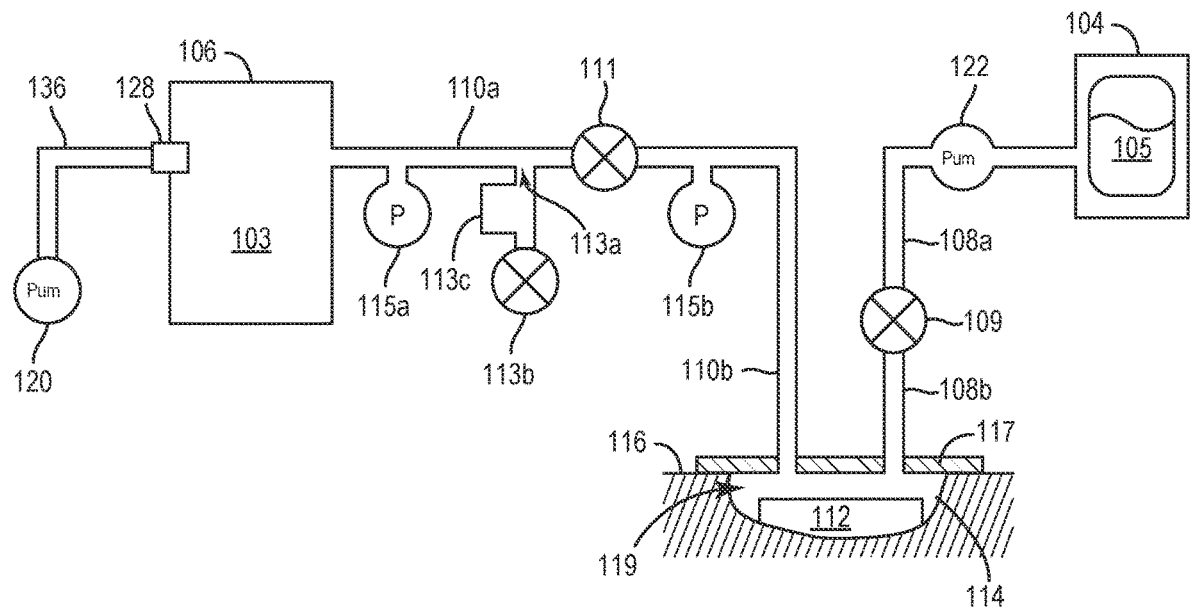
FIG. 6B illustrates a negative pressure wound therapy system applied to a desired wound site to be treated, prior to the instillation of an initial volume of fluid to the wound site according to an exemplary embodiment.

Referring to FIG. 6A a flowchart detailing the steps of a method 600 for an initial set up of NPWT system 100 and for delivery of an initial amount of instillation fluid 105 to a wound site 114 entailed in step 502 of the method 500 of FIG. 5 is shown according to one embodiment. At step 602, a NPWT system 100 (such as, e.g., illustrated in FIG. 1) is provided, with the drape layer 117 and wound dressing 112 being positioned at the desired wound site 114 to be treated, as shown, e.g., in FIG. 6B.

Figure 6C:
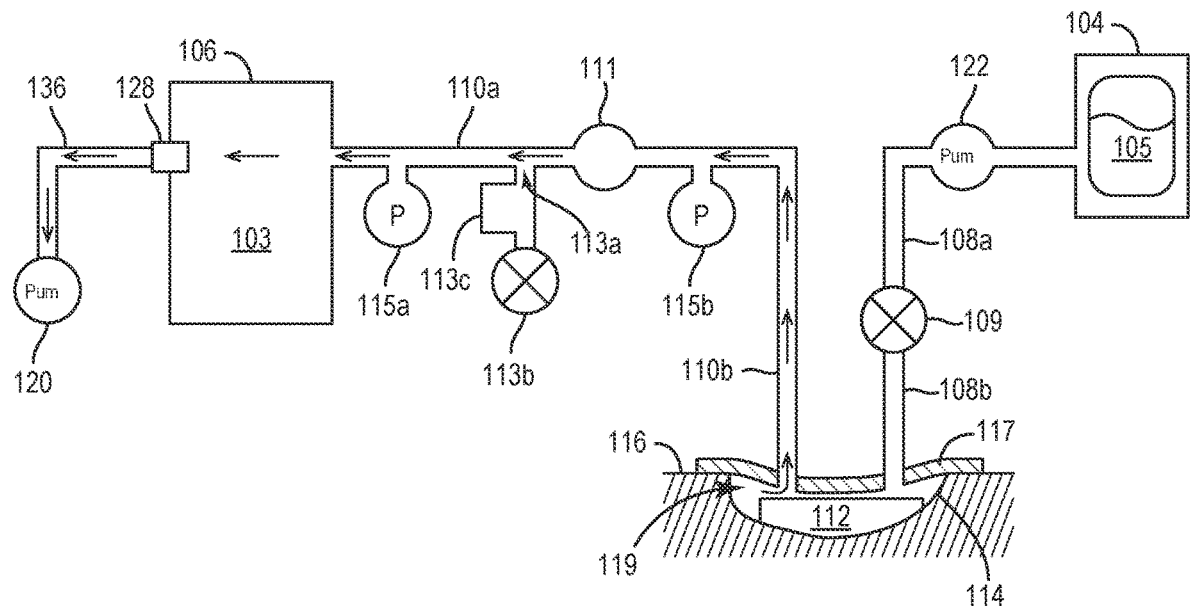
FIG. 6C illustrates the negative pressure wound therapy system of FIG. 6B following an application of a first negative pressure to the negative pressure wound therapy system, according to an exemplary embodiment.

Once the set-up of the NPWT system 100 at step 502 is complete, the determination of the dead space 119 available at the wound site 114 into which instillation fluid 105 may be delivered may begin at step 604 with the controller 118 operating the pneumatic pump 120 to establish a first desired negative pressure within the entirety of the negative pressure circuit 200, such as, e.g., illustrated in FIG. 6C.

In embodiments in which the tubing valve 111 comprises a normally-closed pressure sensitive valve that is openable in response to an applied, predetermined threshold negative pressure, the first desired negative pressure generated by the controller 118 at step 604 may be equal to or greater than the predetermined threshold pressure required to open the tubing valve 111, so as to ensure that the vacuum applied by the pneumatic pump 120 is applied across the entirety of the negative pressure circuit 200. In some embodiments, the threshold pressure required to open the tubing valve 111 may be a pressure of approximately negative 125 mmHg, with the controller 118 being configured to apply at step 604 a first negative pressure that is equal to or greater than negative 125 mmHg.

Alternatively, in embodiments in which the opening/closing of the tubing valve 111 is controlled manually or in direct response to a signal from the controller 118 (using, e.g., a tubeset module 300 as described below), the negative pressure delivered at step 604 may generally include any desired range of negative pressures, with step 604 including verification by the user and/or controller that the tubing valve 111 is in an open, flow orientation prior to the negative pressure being applied by the pneumatic pump 120. As illustrated, e.g., in FIG. 6C, according to various embodiments, the instillation tubing valve 109 and the vent valve 113b may be configured to be set to closed configurations during the application of negative pressure to the negative pressure circuit 200.

Figure 6D:
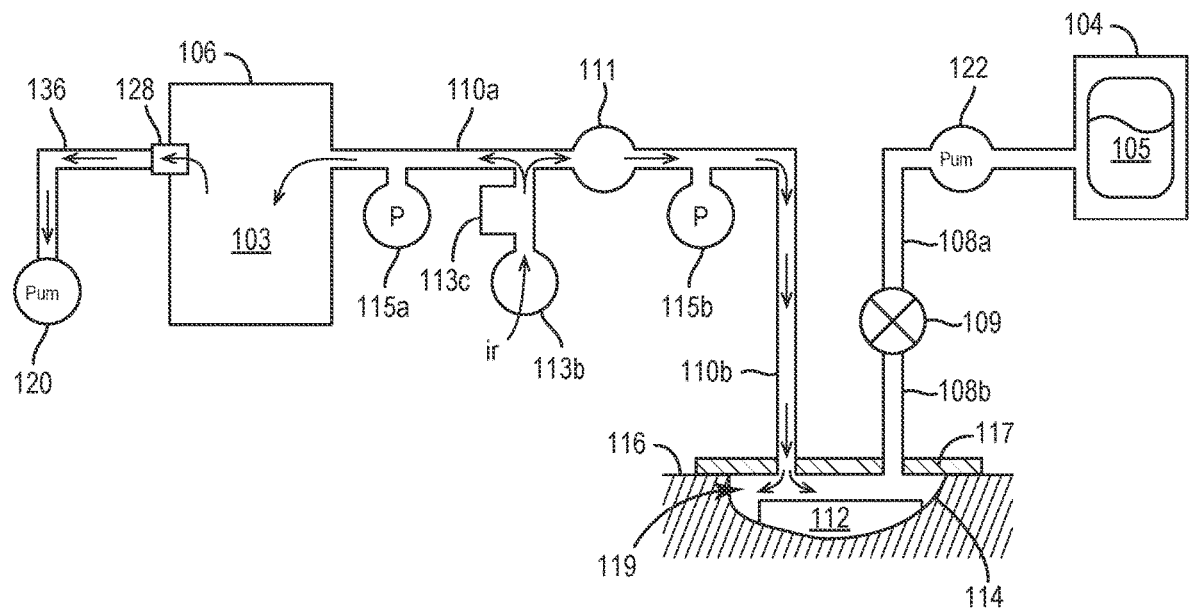
FIG. 6D illustrates the negative pressure wound therapy system of FIG. 6C during venting of the negative pressure wound therapy system following the application of the first negative pressure as shown in FIG. 6C, according to an exemplary embodiment.

As illustrated by FIG. 6D, at step 606, following the attainment of the desired first negative pressure within the negative pressure circuit 200 (as, e.g., measured and reported to the controller 118 by pressure sensor 115a and/or pressure sensor 115b), the operation of the pneumatic pump 120 is stopped, and the vent valve 113b is opened to allow air from the ambient environment surrounding the therapy device 102 to flow through the vent 113a and into the negative pressure circuit 200. According to various embodiments, the opening of the vent valve 113b at step 606 may be effectuated manually by a user or in response to instructions from the controller 118 being transmitted to the tubeset module 300. In yet other embodiments, the calibrated leak system 113 may be formed without a vent valve 113b (i.e. the vent 113a defines a constant leak within the tubing 110), such that air from the ambient environment surround the therapy device 102 will flow into the negative pressure circuit 200 without requiring any user and/or controller 118 intervention.

As air from the ambient environment flows in to the negative pressure circuit 200, parameters related to the flow of air through the vent 113a into the negative pressure circuit 200 are monitored (e.g. via flow detector 113c, pressure sensor 115a, pressure sensor 115b, etc.), with the measured parameters subsequently being used by the controller 118 at step 612 to determine the volume of the negative pressure circuit 200. According to various embodiments, the parameters related to the flow of air into the negative pressure circuit 200 may include, e.g., the rate of flow of air into the negative pressure circuit 200 (as measured, e.g., by flow detector 113c), the duration of time required for pressure within the negative pressure circuit 200 to increase to a predetermined pressure (e.g. ambient pressure) following the opening of the vent 113a and/or following operation of the pump 120 being ceased, the changing pressure (as, e.g., measured by pressure sensor 115a and/or pressure sensor 115b) within the negative pressure circuit 200 as the pressure increases from the negative pressure applied at step 604 to the predetermined pressure, etc.

Figure 6E:
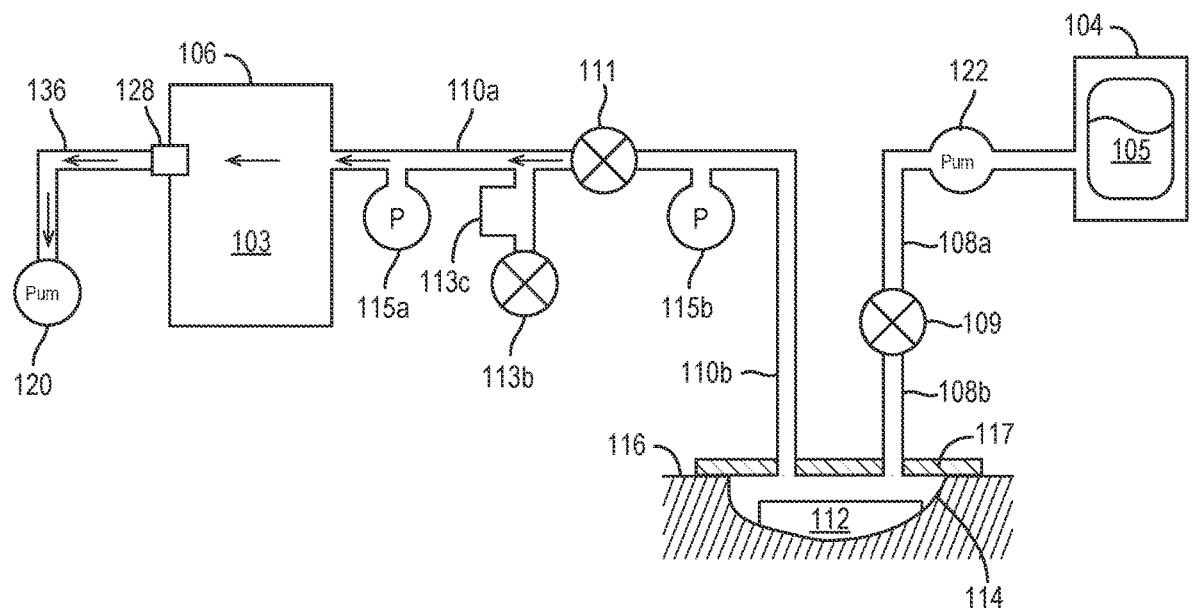
FIG. 6E illustrates the negative pressure wound therapy system of FIG. 6B following an application of a second negative pressure to the negative pressure wound therapy system, according to an exemplary embodiment.

Once the pressure within the negative pressure circuit 200 has increased to a desired pressure and the measurement of the desired parameters has been completed by the controller 118, the controller 118 may be configured operate pneumatic pump 120 to establish a second desired negative pressure within the removed fluid canister circuit 202 portion of the negative pressure circuit 200 at step 608, such as, e.g., illustrated in FIG. 6E. In embodiments in which the tubing valve 111 comprises a normally-closed pressure sensitive valve that is openable in response to an applied, predetermined threshold negative pressure, the second desired negative pressure generated by the controller 118 at step 608 may be less than the predetermined threshold pressure required to open the tubing valve 111, so as to ensure that the vacuum applied by the pneumatic pump 120 at step 608 is applied across only the removed fluid canister circuit 202 portion of the negative pressure circuit 200. For example, in some embodiments, the threshold negative pressure required to open the tubing valve 111 may be approximately negative 125 mmHg, with the controller 118 being configured to apply a negative pressure at step 608 that is less than negative 125 mmHg, such as, e.g., a pressure of approximately negative 50 mmHg.

Alternatively, in embodiments in which the opening/closing of the tubing valve 111 is controlled manually or in direct response to a signal from the controller 118, the negative pressure delivered at step 608 may generally include any desired range of negative pressures, with step 608 including verification by the user and/or controller that the tubing valve 111 is in a closed, no-flow orientation prior to the negative pressure being applied by the pneumatic pump 120. As will be understood, in such embodiments, the second negative pressure applied by the controller 118 at step 608 to the removed fluid canister circuit 202 may include a pressure that is equal to or different from the negative pressure that is applied by the controller 118 at step 604 to the negative pressure circuit 200. As illustrated, e.g., in FIG. 6E, according to various embodiments, the instillation tubing valve 109 and the vent valve 113b may be configured to be set to closed configurations (either manually or automatically, e.g., using tubeset module 300) during the application of negative pressure to the removed fluid canister circuit 202 at step 608.

Figure 6F:
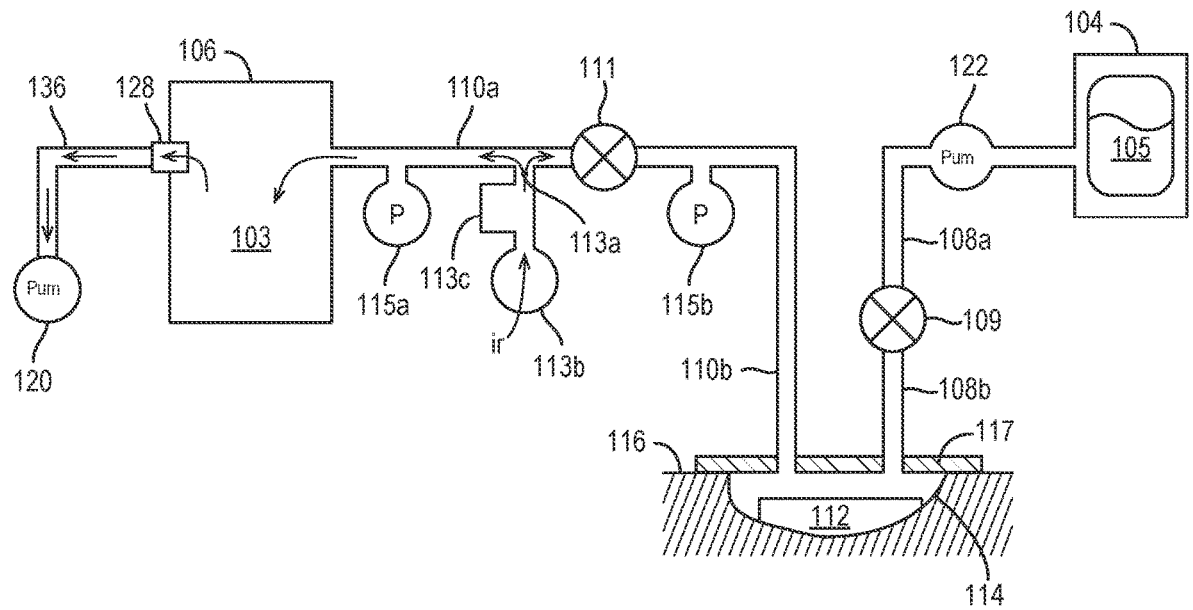
FIG. 6F illustrates the negative pressure wound therapy system of FIG. 6E during venting of the negative pressure wound therapy system following the application of the second negative pressure as shown in FIG. 6E, according to an exemplary embodiment.
Figure 6G:
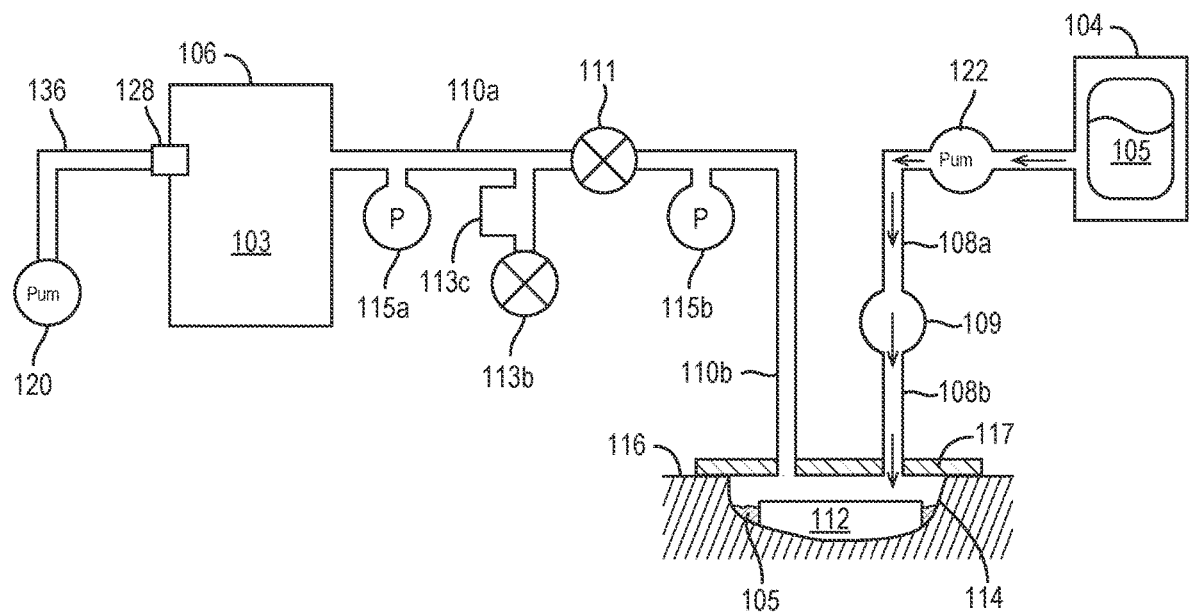
FIG. 6G illustrates the instillation of fluid to the wound site using the wound therapy system of FIG. 6B, according to an exemplary embodiment.

As illustrated by FIG. 6F, at step 610, following the attainment of the desired second negative pressure within the removed fluid canister circuit 202 (as, e.g., measured and reported to the controller 118 by pressure sensor 115a and/or pressure sensor 115b), the operation of the pneumatic pump 120 is stopped, and air from the ambient environment surrounding the therapy device 102 is allowed to flow through the vent 113a and into the removed fluid canister circuit 202. As air from the ambient environment flows into the removed fluid canister circuit 202, parameters related to the flow of air through the vent 113a and into the removed fluid canister circuit 202 are monitored, with the measured parameters subsequently being used by the controller 118 to calculate the volume of the removed fluid canister circuit 202 at step 612. According to various embodiments, the parameters related to the flow of air into removed fluid canister circuit 202 may include, e.g., the rate of flow of air into the removed fluid canister circuit 202 (as measured, e.g., by flow detector 113c), the duration of time required for pressure within the removed fluid canister circuit 202 to increase to a predetermined pressure (e.g. ambient pressure) following the opening of the vent 113a and/or ceasing operation or the pump 120 at step 610, the pressure (as, e.g., measured by pressure sensor 115a and/or pressure sensor 115b) within the removed fluid canister circuit 202 as the pressure increases from the negative pressure applied at step 608 to the predetermined pressure; etc.

At step 612, the controller 118 may be configured to determine the volumes of the removed fluid canister circuit 202 and the negative pressure circuit 200 based on the parameters measured at steps 606 and 610. According to some embodiments, the controller 118 may base these volume calculations on stored relationships between various measured parameter values and corresponding volumes. These relationships between measured parameter measurements and corresponding volumes that are stored by the controller 118 may include various functions, models, lookup table, etc., and may be based on pre-existing information input and stored by the controller 118, or on information obtained and processed by the controller 118 during an optional, initial training procedure conducted by the controller 118 prior to the use of the NPWT system 100 to treat wound site 114 (e.g. prior to the initiation of method 500; as part of the initial setup and initial instillation of instillation fluid of step 502; etc.). One non-limiting examples of embodiments of training procedures by which such relationships may be generated by the controller 118 are outlined in related, U.S. Provisional Application 62/650, 132, filed Apr. 17, 2018 and titled WOUND THERAPY SYSTEM WITH WOUND VOLUME ESTIMATION, the entire disclosure of which is incorporated by reference herein.

Using the determined volumes of the removed fluid canister circuit 202 and the negative pressure circuit 200, the controller 118 may determine the volume of the dead space 119 at the wound site 114 (i.e. the portion of the interior space defined between the wound site 114 and the lower surface of the drape layer 117 that is not occupied by the wound dressing 112 and/or any instillation fluid 105/other fluid) by subtracting the volume of the removed fluid canister circuit 202 from the volume of the negative pressure circuit 200. According to various embodiments, the determination of the volume of the dead space 119 at the wound site 114 at step 614 may also include subtracting or otherwise adjusting the calculated difference between the volumes of the removed fluid canister circuit 202 and the negative pressure circuit 200 to account for/factor in the known volumes of the downstream tubing portion 110b and the portion of the downstream instillation tubing 108b extending between the drape layer 117 and the instillation tubing valve 109 into the determination of the volume of the dead space 119 at the wound site 114.

At step 614, an initial quantity of instillation fluid 105 that is to be delivered to the wound site 114 is calculated. According to various embodiments, the calculated initial quantity of instillation fluid 105 that is delivered to the wound site 114 may be based on the volume of the dead space 119 calculated by the controller 118 at step 612. For example, in some embodiments, the controller 118 may calculate the initial volume of instillation fluid 105 to be delivered to the wound site 114 by multiplying the volume of dead space 119 calculated at step 612 by a fluid instillation factor. The fluid instillation factor may be equal to or less than one (i.e., between zero and one) such that the volume of instillation fluid 105 delivered to the wound site 114 does not exceed the available space within the drape layer 117 (thereby minimizing inadvertent leakage from the wound dressing 112/drape layer 117. In some embodiments, the fluid instillation factor is between approximately 0.2 and approximately 0.8. However, it is contemplated that the fluid instillation factor can have any value in various alternative embodiments.

As noted previously with reference to step 510, in addition to being used to calculate a quantity of instillation fluid 105 to be delivered during any stage of treatment using NPWT system 100 and under any number of different conditions (e.g. allowing for the calculation of additional instillation fluid 105 to be delivered at step 516 even if the removed fluid canister 106 has been emptied, or entirely replaced with a different sized removed fluid canister 106 during the course of treatment), in some embodiments the NPWT system 100 may be additionally, or alternatively, used to monitor and track the progress of healing of the wound site 114 over time. Accordingly, in some embodiments, at step 616, an initial baseline wound site 114 volume estimate may optionally be determined (via, e.g., a method as described with regards to FIG. 11 below) and stored by the controller 118, which may be used as a reference point against which future wound site 114 volume estimates may be compared to track healing progression of the wound site 114.

For reasons similar to those described with reference to step 512 of the method 500 of FIG. 5, according to some embodiments, at step 618 the amount of initial instillation fluid 105 that is to be delivered calculated at step 614 may be compared to a determined dead space 103 of the removed fluid canister 106 to determine whether the dead space within the removed fluid canister 106 will be sufficient to collect any fluids 121 from the wound site 114 (including non-absorbed instillation fluid 105) following the delivery of instillation fluid 105 at step 516. As will be understood, in embodiments in which the NPWT system 100 has not been operated prior to the use of the NPWT system 100 at step 602, the volume of the removed fluid canister 106 should be empty, such that the dead space 103 of the removed fluid container 106 should be equal to the volume of the removed fluid canister 106. If the volume of the removed fluid canister 106 is not known and/or if removed fluid 107 is present in the removed fluid canister 106 at step 602, the dead space 103 of the removed fluid container may be calculated by subtracting the known volumes of conduit 136 and the upstream tubing portion 110a from the volume of the removed fluid canister circuit 202 determined at step 614. Similar to step 514, at step 620 an alarm may be presented to a user if the initial volume of instillation fluid 105 to be delivered calculated at step 614 exceeds the dead space 103 of the removed fluid canister 106. Otherwise, if the volume of the initial instillation fluid 105 to be delivered does not exceed the dead space 103 of the removed fluid canister 106, the calculated instillation fluid 105 is delivered to the wound site 114 at step 622, as shown, e.g., in FIG. 6F.

Figure 7:
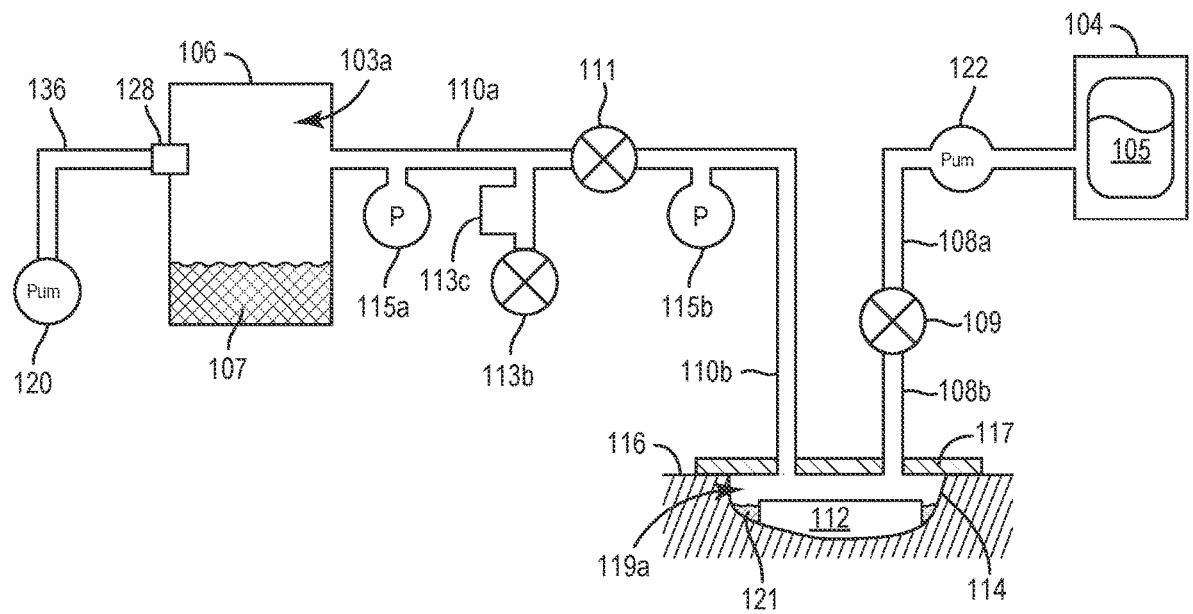
FIG. 7 illustrates a negative pressure wound therapy system applied to a wound site following an initial instillation of fluid to the wound site, according to an exemplary embodiment.

Referring to FIG. 7, a NPWT system 100 according to one embodiment is shown at a point in time subsequent to a decision to instill additional instillation fluid 105 to the wound site 114 at step 504 of the method 500 of FIG. 5, but prior to the determination of wound dead space at the wound site at step 506. As shown in FIG. 7, at the time immediately preceding the determination of dead space at the wound site 114 at step 506, a quantity of fluid 121 (e.g. non-absorbed instillation fluid 105 from a prior instillation, wound exudate, etc.) may be present in the space between the drape layer 117 and the wound site 114, with the remaining space between the drape layer 117 and the wound site 114 defining an initial dead space 119a. As also shown in FIG. 7, according to some embodiments, an initial quantity of removed fluid 107 may be present in the removed fluid canister 106 at the time immediately preceding the start of step 506, with the remaining volume of the removed fluid canister 106 being defined by an initial dead space 103a. As will be understood, according to some embodiments, no fluid may be present at either the wound site 114 and/or in the removed fluid canister 106 at the time immediately preceding step 506, in which embodiments the quantities of each of the fluid 121 in the wound space and the removed fluid 107 in the removed fluid canister 106 would be equal to zero.

As noted above, a quantity of fluid 121 may be present at the wound site 114 immediately prior to the initiation of step 506. According to some embodiments, it may not be desired and/or required to remove fluid 121 from the wound site (e.g. non-absorbed instillation fluid 105 from prior instillations, wound exudate, etc.) prior to the delivery of additional instillation fluid 105 to the wound site 114 at step 516 of the method 500 of FIG. 5. Accordingly, in some embodiments of method 500, the additional instillation fluid 105 instilled to the wound site at step 516 may be delivered to the wound site 114 irrespective of any fluid 121 that may be present at the wound site 114.

Referring to FIGS. 8A-8E, one embodiment of a method 800 of determining an amount of dead space at a wound site 114 which may be used at step 506 of the method 500 of FIG. 5 in embodiments in which fluid 121 from the wound site 114 is not removed from the wound site 114 prior to instilling additional instillation fluid 105 is illustrated. In particular, according to the method 800 of FIGS. 8A-8E, as no fluid 121 is displaced from the wound site 114 during the method 800 (i.e. step 506), the final dead space into which the additional instillation fluid 121 will be instilled will be the same initial dead space 119a at the wound site that is present immediately prior to the initiation of step 506 (i.e. the dead space 119a shown in FIG. 7).

Figure 8A:
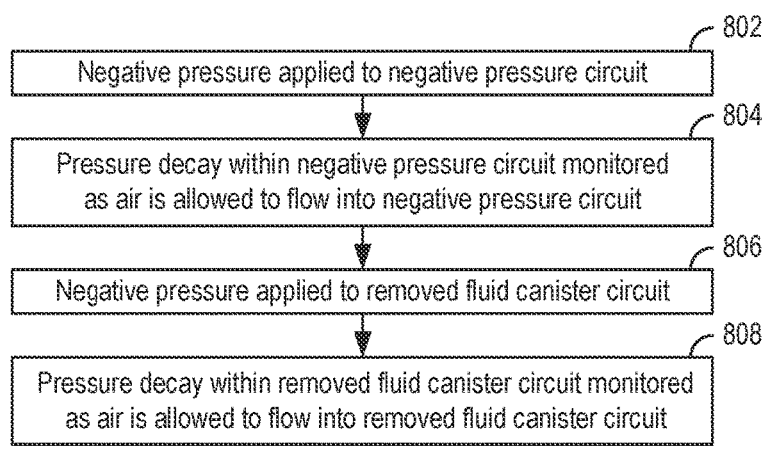
FIG. 8A is a flowchart of method of instilling an additional quantity of fluid to a wound site using the negative pressure wound therapy system of FIG. 7, according to an exemplary embodiment.
Figure 8B:
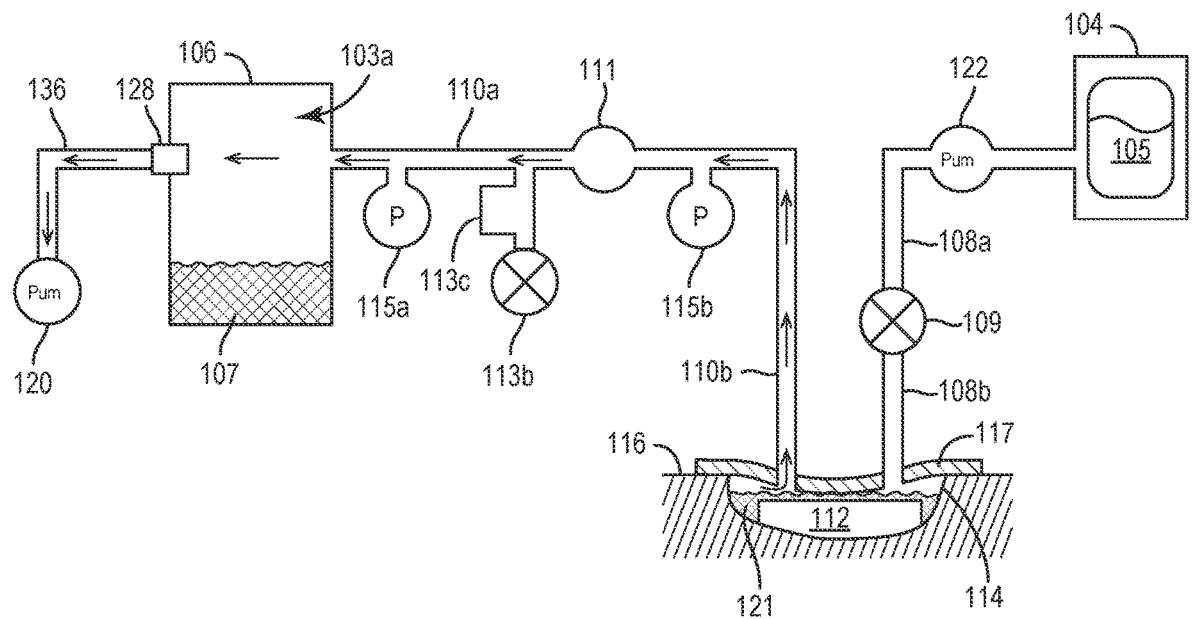
FIG. 8B illustrates the negative pressure wound therapy system of FIG. 7 following an application of a first negative pressure to the negative pressure wound therapy system, according to an exemplary embodiment.
Figure 8C:
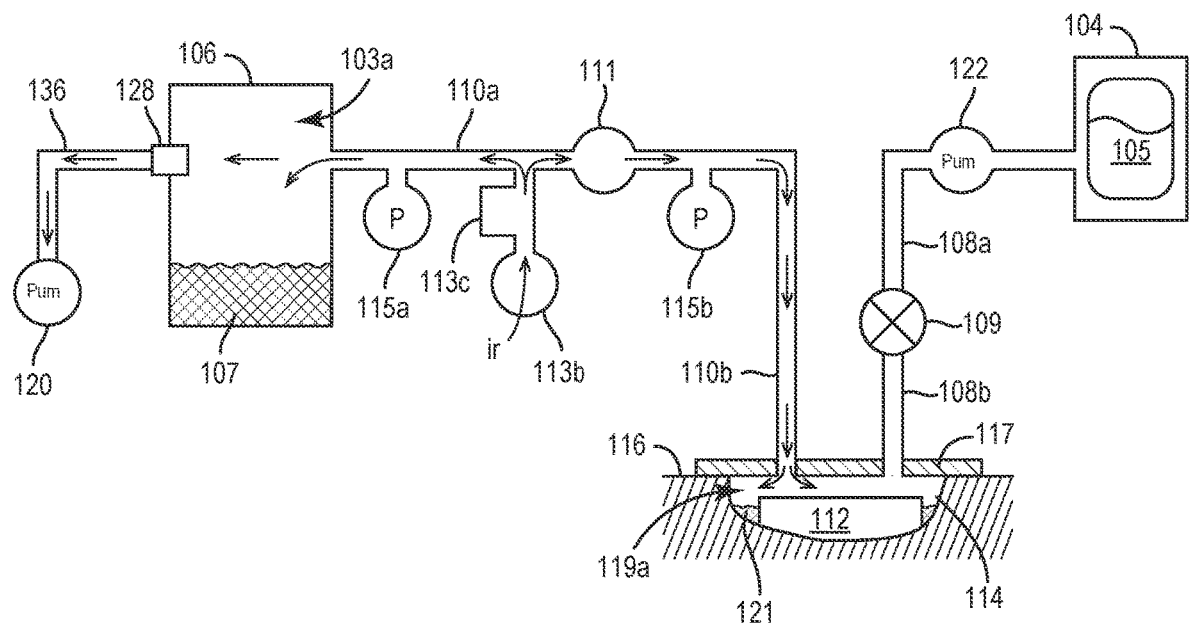
FIG. 8C illustrates the negative pressure wound therapy system of FIG. 8B during venting of the negative pressure wound therapy system following the application of the first negative pressure as shown in FIG. 8B, according to an exemplary embodiment.
Figure 8D:
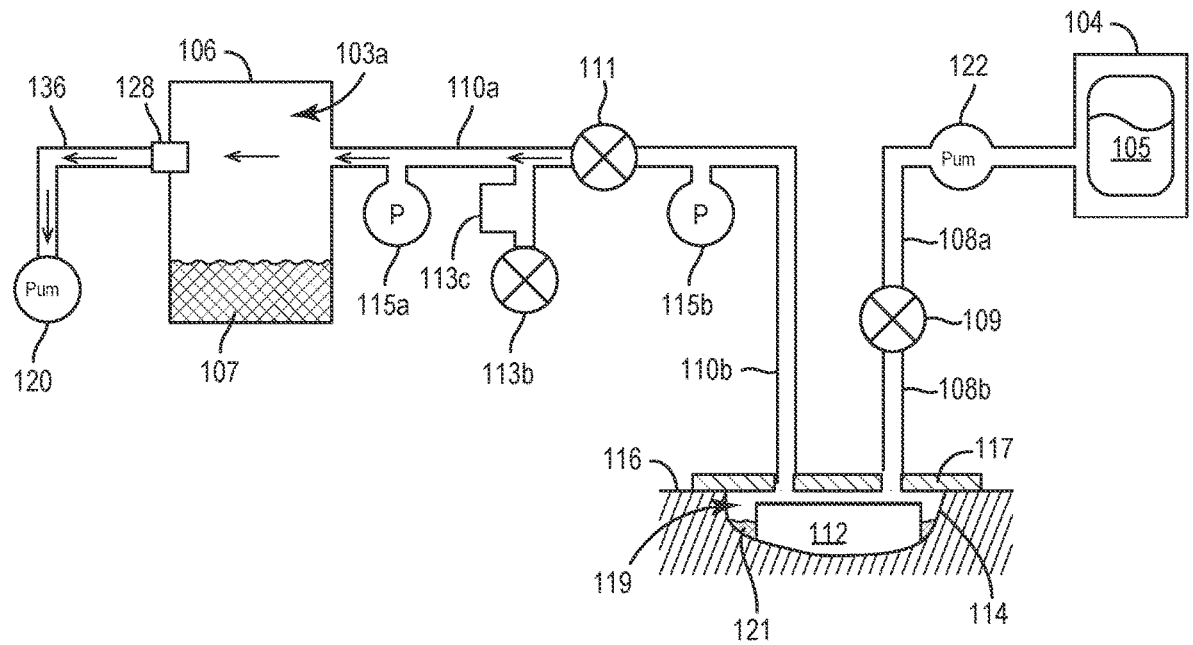
FIG. 8D illustrates the negative pressure wound therapy system of FIG. 7 following an application of a second negative pressure to the negative pressure wound therapy system, according to an exemplary embodiment.
Figure 8E:
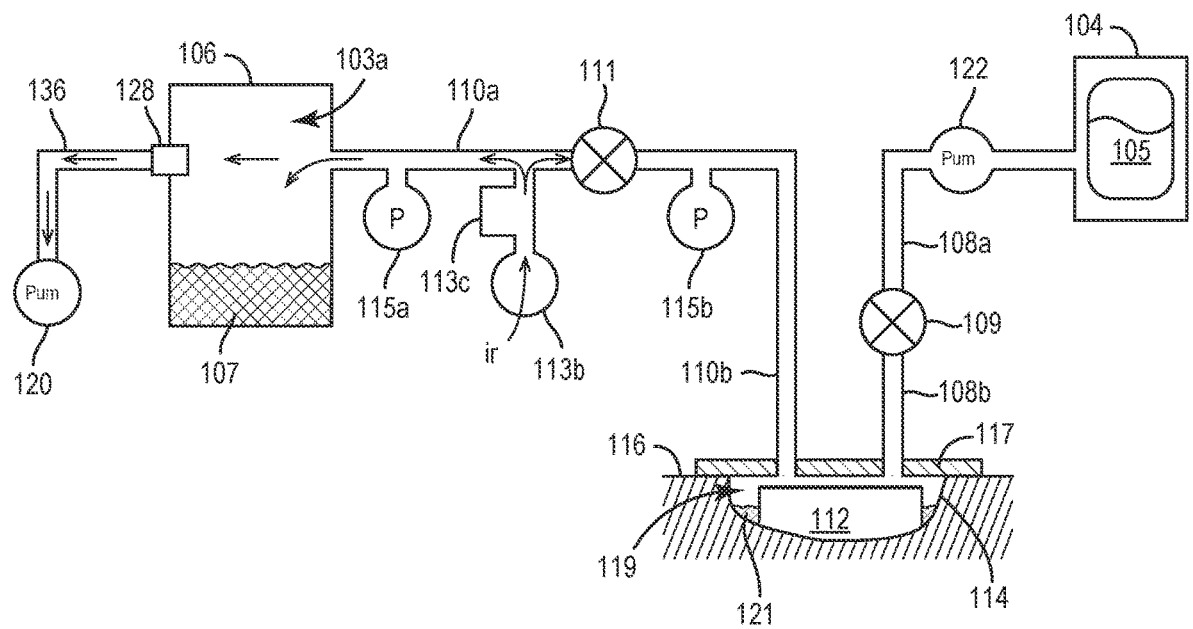
FIG. 8E illustrates the negative pressure wound therapy system of FIG. 8D during venting of the negative pressure wound therapy system following the application of the first negative pressure as shown in FIG. 8D, according to an exemplary embodiment.

As shown by the flowchart in FIG. 8A, the method 800 of determining dead space is substantially the same as the method 600 of calculating the dead space 119 upon initial instillation of instillation fluid 105 to the wound site 114 at step 502 (which is discussed in more detail with reference to FIGS. 6A-6G). In particular, similar to steps 604 and 606, the method 800 of FIG. 8A also includes steps 802 and 804 (shown, e.g., in FIGS. 8B and 8C, respectively) during which negative pressure is applied to and removed from the negative pressure circuit 200. Similar to steps 608 and 610 of the method 600 of FIG. 6A, the method 800 of FIG. 8 also includes steps 806 and 808 (shown, e.g., in FIGS. 8D and 8E, respectively) during which negative pressure is applied to and removed from the removed fluid canister circuit 202. Also similar to the method 600 of FIG. 6A, in the method 800 of FIGS. 8A-8E, the application and subsequent removal of negative pressure to the negative pressure circuit 200 of steps 802 and 804 may be performed either prior to or after the application and subsequent removal of negative pressure to the removed fluid canister circuit 202 of steps 806 and 808.

As noted above, the method 800 of FIGS. 8A-8E may be performed in substantially the same manner as the method 600 described with references to FIG. 6A above. However, whereas, as described above with reference to the method of FIGS. 6A-6E, according to various embodiments, any range of negative pressures may generally be applied to the negative pressure circuit 200 at step 604 of method 600, the negative pressure applied to the negative pressure circuit 200 at step 802 of the method 800 must be limited to negative pressures that will not result in the fluid 121 at the wound site 114 being displaced into the removed fluid canister 106.

Following the completion of step 808, the controller 118 may be configured to calculate the volume of the dead space 119a at the wound site 114 (which corresponds to the maximum volume of additional installation fluid 105 that may be delivered to wound site 114) at step 508 of method 500 of FIG. 5. More specifically at step 508, after calculating the volumes of the removed fluid canister circuit 202 and the negative pressure circuit 200 based on the parameters measured at steps 804 and 808 (in a manner similar to that described with reference to step 612 of the method 600 of FIGS. 6A-6G), the dead space 119a at the wound site 114 may be calculated based on subtracting the measured volume of the removed fluid canister circuit 202 from the measured volume of the negative pressure circuit 200, with the volume of the removed fluid canister circuit 202 of the method 800 of FIGS. 8A-8E being defined by the dead space 103a of the removed fluid canister 106, conduit 136 and upstream tubing portion 110a; and the volume of the negative pressure circuit 200 being defined by the volume of the removed fluid canister circuit 202 (i.e. dead space 103a of the removed fluid canister 106, conduit 136 and upstream tubing portion 110a), the downstream tubing portion 110b, dead space 119a of the wound site 114 and the portion of downstream installation tubing 108b extending between the drape layer 117 and installation tubing valve 109.

According to various embodiments, in embodiments of method 500 in which the determination of the volume of the dead space 119a at the wound site 114 at step 508 is based on measured parameters related to the removed fluid canister circuit 202 and negative pressure circuit 200 obtained using the method 800 of FIGS. 8A-8E, step 508 may also include subtracting or otherwise adjusting the calculated difference between the volumes of the removed fluid canister circuit 202 and the negative pressure circuit 200 to account for/factor in the known volumes of the downstream tubing portion 110b and the portion of the downstream installation tubing 108b extending between the drape layer 117 and the installation tubing valve 109 into the determination of the volume of the dead space 119a at the wound site 114.

Although, as described above, in some embodiments of method 500, additional installation fluid 105 may be delivered at step 516 without first removing any remaining fluid 121 at the wound site 114, according to other embodiments, it may be desirable to remove fluid 121 from the wound site 114 prior to the delivery of additional installation fluid 105.

Referring to FIGS. 9A-9E, one embodiment of a method 900 of determining an amount of dead space at a wound site 114 which may be used at step 506 of the method 500 of FIG. 5 in embodiments in which it is desired to remove fluid 121 from the wound site 114 prior to instilling additional installation fluid 105 is illustrated. In particular, according to the method 900 of FIGS. 9A-9E, any fluid 121 initially at the wound site 114 immediately prior to step 506 (e.g. as shown in FIG. 7) is displaced from the wound site 114 during the method 900 (i.e. step 506), such the final dead space 119b into which the additional installation fluid 121 will be instilled will be greater than the initial dead space 119a at the wound site that is present immediately prior to the initiation of step 506 by an amount generally corresponding to a volume of the fluid 121 displaced from the wound site 114 to the removed fluid canister 106 during the method 900.

As shown by the flowchart in FIG. 9A, the method 900 of determining dead space is substantially the same as the method 600 of calculating the dead space 119 upon initial installation of installation fluid 105 to the wound site 114 at step 502 (discussed in more detail with reference to FIGS. 6A-6G). In particular, similar to steps 604 and 606, the method 900 of FIG. 9A also includes steps 902 and 904 (shown, e.g., in FIGS. 9B and 9C, respectively) during which negative pressure is applied to and removed from the negative pressure circuit 200. Similar to steps 608 and 610 of the method 600 of FIG. 6A, the method 900 of FIG. 9 also includes steps 906 and 908 (shown, e.g., in FIGS. 9D and 9E, respectively) during which negative pressure is applied to and removed from the removed fluid canister circuit 202.

Figure 9A:
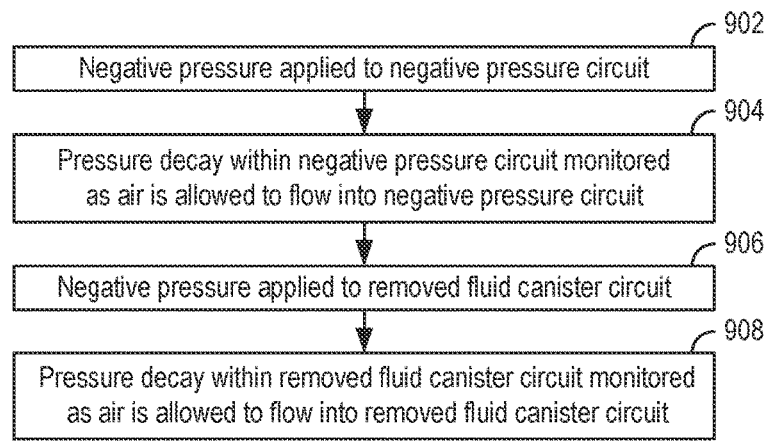
FIG. 9A is a flowchart of method of instilling an additional quantity of fluid to a wound site to the negative pressure wound therapy system of FIG. 7, according to an exemplary embodiment.
Figure 9B:
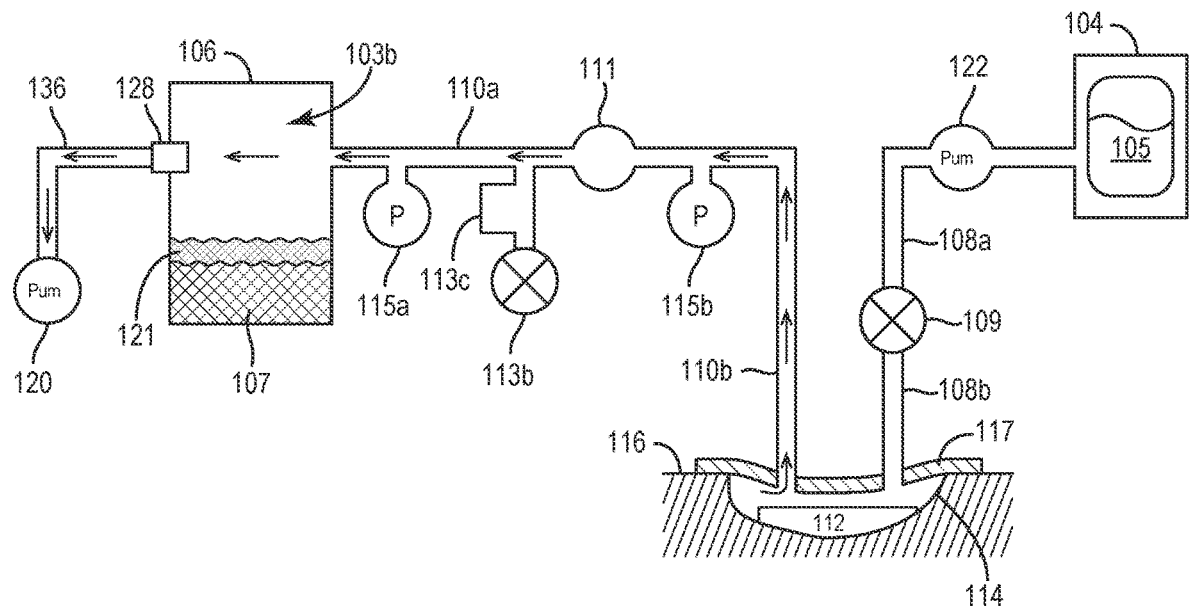
FIG. 9B illustrates the negative pressure wound therapy system of FIG. 7 following an application of a first negative pressure to the negative pressure wound therapy system, according to an exemplary embodiment.
Figure 9C:
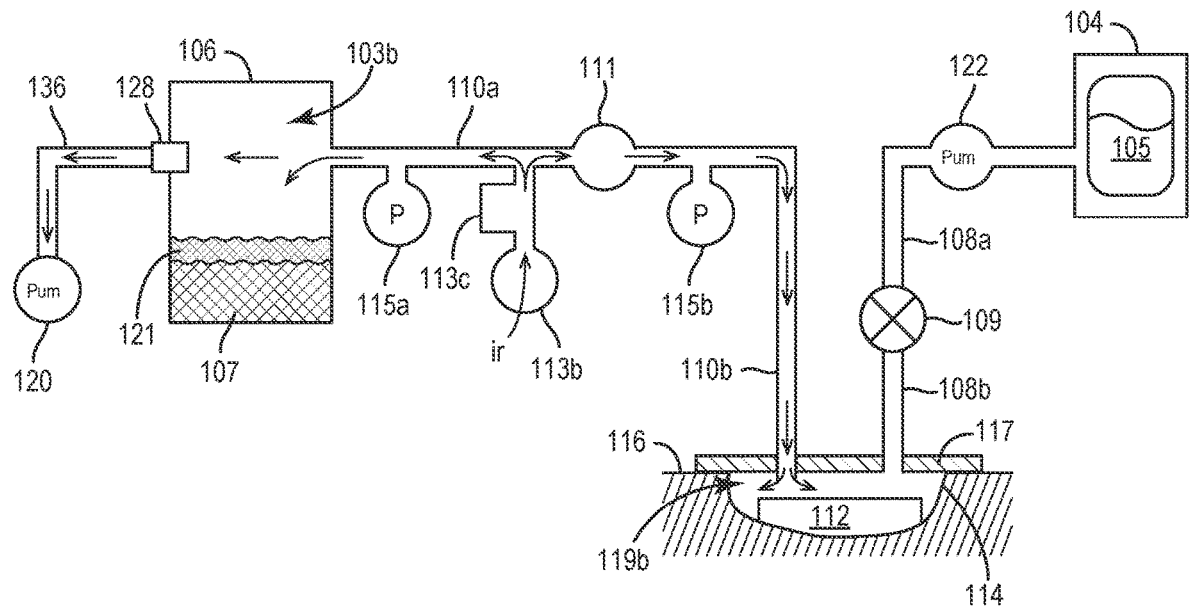
FIG. 9C illustrates the negative pressure wound therapy system of FIG. 9B during venting of the negative pressure wound therapy system following the application of the first negative pressure as shown in FIG. 9B, according to an exemplary embodiment.
Figure 9D:
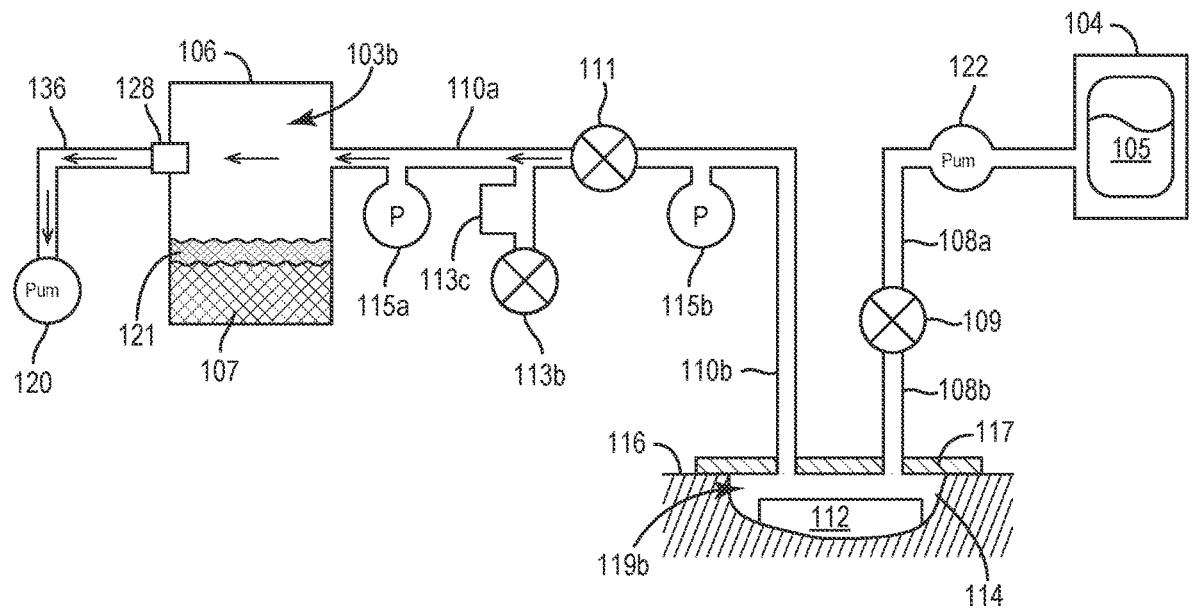
FIG. 9D illustrates the negative pressure wound therapy system of FIG. 7 following an application of a second negative pressure to the negative pressure wound therapy system, according to an exemplary embodiment.
Figure 9E:
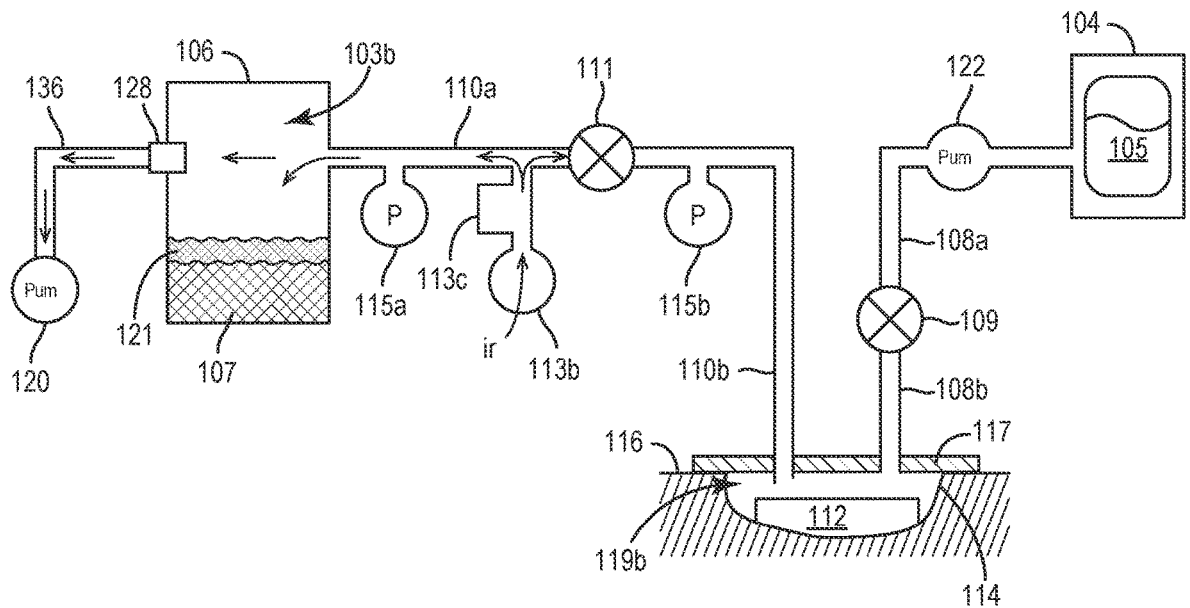
FIG. 9E illustrates the negative pressure wound therapy system of FIG. 9D during venting of the negative pressure wound therapy system following the application of the first negative pressure as shown in FIG. 9D, according to an exemplary embodiment.

However, unlike the method 600 of FIG. 6A in which the application and subsequent removal of negative pressure to the negative pressure circuit 200 at steps 604 and 608 may be performed either prior to or after the application and subsequent removal of negative pressure to the removed fluid canister circuit 202 of steps 610 and 612, in the method 900 of FIG. 9A, the application and subsequent removal of negative pressure to the negative pressure circuit 200 at steps 902 and 904 is performed prior to the application and subsequent removal of negative pressure to the removed fluid canister circuit 202 of steps 906 and 908. Additionally, whereas, as described above with reference to the method of FIGS. 6A-6E, according to various embodiments, any range of negative pressures may generally be applied to the negative pressure circuit 200 at step 604 of method 600, the negative pressure applied to the negative pressure circuit 200 at step 902 of the method 900 of FIG. 9A must be sufficient to cause the displacement of fluid 121 from the wound site 114 into the removed fluid canister 106.

Following the completion of step 908, the controller 118 may be configured to calculate the volume of the final dead space 119b at the wound site 114 (which corresponds to the maximum volume of additional installation fluid 105 that may be delivered to wound site 114) at step 508 of method 500 of FIG. 5. More specifically at step 508, after calculating the volumes of the removed fluid canister circuit 202 and the negative pressure circuit 200 based on the parameters measured at steps 904 and 908 (in a manner similar to that described with reference to step 612 of the method 600 of FIGS. 6A-6G), the final dead space 119b at the wound site 114 may be calculated based on subtracting the measured volume of the removed fluid canister circuit 202 from the measured volume of the negative pressure circuit 200, with the volume of the removed fluid canister circuit 202 of the method 800 of FIGS. 9A-9E being defined by the final dead space 103b of the removed fluid canister 106 (with the final dead space 103b of the removed fluid canister 106 being generally equal to the difference between an initial dead space 103a within the removed fluid canister 106 and the volume of fluid 121 displaced into the removed fluid canister 106 from the wound site 114 at step 802, as shown, e.g., in FIG. 9B), conduit 136 and upstream tubing portion 110a; and the volume of the negative pressure circuit 200 being defined by the volume of the removed fluid canister circuit 202 (i.e. final dead space 103b of the removed fluid canister 106, conduit 136 and upstream tubing portion 110a), the downstream tubing portion 110b, final dead space 119b of the wound site 114 and the portion of downstream installation tubing 108b extending between the drape layer 117 and installation tubing valve 109.

According to various embodiments, in embodiments of method 500 in which the determination of the volume of the dead space 119 at the wound site 114 at step 508 is based on measured parameters related to the removed fluid canister circuit 202 and negative pressure circuit 200 obtained using the method 900 of FIGS. 9A-9E, step 508 may also include subtracting or otherwise adjusting the calculated difference between the volumes of the removed fluid canister circuit 202 and the negative pressure circuit 200 to account for/ factor in the known volumes of the downstream tubing portion 110b and the portion of the downstream instillation tubing 108b extending between the drape layer 117 and the instillation tubing valve 109 into the determination of the volume of the dead space 119a at the wound site 114.

In some embodiments of method 500 of FIG. 5 in which fluid 121 from the wound site 114 is removed prior to the instillation of additional instillation fluid 105 at step 516, it may be desirable to ensure that the initial dead space 103a in the removed fluid canister 106 immediately prior to beginning the step of determining dead space at the wound site at step 506 is sufficient to hold fluid 121 that will be displaced from the wound site 114 into the removed fluid canister during step 506, so as to avoid the risk of removed fluid canister 106 overflow.

Accordingly, in some embodiments of method 500 in which fluid 121 from the wound site 114 is removed prior to the instillation of any additional instillation fluid 105 at step 516, the method of step 506 of determining dead space at the wound site 114 (e.g., such as described with reference to the method 900 of FIGS. 9A-9E) may include determining whether there is sufficient dead space at the removed fluid canister 106 to hold the fluid 121 from the wound site 114 that may be displaced into the removed fluid canister 106 as part of the method of determining dead space at the wound site 114.

Figure 10A:
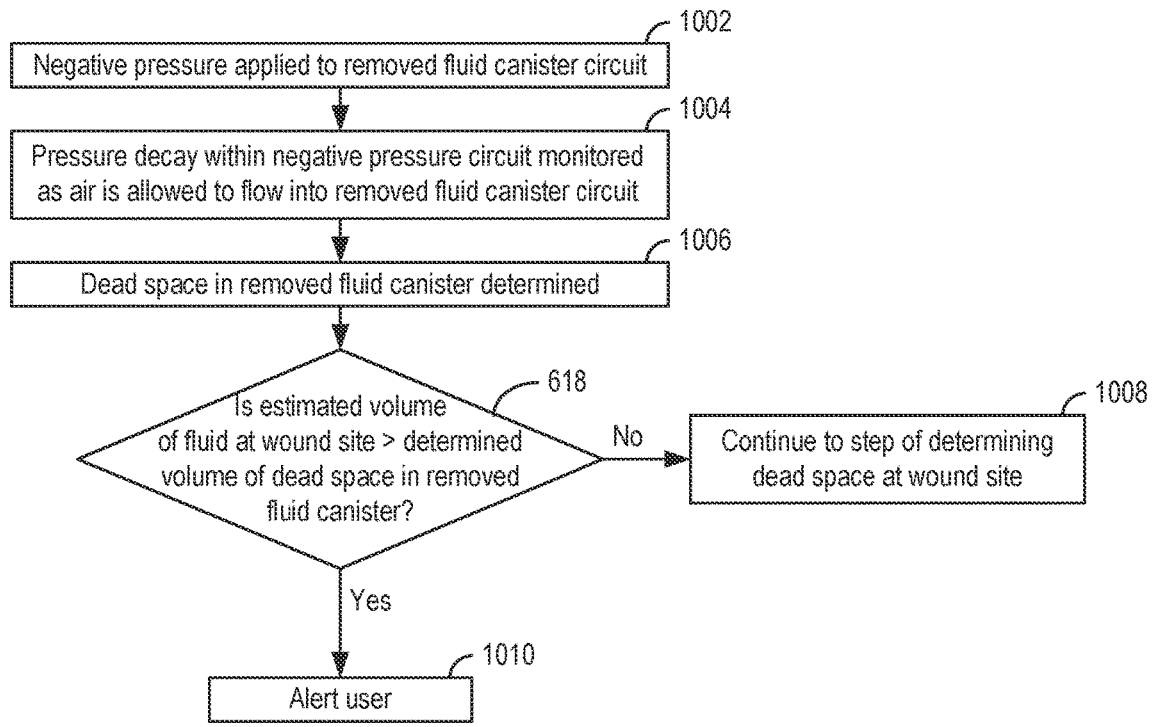
FIG. 10A is a flowchart of a method of determining whether sufficient dead space is present in a negative pressure wound therapy system, according to an exemplary embodiment.
Figure 10B:
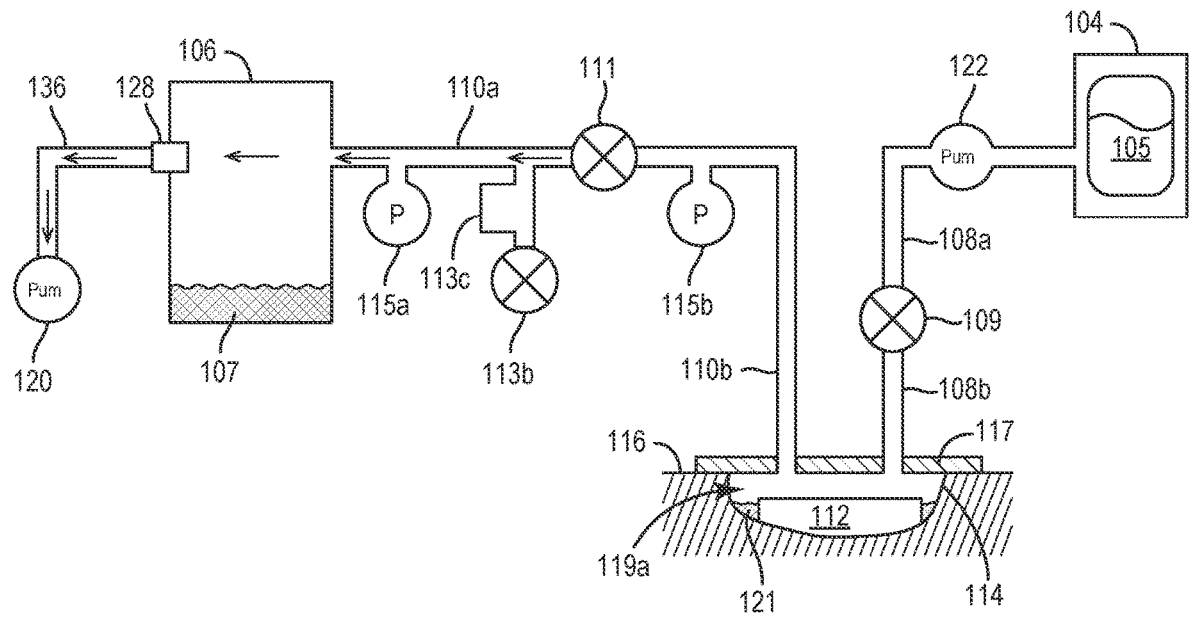
FIG. 10B illustrates the negative pressure wound therapy system of FIG. 7 following an application of a first negative pressure to the negative pressure wound therapy system, according to an exemplary embodiment.
Figure 10C:
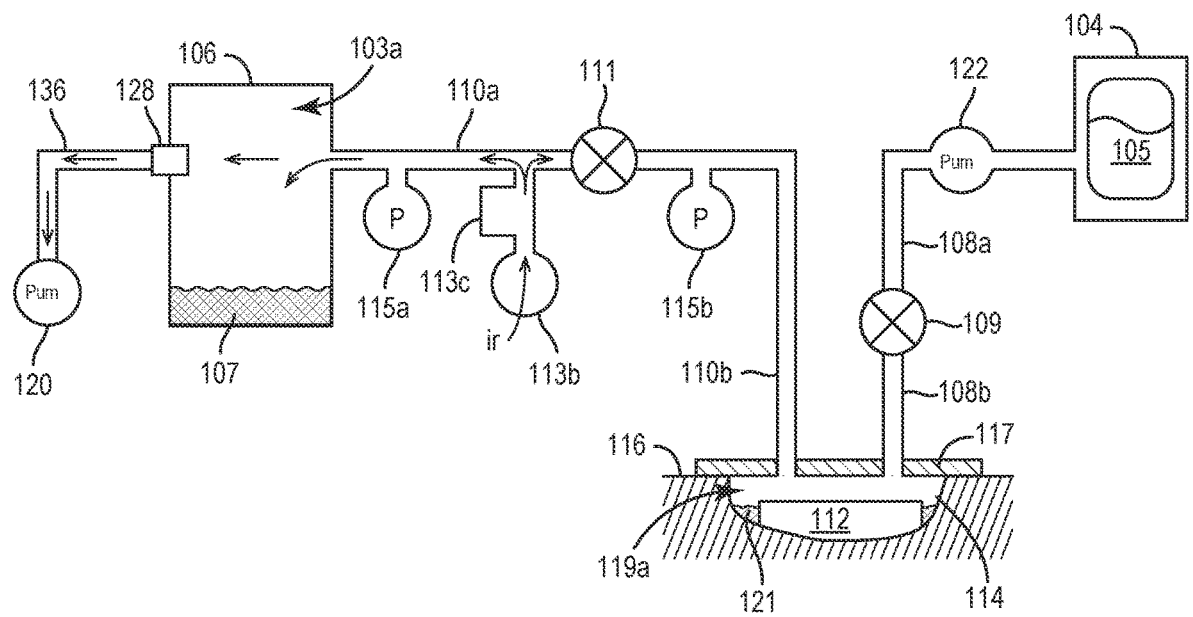
FIG. 10C illustrates the negative pressure wound therapy system of FIG. 10B during venting of the negative pressure wound therapy system following the application of the first negative pressure as shown in FIG. 10B, according to an exemplary embodiment.

Illustrated in FIGS. 10A-10C is one embodiment of such a method that may be used to minimize the risk of overflow of the removed fluid canister 106 during step 506 in which dead space at the wound site 114 is being determined (e.g., via method 900 as described in FIGS. 9A-9E). At steps 1002 and 1004 (shown in FIGS. 10B and 10C, respectively) negative pressure is applied to and removed from the removed fluid canister circuit 202 to determine the initial dead space 103a in the removed fluid canister 106 prior to beginning step 506 (e.g. as shown in FIG. 7). In general, the steps 1002 and 1004 of the method 1000 of FIGS. 10A-10E may be performed in a manner substantially similar to the manner in which steps 608 and 610 of the method 600 of FIGS. 6A-6G are performed. At step 1006, the volume of the removed fluid canister circuit 202 is calculated based on the parameter measured at step 1004 (in a manner similar to that described with reference to step 612 of the method 600 of FIGS. 6A-6G). Once the volume of the removed fluid canister circuit 202 has been calculated, the known volumes of the conduit 136 and the upstream tubing portion 110a may be subtracted from the calculated removed fluid canister circuit 202 to determining the volume of the initial dead space 103a in the removed fluid canister 106 (i.e. the maximum volume of fluid 121 displaced from the wound site 114 that the removed fluid canister 106 may hold).

Once the volume of the initial dead space 103a has been calculated at step 1006, at step 1008, the controller 118 may be configured to estimate the volume of the fluid 121 at the wound site 114 at the time immediately preceding the determination of dead space at the wound site 114 at step 506. The volume of the fluid 121 at the wound site 114 may be based on any number of different factors and variables such as, e.g., stored values of quantities of instillation fluid 105 previously delivered to the wound site 114, stored values of fluid 121 previously removed from the wound site, elapsed time (e.g. from a prior instillation, a prior removal of fluid 121, etc.), etc., with the controller 118 at step 1008 further being configured to compare this estimated volume of fluid 121 to the initial dead space 103a calculated at step 1006, alerting the user to empty the removed fluid canister 106 at step 1010 if the controller 118 determines that the estimated fluid 121 volume exceeds the calculated initial dead space 103a. If the calculated initial dead space 103a is sufficient to hold the estimated volume fluid 121 from the wound site 114, at step 1012 the controller 118 may be configured to begin the step 506 of determining dead space at the wound site 114, e.g., according to method 900 as described with reference to FIGS. 9A-9E.

As noted above, according to some embodiments of method 500, it may be advantageous to monitor changes in the volume of the wound site 114 to track the progress of the healing of the wound site 114 at an optional step 510.

In general, the volume of the wound site 114 is defined by the entirety of the interior extending between the wound site 114 and the drape layer 117 attached to the skin 116 about the wound site 114. At various points during treatment using the NPWT system 100, located within and defining the volume of the wound site may be any one of, and any combination of: the wound dressing 112, fluid 121, and/or dead space 119. As will be understood, unless the wound dressing 112 is replaced during treatment, the volume of the wound site 114 volume occupied by the wound dressing 112 will generally remain unchanged over the course of treatment, whereas the portion of the wound site 114 volume occupied by the fluid 121 and/or dead space 119 may change with time.

Figure 11:
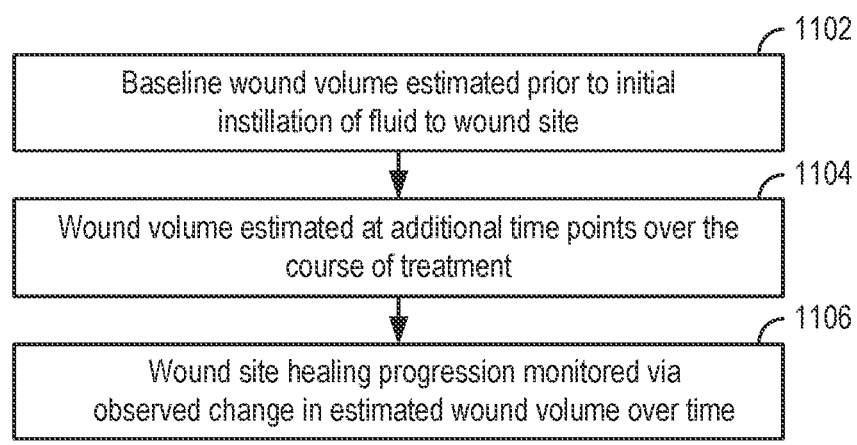
FIG. 11 is a flowchart of a process for monitoring the healing progression of the wound site over time, according to an exemplary embodiment.

Referring to FIG. 11, a block diagram illustrating one embodiment of a method 1100 of tracking wound site 114 healing progression which may be used at step 510 of the method 500 of FIG. 5 is illustrated. At step 1102, an initial volume of the wound site 114 is estimated and recorded by the controller 118 at a point in time prior to an initial instillation of instillation fluid 105 to the wound site 114, and may serve as a baseline against which subsequent wound site 114 volume estimates are compared to to track healing progress. According to various embodiments, estimation of the initial volume of the wound site 114 at step 1102 may be performed according to (or as) step 616 of method 600 described with reference to FIGS. 6A-6G.

At step 1104, the estimated volume of the wound site 114 is determined and recorded at one or more additional times during treatment (e.g., once per day) following the estimation of the initial wound site 114 volume at step 1102, with the times at which such one or more wound site 114 volumes are estimated and the values of the determined wound site 114 volume being stored as data points within the memory of therapy device 102 and/or presented to a user as an output of therapy device 102 (e.g., via communications interface 124 or user interface 126). In some embodiments, the estimated wound volume can be plotted as a function of time.

The additional wound site 114 volume estimates determined at one or more additional times over the course of treatment at step 1104 may be estimated according to any number of different processes. For example, according to some embodiments, the wound site 114 volume estimates recorded at step 1104 may be based on the final dead space volume at the wound site 114 calculated, e.g., at step 508 of method 500 and/or using method 900 as described with reference to FIG. 5 and or 9A-9E, respectively.

As shown at step 510 of FIG. 5 and step 616 of FIG. 6A, according to some embodiments, the wound site 114 volume estimates at steps 1102 and/or steps 1104 may be performed in conjunction with method of delivering of installation fluid 105 to the wound site 114. However, as will be understood, according to other embodiments the determination of and recording of some, all, or none of the wound site 114 volume estimates at steps 1102 and/or steps 1104 may be performed independent of any delivery of installation of installation fluid 105 to the wound site 114.

As additional wound site 114 volume estimates are obtained at steps 1104, at step 1106, changes in the estimated wound site 114 volumes over time may be used to determine healing progression of the wound site 114. For example, step 1106 may include comparing wound site 114 volume estimates obtained at step 1104 to one or more previous estimates of the wound site 114 volume (obtained at either step 1104 or step 1102) to identify a change in the wound site 114 volume. In some embodiments, step 1006 may additionally include determining a rate at which the wound site 114 is healing based on the changes in the estimated wound site 114 volume over time. In some embodiments, step 1106 may include extrapolating or predicting a time at which wound site 114 will be fully healed based on the series of wound site 114 volume estimates stored by the controller 118. For example, step 1106 may include predicting a time at which the estimated wound site 114 volume will reach zero (or another threshold value) based on the initial wound site 114 volume estimate obtained at step 1002 and the series of additional wound site 114 volume estimates obtained at step 1004.

According to some embodiments, instead of, or in addition to, a calibrated leak system 113 being provided which is located upstream of the tubing valve 111, the NPWT system 100 may include a calibrated leak system 113 located downstream of the tubing valve 111. In general, such embodiments in which a calibrated leak system 113 is located downstream of the tubing valve 111 may operate in a manner substantially similar to the various methods described with reference to FIGS. 1-11. However, in contrast to the step of monitoring the pressure decay within the removed fluid canister circuit 202, determining a volume of the removed fluid canister circuit 202 based on the monitored pressure decay, and subsequently using the determined volume of the removed fluid canister circuit 202 to calculate wound site 114 volume, in the method 1200 of FIG. 12, pressure decay is instead monitored within the wound site circuit 204, with the determined volume of the wound site circuit 204 subsequently being used to calculate the dead space 103 in the removed fluid canister 106.

Figure 12:
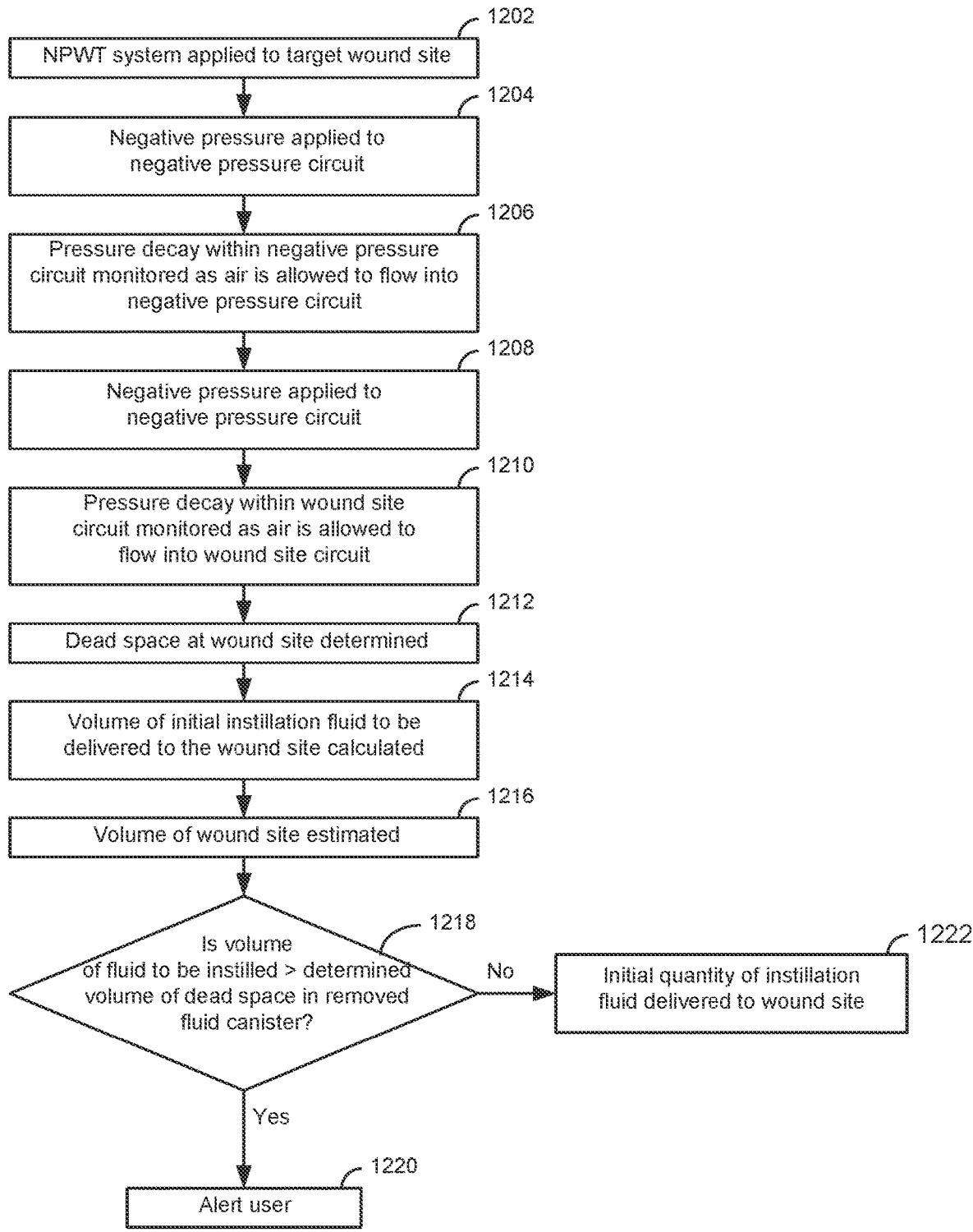
FIG. 12 is a flowchart of a method of instilling an initial quantity of fluid to a wound site using the negative pressure wound therapy system, according to an exemplary embodiment.

For example, referring to FIG. 12, a flowchart detailing the steps of a method 1200 for an initial set up of NPWT system 100 and delivery of an initial amount of installation fluid 105 to a wound site 114 is shown according to one embodiment in which a calibrated leak system 113 of the NPWT system 100 is positioned downstream of the tubing valve 111. In general, steps 1202, 1204 and 1206 of the embodiment of the method 1200 of FIG. 12 may be performed in a manner substantially similar to that as described with reference to steps 602, 604 and 606 of the method 600 of FIG. 6A.

At step 1208, the controller 118 is configured to initiate operation of the pump 120 to apply a second negative pressure (which may be equal to or different from the negative pressure applied by the controller 118 at step 1204) to the negative pressure circuit 200. According to various embodiments, the installation tubing valve 109 and the vent valve 113b may be configured to be set to closed configurations during the application of negative pressure to the negative pressure circuit 200 at step 1208. In embodiments in which a controller 118 controlled tubeset module 300 is used, the controller 118 may be configured to instruct the tubeset module 300 to effectuate the closing of the installation tubing valve 109 and/or the vent valve 113b.

At step 1210, following the attainment of the desired second negative pressure within the negative pressure circuit 200 (as, e.g., measured and reported to the controller 118 by pressure sensor 115a and/or pressure sensor 115b), the tubing valve 111 is closed so as to define a wound site circuit 204, the operation of the pneumatic pump 120 is stopped, and air from the ambient environment surrounding the therapy device 102 is allowed to flow through the vent 113a of the and into the wound site circuit 204. As air from the ambient environment flows into the wound site circuit 204, parameters related to the flow of air through the vent 113a and into the wound site circuit 204 are monitored, with the measured parameters subsequently being used by the controller 118 to calculate the volume of the wound site circuit 204 at step 1212. According to various embodiments, the parameters related to the flow of air into wound site circuit 204 may include, e.g., the rate of flow of air into the wound site circuit 204 (as measured, e.g., by flow detector 113c), the duration of time required for pressure within the wound site circuit 204 to increase to a predetermined pressure (e.g. ambient pressure) following the opening of the vent 113a and/or ceasing operation or the pump 120 at step 1210, the pressure (as, e.g., measured by pressure sensor 115b) within the wound site circuit 204 as the pressure increases from the negative pressure applied at step 1208 to the predetermined pressure; etc.

At step 1212, the controller 118 may be configured to determine the volume of the wound site circuit 204 based on the parameters measured during step 1208. According to some embodiments, the controller 118 may base this wound site circuit 204 volume calculation on stored relationships between various measured parameter values and corresponding volumes. These relationships between measured parameter measurements and corresponding volumes that are stored by the controller 118 may include various functions, models, lookup table, etc., and may be based on pre-existing information input and stored by the controller 118, or on information obtained and processed by the controller 118 during an optional, initial training procedure conducted by the controller 118 prior to the use of the NPWT system 100 to treat wound site 114 (e.g. prior to the initiation of method 500; as part of the initial setup and initial installation of installation fluid of step 502; etc.). One non-limiting examples of embodiments of training procedures by which such relationships may be generated by the controller 118 are outlined in related, U.S. Provisional Application 62/650,132, filed Apr. 17, 2018 and titled WOUND THERAPY SYSTEM WITH WOUND VOLUME ESTIMATION, the entire disclosure of which is incorporated by reference herein.

Using the determined volume of the wound site circuit 204, the controller 118 may determine the volume of the dead space 119 at the wound site 114 (i.e. the portion of the interior space defined between the wound site 114 and the lower surface of the drape layer 117 that is not occupied by the wound dressing 112 and/or any installation fluid 105/ other fluid) by subtracting or otherwise adjusting the calculated volume of the wound site circuit 204 to account for/factor in the known volumes of the downstream tubing portion 110b and the portion of the downstream instillation tubing 108b extending between the drape layer 117 and the instillation tubing valve 109 into the determination of the volume of the dead space 119 at the wound site 114.

At step 1214, an initial quantity of instillation fluid 105 that is to be delivered to the wound site 114 is calculated. According to various embodiments, the calculated initial quantity of instillation fluid 105 that is delivered to the wound site 114 may be based on the volume of the dead space 119 calculated by the controller 118 at step 1212. For example, in some embodiments, the controller 118 may calculate the initial volume of instillation fluid 105 to be delivered to the wound site 114 by multiplying the volume of dead space 119 calculated at step 1212 by a fluid instillation factor. The fluid instillation factor may be equal to or less than one (i.e., between zero and one) such that the volume of instillation fluid 105 delivered to the wound site 114 does not exceed the available space within the drape layer 117 (thereby minimizing inadvertent leakage from the wound dressing 112/drape layer 117. In some embodiments, the fluid instillation factor is between approximately 0.2 and approximately 0.8. However, it is contemplated that the fluid instillation factor can have any value in various alternative embodiments.

As noted previously with reference to step 510, in addition to being used to calculate a quantity of instillation fluid 105 to be delivered during any stage of treatment using NPWT system 100 and under any number of different conditions (e.g. allowing for the calculation of additional instillation fluid 105 to be delivered at step 516 even if the removed fluid canister 106 has been emptied, or entirely replaced with a different sized removed fluid canister 106 during the course of treatment), in some embodiments the NPWT system 100 may be additionally, or alternatively, used to monitor and track the progress of healing of the wound site 114 over time. Accordingly, in some embodiments, at step 1216, an initial baseline wound site 114 volume estimate may optionally be determined (via, e.g., a method as described with regards to FIG. 11) and stored by the controller 118, which may be used as a reference point against which future wound site 114 volume estimates may be compared to track healing progression of the wound site 114.

At step 1218 the dead space 103 of the removed fluid canister 106 may be calculated to determine whether the dead space within the removed fluid canister 106 will be sufficient to collect any fluids 121 from the wound site 114 (including non-absorbed instillation fluid 105) following the delivery of instillation fluid 105 at step 516. As will be understood, in embodiments in which the NPWT system 100 has not been operated prior to the use of the NPWT system 100 at step 1202, the volume of the removed fluid canister 106 should be empty, such that the dead space 103 of the removed fluid container 106 should be equal to the volume of the removed fluid canister 106.

The dead space 103 of the removed fluid container may be calculated by subtracting the known volumes of conduit 136 and the upstream tubing portion 110a from a volume of the removed fluid canister circuit 202 determined by subtracting the volume of the wound site circuit 204 calculated at step 1212 from a determined volume of the negative pressure circuit 200. As will be understood, the volume of the negative pressure circuit 200 may be determined in a manner similar to the method via which the volume of the wound site circuit 204 is determined at step 1212.

Similar to step 514, at step 1220 an alarm may be presented to a user if the initial volume of instillation fluid 105 to be delivered calculated at step 1214 exceeds the dead space 103 of the removed fluid canister 106. Otherwise, if the volume of the initial instillation fluid 105 to be delivered does not exceed the dead space 103 of the removed fluid canister 106, the calculated instillation fluid 105 is delivered to the wound site 114 at step 1222.

As will be understood, in some NPWT system 100 embodiments in which a calibrated leak system 113 is provided both upstream and downstream of the tubing valve 111, the NPWT system 100 may be operated to estimate wound site 114 volume and/or estimate dead space 103 at the removed fluid canister 106 according to a method that is the same as or similar to the method 600 of FIG. 6A or a method that is the same as or similar to the method 1200 of FIG. 12.

In other embodiments of NPWT system 100 in which both an upstream and downstream calibrated leak system 113 are provided, the NPWT system 100 may be operated to estimate wound site 114 volume and/or estimate dead space 103 at the removed fluid canister 106 according to a method that is the same as or similar to the method 600 of FIG. 6A and a method that is the same as or similar to the method 1200 of FIG. 12. For example, according to some embodiments, a modified method of operating a NPWT system 100 having both upstream and downstream calibrated leak systems 113 may include the steps of: monitoring pressure decay within the negative pressure circuit 200 (such as, e.g., described with reference to step 606 of the method 600 of FIG. 6 and/or step 1206 of the method 1200 of FIG. 12); monitoring pressure decay within the removed fluid canister circuit 202 (such as, e.g., described with reference to step 610 of the method 600 of FIG. 6); and monitoring pressure decay within the wound site circuit 204 (such as, e.g., described with reference to step 1210 of the method 1200 of FIG. 12).

In such embodiments, the determination of wound site 114 volume based on direct measurement (e.g. using the method 1200 of FIG. 12) may be compared to wound site 114 volume calculated based on indirect measurement (e.g. using the method 600 of FIG. 6A) and the determination of dead space 103 at the removed fluid canister 106 based on direct measurement (e.g. using the method 600 of FIG. 6A) may be compared to dead space 103 volume calculated based on indirect measurement (e.g. using the method 1200 of FIG. 12). The controller 118 in such embodiments may be configured to generate an alarm or alert in response to a discrepancy between the direct and indirect measurements of wound site 114 volume and/or dead space 103 at the removed fluid canister 106. By providing such redundancy to the wound site 114 and/or removed fluid canister 106 dead space 103 calculations, such embodiments may be configured to allow the NPWT system 100 to provide more accurate and reliable results.

As will be understood, according to various embodiments, the controller 118 may be programmed to allow the NPWT system 100 to determine volume relative to the wound site 114 using any or all of the methods described herein. Accordingly, while in some embodiments the controller 118 may optionally be preprogrammed to automatically determine a volume of instillation fluid 105 to be delivered according to a particular method (e.g. the method 900 embodiment illustrated in FIGS. 9A-9E), the controller 118 may optionally also allow a user to select any of the other modes of calculating a volume relative to the wound site 114 based on whether the user desires to, e.g.: remove fluid 121 from the wound site 114 prior to instillation of additional instillation fluid 105; verify sufficient dead space 103a in the removed fluid canister 106 prior to determining the dead space at the wound site 114; verify sufficient dead space 103b in the removed fluid canister 106 prior to the instillation of a calculated quantity of additional instillation fluid 105 to be delivered to the wound site 114; monitor changes in the wound site 114 volume to track healing progression; etc.

Tubeset Module

Although in some arrangements, some or all of the calibrated leak system 113, tubing valve 111 and/or the instillation tubing valve 109, or other NPWT system 100 components may be configured to be manually operated/actuated/utilized by a user, as noted above, according to various embodiments, some or all of these components may alternatively be configured to be operated/actuated/utilized by the controller 118, without requiring any user assistance to do so. In such a manner, implementation of the system for/method of determining a volume of instillation fluid to be delivered to a wound site, estimating a volume of a wound, monitoring healing progression of a wound, and/or other use of the NPWT system 100 may be fully automated using the controller 118, allowing for easier use of the NPWT system 100.

By providing the NPWT system 100 with an automated manner via which controller 118 may control or otherwise interact with one or more of the calibrated leak system 113, tubing valve 111, instillation tubing valve 109, and/or other component(s) of the NPWT system 100, the tubeset module 300 may increase the accuracy of the NPWT system 100. For example, in light of the ability of the controller 118 to utilize the tubeset module 300 to independently actuate (i.e. without user intervention) the operation of the calibrated leak system 113, the tubing valve 111 and/or the instillation tubing valve 109 elements, the controller 118 may be configured to increase the rate at which data related to instillation fluid volume estimation, wound site volume estimation, wound site 114 healing progression monitoring, and/or other functions of the NPWT system 100 is gathered. By increasing the data points used to provide such information, the reliability of the information provided by the controller 118 may thereby be increased. Similarly, the obviation or minimization of user involvement provided by the tubeset module 300 may facilitate (and thereby increase the likelihood of) the usage of a dual calibrated leak system 113 arrangement as described with reference to FIG. 12 above, thus also increasing the reliability of the NPWT system 100.

In general, the tubeset module 300 comprises a housing element 304 containing a power source 301, a communications interface 302, and one or more actuatable elements 303 configured to be controlled by the controller 118. In some embodiments, the tubeset module 300 may optionally also comprise one or more additional non-actuatable elements 305, such as, e.g., pressure sensor 115a and/or pressure sensor 115b. According to embodiments in which calibrated leak system 113 is not defined by a vent valve 113b and only comprises a non-actuatable vent 113a, the non-actuatable element(s) 305 may comprise such a calibrated leak system 113 formed without a vent valve 113b.

As will be understood, according to some embodiments, some or all of the actuatable elements 303 may be configured so as to be self-actuating. In some such embodiments, the actuatable element 303 may comprise an internal actuator that is in operably connected (via a wired, wireless, or any other type of connection) to the power source 301 and/or communications interface 302 of the tubeset module 300, via which instructions received from the controller 118 and/or power are relayed to the actuator of the actuatable element 303. In other such embodiments, such self-actuation actuatable element 303 may individually comprise one or both of a power source and/or communications interface (in addition to the power source 301 and/or communications interface 302 of the tubeset module). In such embodiments, the instructions from the controller 118 may be received directly by the communication interface of the actuatable element 303 from the controller, or may be received indirectly by the communication interface of the actuatable element 303 from the communication interface 302 of the tubeset module 300. In other embodiments, some or all of the actuatable elements 303 may be configured to be actuated by any number of different types of, or combinations of known actuators that are contained by the housing element 303, with the actuators of the housing element 303 being configured to effectuate actuation of the one or more actuatable elements 303 in response to instructions received from the controller 118.

The power source 301 may comprise any number of, and combination of, sources of energy that are configured to supply sufficient energy to the communications interface 302, actuatable element(s) 303 and/or non-actuatable elements 305 contained by the housing element 304 as required for operation of the NPWT system 100. In some embodiments in which some or all of the tubeset module 300 is integrated into the therapy device 102, the power provided by the power source 301 of the housing element 304 may comprise a power source of the therapy device 102.

The communications interface 302 may comprise any number of, and combination of, wired and/or wireless connections via which the tubeset module 300 may receive communications (such as, e.g., actuation signals) from the controller 118. According to some embodiments, the communications interface 302 may optionally also be configured to send information to and/or receive information from the controller 118, other tubeset module 300 housing elements 304 (such as, e.g., information regarding the status of the one or more actuatable elements 303 and/or non-actuatable elements 305 of the tubeset module 300), and/or other sources. In some embodiments in which some or all of the tubeset module 300 is integrated into the therapy device 102, the communications interface 302 of the housing element 304 may be defined by a portion of a communications interface of the therapy device 102.

According to some arrangements, tubeset module 300 may be defined by a single housing element 304, with each of actuatable elements 303 (e.g. upstream and/or downstream calibrated leak system 113, tubing valve 111 and/or the instillation tubing valve 109, etc.) and/or non- actuatable elements 305 that are to be controlled/utilized by the controller 118 forming a part of the single, integral housing element 304. In other embodiments, the tubeset module 300 may be defined by a plurality of separate and distinct housing elements 304, with each housing element 304 formed with one or more of the various actuatable elements 303 and/or non-actuatable element 305 that are to be controlled/utilized by the controller 118.

According to various arrangements, the one or more housing elements 304 defining the tubeset module 300 may be provided as a separate, discrete, individual component of the NPWT system 100, which may subsequently be attached to or otherwise incorporated into one or more of the other components of a new or existing NPWT system 100. In other arrangements, some or all of the one or more housing elements 304 defining the tubeset module 300 may be provided as an integrated part of one or more of the other components of the NPWT system 100.

For example, in some arrangements, some or the entirety of the tubeset module 300 may be integrated into the wound dressing 112, with the portion of the tubeset module 300 provided with the wound dressing 112 being configured to be removed from the NPWT system 100 with the removal of the wound dressing 112. Upon removal of the integrated wound dressing 112/tubeset module 300, the entire wound dressing 112/tubeset module 300 may be disposed of. Alternatively, the tubeset module 300 may be removed from the wound dressing 112 prior to disposal of the wound dressing 112 and optionally reused with another wound dressing 112 and/or other NPWT system 100 component.

In other arrangements, some or the entirety of the tubeset module 300 may be integrated into the removed fluid canister 106, with the portion of the tubeset module 300 provided with the removed fluid canister 106 being removed from the NPWT system 100 with the removal of the of the removed fluid canister 106 from the NPWT system 100. In some such embodiments, the tubeset module 300 may be monolithically formed with the removed fluid canister 106, while in other embodiments; the tubeset module 300 may be non-integrally formed with the removed fluid canister 106.

According to another arrangement, the tubeset module 300 may be configured to be integrated in-line with one or both of the tubing 108 and/or 110. In such embodiments, attachment adapters 400 may be provided on one or both of the tubeset module 300 and/or tubing 108 and/or 110 to facilitate a fluid tight attachment of the tubeset module 300 to the tubing 108 and/or 110. According to some embodiments, the attachment adapters 400 may be provided on the tubeset module 300, with the attachment adapters 400 being configured to be able to form a fluid tight attachment directly with one or both of the tubing 108 and/or 110, allowing NPWT systems formed without a tubeset module 300 and/or calibrated leak system 113, tubing valve 111 and/or the instillation tubing valve 109 to be retrofitted with a tubeset module 300 so as to provide a NPWT system 100 as disclosed herein.

In some arrangements, some or the entirety of the tubeset module 300 may be integrated into the housing of the therapy device 102. In such embodiments, the efficiency of using the NPWT system 100 may be increased, as by incorporating a tubeset module 300 including some or all of the calibrated leak system 113, tubing valve 111 and/or the instillation tubing valve 109 into the housing of the therapy device 102, the time to setup the NPWT system 100 may be reduced as compared to the time that would otherwise be required to setup up a NPWT system 100 in which some or all of the calibrated leak system 113, tubing valve 111 and/or instillation tubing valve 109 were provided as separate and discrete components of the NPWT system 100. Additionally, by incorporating the tubeset module 300 into the housing of the therapy device 102, a NPWT system 100 as described herein may be provided irrespective of the particular tubing, removed fluid canister, wound dressing, or other component(s) that are provided to define a NPWT system 100 for treatment of a wound site 114.

Referring to FIGS. 13-16, various embodiments of a tubeset module 300 configured to allow for partially or fully automated control of the NPWT system 100 using the controller 118 are shown. As will be understood, although reference has been made to the controller 118 being provided as part of the therapy device 102, it is to be understood that, according to various arrangements, the controller 118 may be provided separate and remote from the therapy device 102 and/or NPWT system 100 (e.g., by a remote medical provider). In such embodiments, the remotely provided controller 118 may be configured to communicate directly with the tubeset module 300 and/or indirectly with the tubeset module 300 via a communications interface provided by the therapy device 102.

Figure 13:
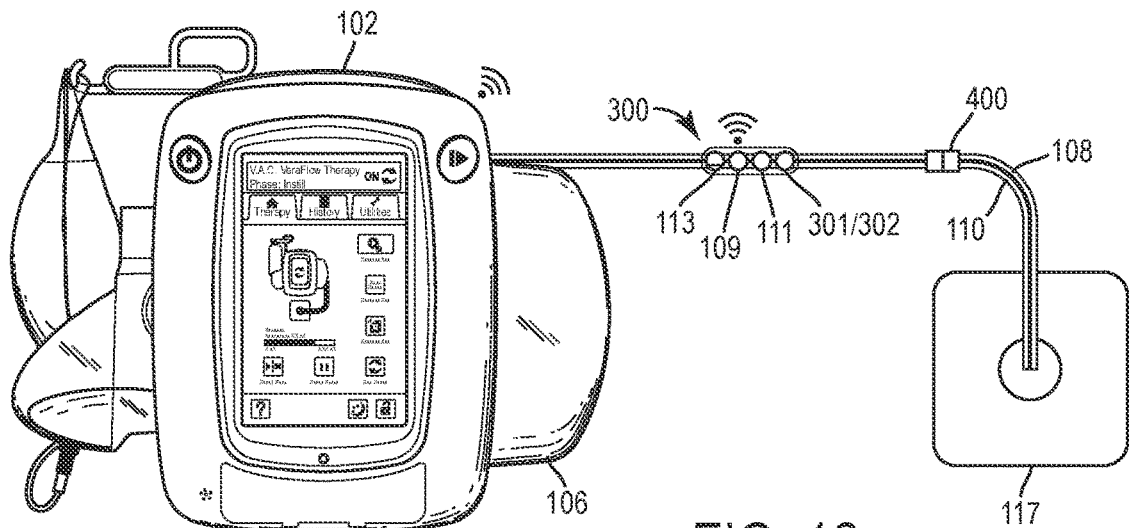
FIG. 13 illustrates a negative pressure wound therapy system including a tubeset module, according to an exemplary embodiment.

As illustrated by the NPWT system 100 embodiment of FIG. 13, in some arrangements, the tubeset module 300 is provided as a single, integrated housing element 304 containing actuatable elements 303 comprising a calibrated leak system 113, a tubing valve 111 and an optional instillation tubing valve 109. According to some embodiments, one or both of the tubing valve 111 and the optionally provided instillation tubing valve 109 may comprise the same or distinct clamps. As shown in FIG. 13, also contained within the housing element 304 is a power source 301 configured to actuate the actuatable element 303 in response to instructions being received from the controller 118 via the communications interface 302.

Although in the embodiment illustrated in FIG. 13 a single, integral tubeset module 300 is shown as being in-line with both tubing 108 and tubing 110, according to other arrangements (now shown) it is to be understood that a first housing element 304 comprising the calibrated leak system 113 and a tubing valve 111 may be provided in-line with tubing 110, while an optional, second housing element 304 comprising instillation tubing valve 109 may be provided in-line with tubing 110.

As illustrated by the NPWT system 100 of FIG. 13, in some embodiments, the tubeset module 300 may be formed integrally with upstream tubing portion 110a and/or upstream instillation tubing 108a. According to some such embodiments, the upstream tubing portion 110a and/or upstream instillation tubing 108a with which the tubeset module 300 is integrally formed may in turn be formed integrally with the therapy device 102. In such embodiments, the tubeset module 300 is configured to be removably attached to the downstream tubing portion 110b and/or downstream instillation tubing 108b formed integral with the wound dressing 112, such that following use of the NPWT system 100 with a first wound dressing 112, the therapy device 102 with integrated upstream tubing portion 110a and/or upstream instillation tubing 108a and tubeset module 300 may be reused with a new, second wound dressing 112. In other embodiments, such as, e.g., illustrated by the NPWT system 100 of FIG. 14, some or all of the tubeset module 300 may alternatively be formed integrally with the wound dressing 112, with the tubeset module 300 being configured to be removed from the NPWT system 100 with the removal of the wound dressing 112.

Figure 14:
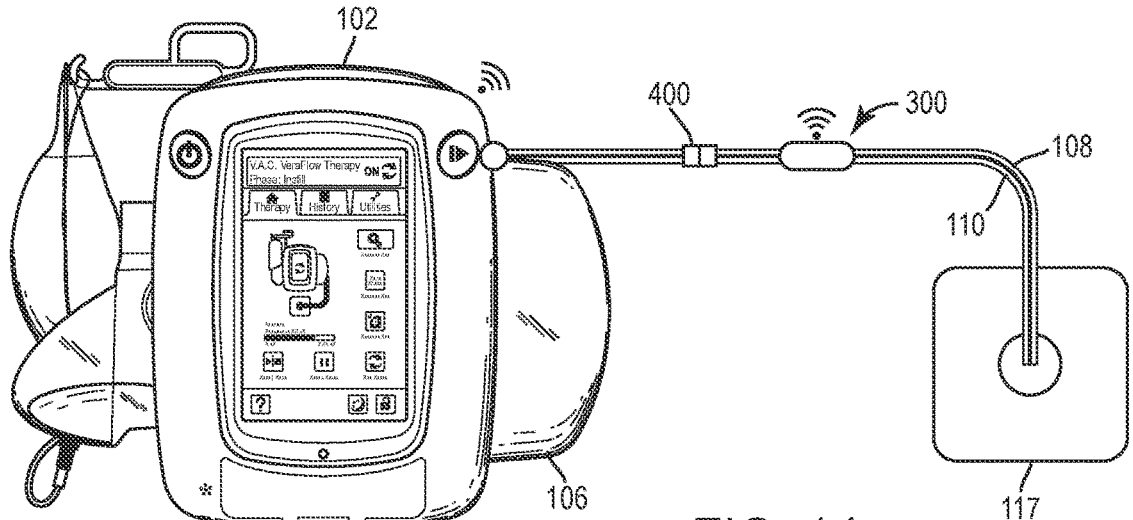
FIG. 14 illustrates a negative pressure wound therapy system including a tubeset module, according to an exemplary embodiment.
Figure 15:
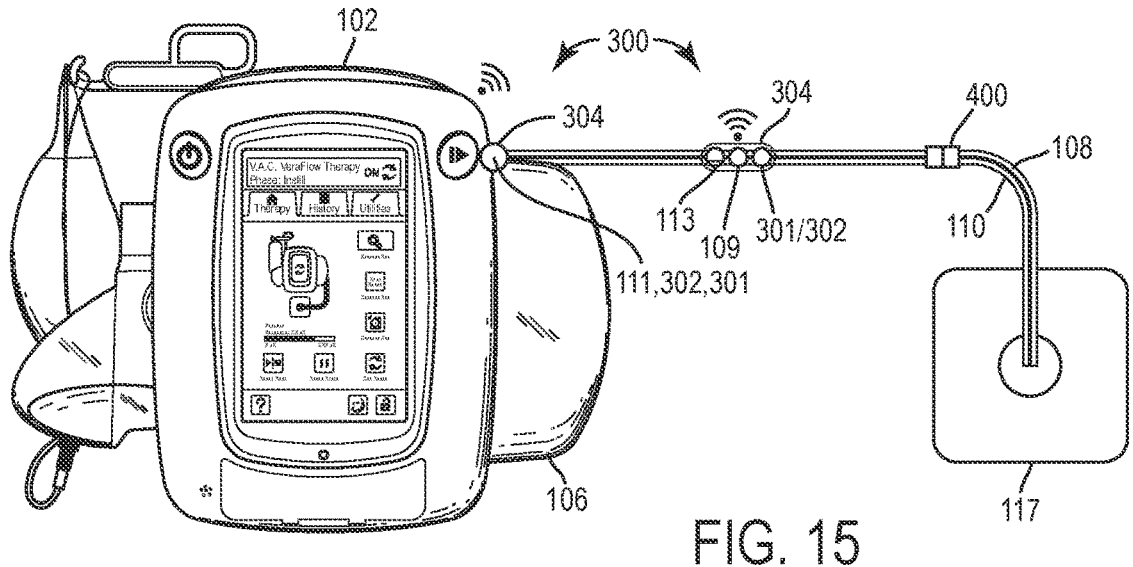
FIG. 15 illustrates a negative pressure wound therapy system including a tubeset module, according to an exemplary embodiment.

Referring to the NPWT system 100 of FIG. 15, according to some embodiments, the tubeset module 300 may comprise a first housing element 304 containing a calibrated leak system 113 and an optional instillation tubing valve 109, pressure sensor 115a and/or pressure sensor 119 positioned in-line with the tubing 108 and/or 110. A second housing element 304 comprising a tubing valve 111 may be spaced from the first housing element 304. As shown in FIG. 14, according to some arrangements, the second housing element 304 may be integrated into the removed fluid canister 106. In other embodiments, the second housing element 304 may alternatively be incorporated into the therapy device 102, or may be provided at a second location in-line with the tubing 110.

Figure 16A:
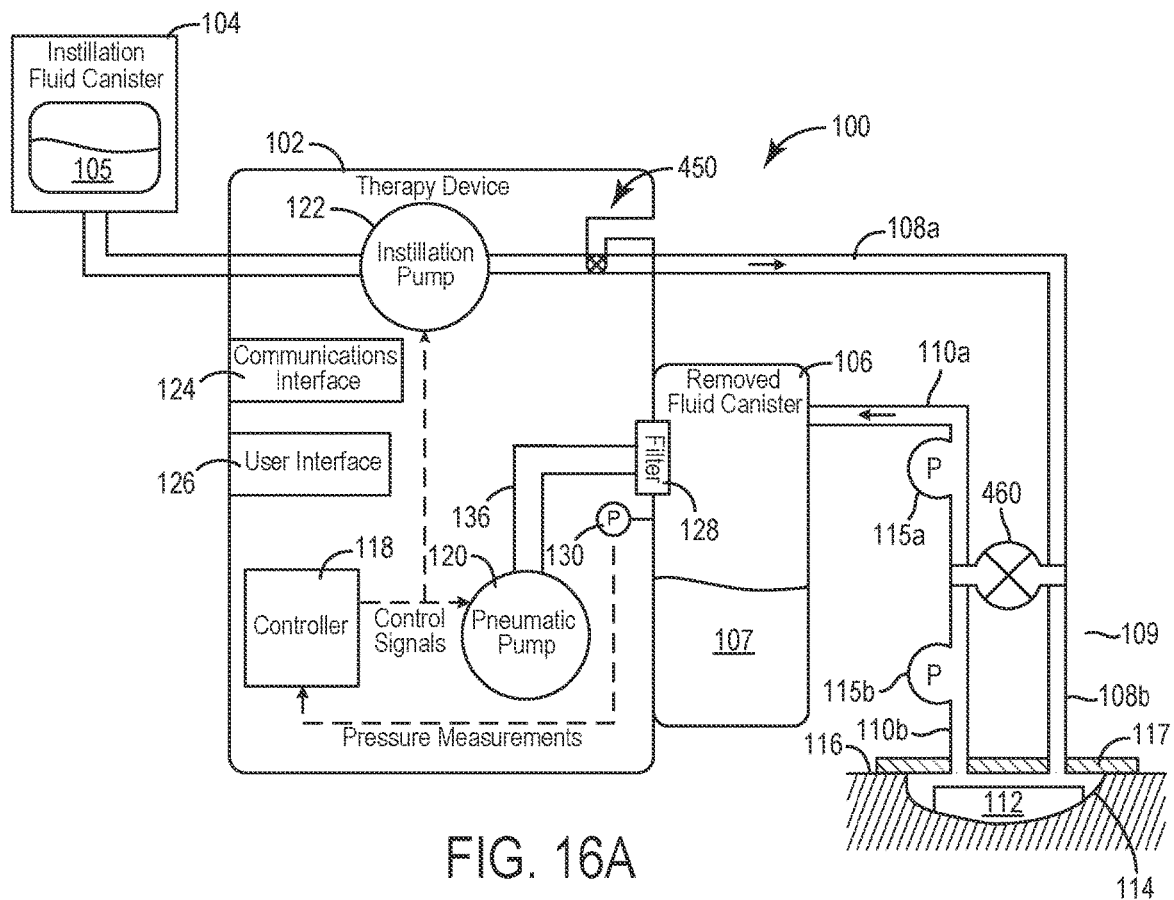
FIG. 16A is a block diagram of a negative pressure wound therapy system including a tubeset module, according to an exemplary embodiment.

Referring to FIG. 16A, a block diagram of a NPWT system 100 according one embodiment is shown. As illustrated by the NPWT system 100 of FIG. 16A, according to some embodiments, fluid communication between some or all of the negative pressure circuit 200 and the ambient environment may be provided by a purge valve system 450 provided along the installation tubing 108 as an alternative to, or in addition to, calibrated leak 113. According to various embodiments, the purge valve system 450 may comprise a structure similar to that of calibrated leak system 113 (including calibrated leak system 113 embodiments comprising any combination of vent 113a, vent valve 113b and/or flow detector 113c components).

As also illustrated by FIG. 16A, in such NPWT system 100 embodiments, the tubing valve 111 and/or installation tubing valve 109 may be replaced by a valve assembly 460 that is fluidly attached to the tubing 110 at a junction between the upstream tubing portion 110a and downstream tubing portion 110b and that is attached to the installation tubing assembly at a junction between the upstream tubing 108a and downstream tubing 108b, and which is actuatable to a variety of positions. In a first position, the valve assembly 460 may permit fluid flow from the pneumatic pump 120 to the wound site 114 via tubing 110 and from the installation pump 104 to the wound site 114 via installation tubing 108. In a second position, the valve assembly 460 may permit fluid flow from the pneumatic pump 120 to the wound site 114 via tubing 110 while blocking fluid flow from the installation pump 104 to the wound site 114 via installation tubing 108. In a third position, the valve assembly 460 may block fluid flow from the pneumatic pump 120 to the wound site 114 via tubing 110 while permitting flow from the installation pump 104 to the wound site 114 via installation tubing 108. In a fourth position, the valve assembly 460 may fluidly connect the upstream tubing portion 110a with the upstream installation tubing 108a, resulting in the isolation of the downstream tubing portion 110b, the downstream tubing 108, and the wound dressing 112 from the remained of the therapy device 102.

When in the first configuration, the valve assembly 460 defines a negative pressure circuit 200 is defined by the tubing 136, the fluid canister 106, the tubing 110, the wound site 114 and the portion of the installation tubing extending between the wound site 114 and the purge valve 450. When in the fourth configuration, the valve assembly 460 defines a removed fluid canister circuit 202 is defined by the tubing 136, the fluid canister 106, the upstream tubing portion 110a, and the portion of the upstream tubing 108a extending between the valve assembly 460 and the purge valve 450 and a wound site circuit 204 defined by the downstream tubing portion 110b, the wound site 114, and the downstream tubing 108b.

As will be understood, the valve assembly 460 and the purge valve 450 of the NPWT system 100 of FIG. 16A may be operated in a manner similar to the operation of the tubing valve 111, calibrated leak, and/or installation tubing valve 109 as described with reference to any of the methods described herein for determining wound site volume, estimating a volume of fluid to be instilled, monitoring wound healing progression, or performing any other functions using the NPWT system 100.

Figure 16B:
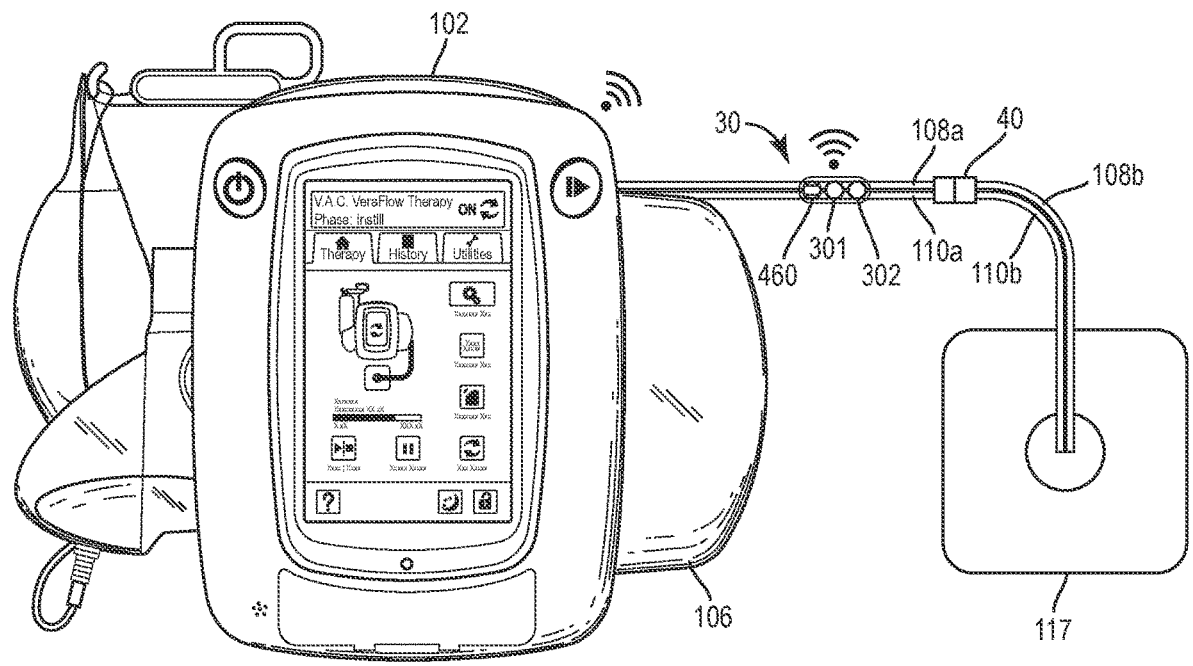
FIG. 16B illustrates the negative pressure wound therapy system comprising a tubeset module of FIG. 16A, according to an exemplary embodiment.

Referring to FIG. 16B, a tubeset module 300 configured for used with a NPWT system 100 incorporating a purge valve 450 (such as, e.g. shown in FIG. 16A) is shown according to one embodiment. As illustrated by FIG. 16B embodiments in which the purge valve 450 is provided as a discrete component of the therapy device 112 capable of being automatically actuated by the controller 118, the tubeset module 300 may comprise only a single actuatable element 303, defined by valve assembly 460. As will be understood, in other embodiments, (such as, e.g. where the purge valve 450 provided as part of the therapy device is not automatically actuatable by the controller 118), the purge valve 450 may be provided as a part of a tubeset module 300 that is partially or entirely integrated into the therapy device 112.

Although in the NPWT system 100 embodiment illustrated in FIG. 16A the pure valve 450 is illustrated as being provided as part of the therapy device 112, according to other embodiments, the purge valve 450 may be alternatively, or additionally, provided as a part of the upstream tubing 108a. In such embodiments, the purge valve 450 may accordingly be provided as an actuatable element 303 of the tubeset module 300.

As will be understood, the controller 118 may be configured to effectuate any number of different operations using the NPWT system 100 based on the selective, fully automated actuation of/interaction with some or all of the actuatable elements 303 and/or non-actuatable elements 305 of a tubeset module 300 according to any number of different methods and protocols. According to various embodiments, the order and/or combination of instructions transmitted by controller 118 to the tubeset module 300 and/or the information received by the controller 118 from the tubeset module 300 may be configured to automatically operate the tubeset module 300 in a manner that allows the controller 118 to automatically effectuate one or more of the methods 500, 600, 800, 900, 1000, 1100, 1200, etc. described herein.

Figure 17:
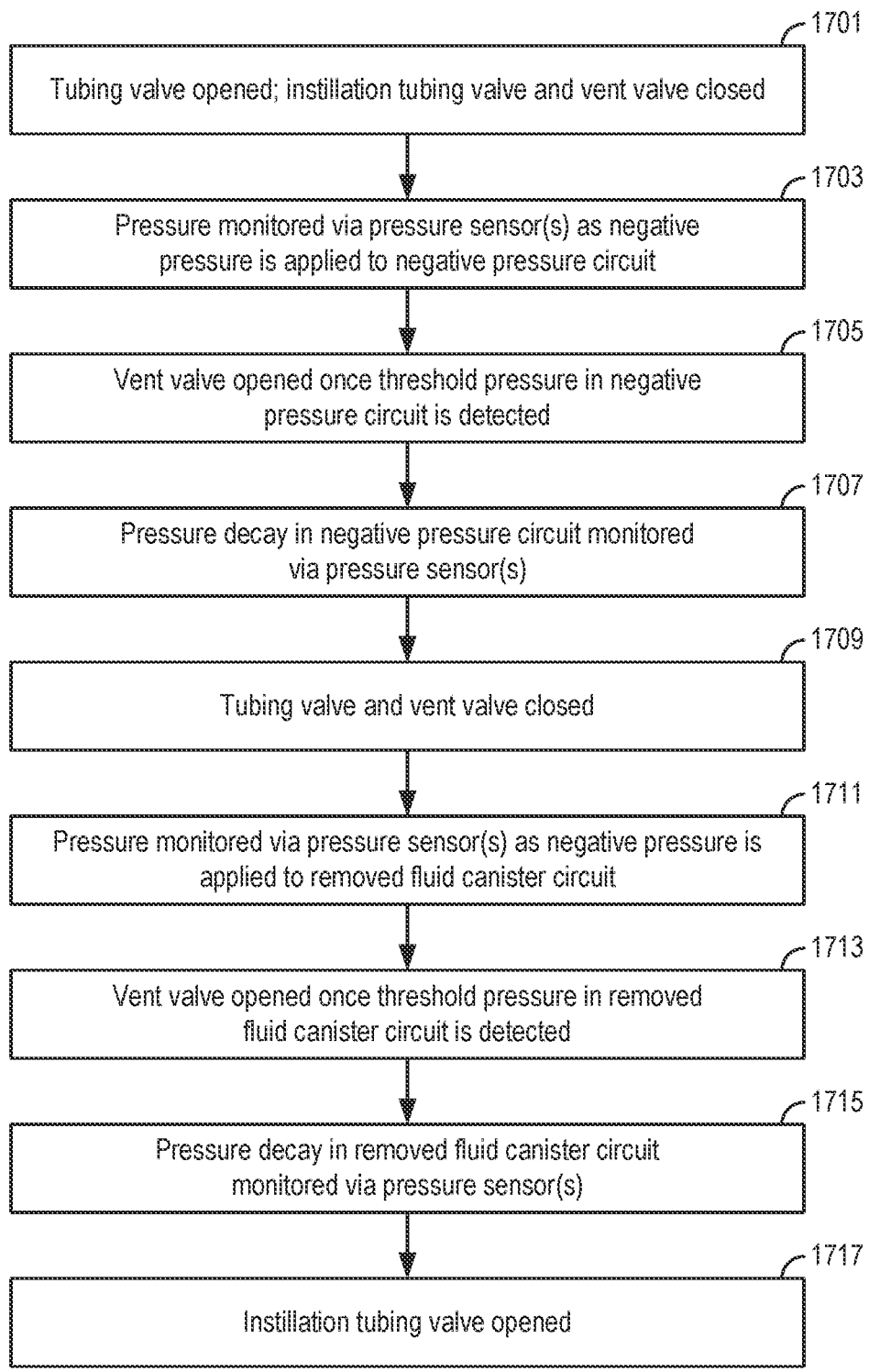
FIG. 17 is a flowchart of a fully automated method of operating a tubeset module, according to an exemplary embodiment.

Represented in FIG. 17 is one method 1700 via which the controller 118 may utilize a tubeset module 300 containing actuatable elements 303 comprising a tubing valve 111, installation tubing valve 109, and calibrated leak system 113 and non-actuatable element(s) 305 comprising one or both of pressure sensor 115a and/or pressure sensor 115b to automatically control the NPWT system 100 to determine dead space 119 at a wound site 114 according to a method such as, e.g., described with reference to the method 500 of FIG. 5 and the method 600 of FIG. 6A.

At step 1701, in response to the controller 118 being initiated to determine dead space at a wound site 114 (such as, e.g., at step 506 of the method 500 of FIG. 5), the controller 118 may initiate communication with the tubeset module 300 to confirm that the installation tubing valve 109 and vent valve 113b of the calibrated leak system 113 are closed, and that the tubing valve 111 is opened. If the installation tubing valve 109 and/or vent valve 113b are open, the controller 118 may instruct the tubeset module 300 to effectuate actuation of the installation tubing valve 109 and/or vent valve 113b into a closed configuration. Similarly, if the tubing valve 111 is detected by the controller 118 as being closed, the controller 118 may transmit instructions to the tubing valve 111 via the communications interface 302 to actuate opening of the tubing valve 111.

Once the controller 118 has received, via the communications interface 302, confirmation that the installation tubing valve 109 and vent valve 113b are closed and the tubing valve 111 is open, the controller 118 may be configured to initiate operation of the pneumatic pump 120 to apply negative pressure to the negative pressure circuit 200 (such as, e.g., described with reference to step 604 of the method 600 of FIG. 6A). During operation of the pneumatic pump 120, the controller 118 at step 1703 may be configured to receive from the pressure sensor 115a and/or pressure sensor 115b pressure readings corresponding to the pressure within the negative pressure circuit 200. As will be understood, the pressure readings received by the controller 118 at step 1703 may be received continuously, at predetermined intervals, and/or in response to specific requests for pressure readings transmitted by the controller 118 to the tubeset module 300 via communications interface 302.

In response to receiving pressure readings from the tubeset module 300 indicative of the pressure within the negative pressure circuit 200 having reached a threshold pressure, the controller 118 at step 1705 may be configured to stop operation of the pneumatic pump 120 and transmit to the tubeset module 300 an actuation signal configured to cause the opening of the vent valve 113b.

At step 1707, the controller 118 may be configured to receive from the pressure sensor 115a and/or pressure sensor 115b pressure readings corresponding to pressure decay within the negative pressure circuit 200, such as, e.g., described with reference to step 606 of FIG. 6A. The pressure readings received by the controller 118 at step 1707 may be received continuously, at predetermined intervals, or in response to specific requests for pressure readings transmitted by the controller 118 to the tubeset module 300 via communications interface 302.

Once the controller 118 has received pressure readings from the tubeset module 300 indicative of the pressure within the negative pressure circuit 200 having reach a threshold pressure (such as, e.g., ambient pressure), the controller 118 at step 1709 may be configured to effectuate, using the tubeset module 300, the actuation of the closing of the tubing valve 111 and the vent valve 113b in advance of the application of negative pressure to the resultant removed fluid canister circuit 202 (such as, e.g., during step 608 of the method 600 of FIG. 6A).

At step 1711, the controller 118 once again may be configured to receive pressure readings from the tubeset module 300. The pressure readings received by the controller 118 at step 1711 may be received continuously, at predetermined intervals, or in response to specific requests for pressure readings transmitted by the controller 118 to the tubeset module 300 via communications interface 302. In response to receiving pressure readings from the tubeset module 300 indicative of the pressure within the removed fluid canister circuit 202 having reached a threshold pressure, the controller 118 at step 1713 may be configured to stop operation of the pneumatic pump 120 and transmit to the tubeset module 300 an actuation signal configured to cause the opening of the vent valve 113b.

At step 1715, the controller 118 may be configured to receive from the pressure sensor 115a pressure readings corresponding to pressure decay within the removed fluid canister circuit 202, such as, e.g., described with reference to step 610 of FIG. 6A. The pressure readings received by the controller 118 at step 1715 may be received continuously, at predetermined intervals, or in response to specific requests for pressure readings transmitted by the controller 118 to the tubeset module 300 via communications interface 302.

According to some embodiments, following step 1715, at step 1717, the controller 118 may be configured to actuate, using the tubeset module 300, the opening of the instillation tubing valve 109, in advance of the instillation of instillation fluid to the wound site 114 (such as, e.g., described with reference to step 516 of the method 500 of FIG. 5 and/or step 622 of the method 600 of FIG. 6A).

Wound Therapy System with Internal Alternating Orifice

Figure 18:
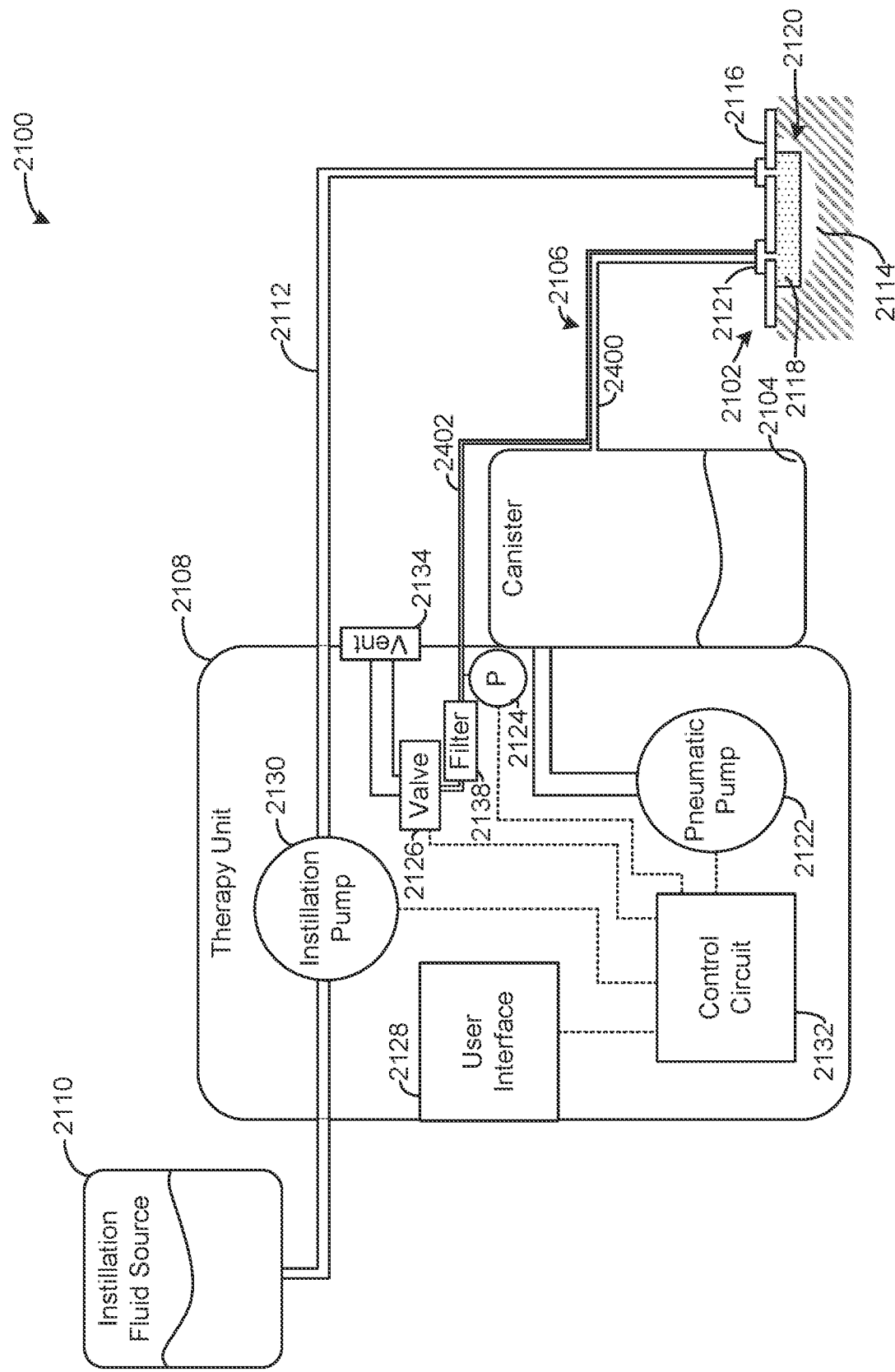
FIG. 18 is a block diagram of a negative pressure and instillation wound therapy (NPIWT) system, according to an exemplary embodiment.

Referring now to FIG. 18, an NPIWT system 2100 is shown, according to an exemplary embodiment. The NPIWT system 2100 includes a dressing 2102 fluidly communicable with a canister 2104 via first tubing 2106 and a therapy unit 2108 coupled to the canister 2104. As shown in FIG. 18, the NPIWT system 2100 also includes an instillation fluid source 2110 fluidly communicable with the dressing 2102 via the therapy unit 2108 and second tubing 2112. The NPIWT system 2100 and components thereof may correspond to, may be implemented with, may be combined, and/or may otherwise provide various features of the systems and methods described above with reference to FIGS. 1-17. It should be understood that the present disclosure contemplates various combinations of the embodiments shown in the drawings.

The dressing 2102 is shown as applied to a wound bed 2114. The dressing 2102 includes a drape 2116 sealed over the wound bed 2114 and a foam layer 2118 positioned between the drape 2116 and the wound bed 2114. In various embodiments, the dressing 2102 may include various layers and features. The drape 2116 may be made of a substantially air-impermeable material (e.g., a polyurethane-based material) and may include an adhesive border that allows the drape to be sealed to a patient's skin around the wound bed 2114. The foam layer 2118 may include a manifolding layer that allows airflow therethrough and facilitates the distribution of negative pressure across the wound bed 2114. A wound space 2120 that includes the open volume (i.e., through which air may flow) in the foam layer 2118 and otherwise situated between the drape 2116 and the wound bed 2114 is thereby established.

Figure 21:
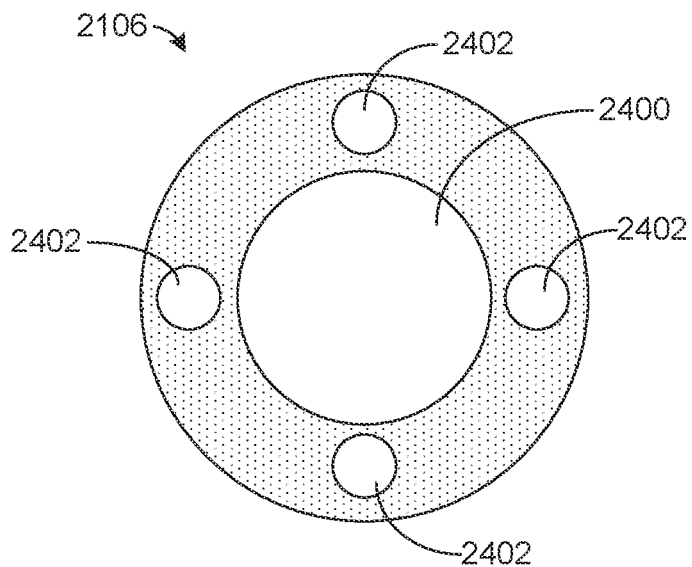
FIG. 21 is a cross-sectional illustration of tubing of the NPIWT system of FIG. 18, according to an exemplary embodiment.

The first tubing 2106 extends from the dressing 2102 to the canister 2104. A cross-section of the first tubing 2106 is shown in FIG. 21, according to an exemplary embodiment. As described in detail with reference to FIG. 21, the first tubing 2106 includes an inner lumen 2400 and one or more outer lumens 2402. The inner lumen 2400 provides for the flow of fluid from the wound space 2120 into the canister 2104. The one or more outer lumens 2402 are fluidly communicable with a pressure sensor 2124 to facilitate measurement of the pressure at the wound space 2120. The one or more outer lumens 2402 are also fluidly communicable with a valve 2126 as described below. It should be understood that, while described as inner and outer in the examples herein, any geometrical arrangement of multiple lumens may be used in various embodiments. A connection pad (e.g., low pressure interface) 2121 is coupled to the drape 116 and facilitates connection of the first tubing 106 to the dressing 2102.

The canister 2104 is configured to collect wound exudate (e.g., fluid, other debris) removed from the wound space 2120 via the first tubing 2106. The canister 2104 is fluidly communicable with the wound space 2120 via the first tubing 2106. The canister 2104, the first tubing 2106, and the dressing 2102 thereby define a sealed space that includes the wound space 120.

The therapy unit 2108 is coupled to the canister 2104 and includes a pneumatic pump 2122 fluidly communicable with the sealed space, a sensor 2124 configured and positioned to measure pressure in the sealed space, a valve 2126 positioned between the sealed space and an environment, a user interface 2128, and an instillation pump 2130 coupled to the second tubing 2112. The therapy unit 2108 also includes a control circuit 2132 communicably and operably coupled (e.g., capable of exchanging electronic signals with) the pneumatic pump 2122, the sensor 2124, the valve 2126, the user interface 2128, and the instillation pump 2130.

The pneumatic pump 2122 is controllable by the control circuit 2132 and operable to pump (e.g., draw, remove) air from the canister 2104, the first tubing 2106, and the wound space 2120 (i.e., from the sealed space). The pneumatic pump 2122 may thereby create a negative pressure in the sealed space relative to atmospheric pressure, for example between 25 mmHg and 175 mmHg. The pneumatic pump 2122 may create a pressure differential that causes fluid and debris to be drawn out of the wound space 2120, through the first tubing 2106, and into the canister 2104.

The sensor 2124 is positioned and configured to measure the pressure in the sealed space. As shown in FIG. 18, the pressure sensor 2124 is positioned to measure pressure via one or more outer lumens 2402. In other embodiments a sensor 2124 may be included to measure pressure elsewhere in the sealed space (e.g., in the canister 104). The sensor 2124 provides pressure measurements to the control circuit 2132 (e.g., digital values, analog signals). The control circuit 2132 may be configured to receive the pressure measurements from the sensor 2124 and use the pressure measurements in a control loop to generate control signals for the pneumatic pump 2122 that cause the pneumatic pump 2122 to maintain a desired pressure in the sealed space or provide a desired pattern of pressure in the sealed space.

The user interface 2128 may include a display screen, a touch screen, a speaker, a button, a switch, or any other element capable of providing information to a user or receiving input from a user. In some embodiments, the control circuit 2132 is configured to generate a graphical user interface and cause the graphical user interface to be displayed on the user interface 2128. The graphical user interface may include various information about the NPIWT provided by the NPIWT system 2100, for example relating to the pressure in the sealed space, an amount of instillation fluid to be provided, a schedule of negative pressure and instillation cycles, and/or a size of the wound space 2120. The user interface 2128 may allow a user to input commands and settings relating to the operation of the therapy unit 2108. The control circuit 2132 may receive such inputs from the user interface 2128 and control the therapy unit 2108 in accordance with the inputs.

The instillation pump 2130 is configured to cause instillation fluid to be transported from the instillation fluid source 2110 to the wound space 2120 via second tubing 2112. The instillation pump 2130 may be controllable by the control circuit 2132 to provide a desired amount of the instillation fluid to the wound space 2120, provide instillation fluid to the wound space 2120 at a desired rate, prevent instillation fluid from flowing to the wound space 2120, or otherwise control the flow of instillation fluid to the wound space 2120. The instillation pump may include a peristaltic pump or some other type of pump.

The valve 2126 is controllable between an open position and a closed position. As shown in FIG. 18, the valve 2126 is located at an interior of the therapy unit 2108 in pneumatic communication with a surrounding environment (e.g., ambient air) via a vent 2134 positioned along an exterior of the therapy unit 2108. The valve 2126 is also shown as communicable with the one or more outer lumens 2402 of the first tubing 2106. A filter 2138 is located between the canister 2104 and the pump 2122. When the valve 2126 is in the open position, air may flow between the surrounding environment and the sealed space via the filter 2138. When the valve 2126 is in the closed position, air is prevented from flowing therethrough. As shown in FIGS. 19-20 and described in detail with reference thereto, the valve 2126 may be a solenoid valve. In various other embodiments, other types of valves may be included. As described in detail below, the valve 2126 may be controllable to allow a sudden surge ("blast") of air therethrough in a manner intended to clear a blockage in the one or more outer lumens 2402 of the first tubing 2106. The valve 2126 may also be controllable to allow a controlled rate of airflow therethrough to facilitate determination of a volume of the wound space 2120.

The filter 2138 is configured to prevent contaminants from moving from the surrounding environment to the wound space 2120 via the valve 2126 and the one or more outer lumens 2402. The filter 2138 thereby protects the wound 2114 from infection or other complications. The filter 2138 restricts the rate of flow of air from the surrounding environment into the sealed space through the filter 2138 (e.g., by creating a pressure drop across the filter 2138 due to the filter media, contaminants trapped in the filter media, etc.) to a maximum of a restriction rate of the filter 2138. The restriction rate may be difficult to ascertain, may vary over time, or may be different in different instances of the filer 2138 (i.e., differing across multiple therapy units 108).

In the embodiments shown, the restriction rate of the filter is less than a typical rate of airflow through the valve 2126 when the valve 2126 is held in the open position for an extended amount of time (e.g., 500 milliseconds or greater). Accordingly, the difficulty in determining the restriction rate of the filter 2138 leads to a difficulty in determining a rate of airflow into the sealed space when the valve 2126 is held in the open position for an extended amount of time.

The control circuit 2132 is configured to control the operation of the therapy device 2108. For example, as described in detail below, the control circuit 2132 is configured to control the pneumatic pump 2112 to remove air from the sealed space to establish a negative pressure in the -sealed space, control the valve 2126 to provide a controlled leak to the sealed space, receive pressure measurements from the sensor 2122, determine a volume of the wound space 2120 based on the pressure measurements, and customized a wound therapy based on the volume of the wound space 2120. In some embodiments, the control circuit 2132 is also configured to detect a potential blockage of a lumen of the first tubing 2106, control the valve 2126 to the open position to allow a blast of air therethrough, keep the valve 2126 open while the blast of air clears the blockage, and control the valve 2126 to return to the closed position. These and other features of the control circuit 2132 are described in detail below.

Referring now to FIGS. 19-20, cross-sectional views of the valve 2126 are shown, according to exemplary embodiments. In the embodiments shown, the valve 2126 is a solenoid valve. FIG. 19 shows the valve 2126 in the closed position and FIG. 20 shows the valve in the open position. It should be understood that FIGS. 19-20 show one of many possible embodiments of the valve 2126.

The valve 2126 includes an inlet 2200 pneumatically communicable with the surrounding environment via the vent 2134, an outlet 2202 pneumatically communicable with the sealed space via channel 2136, a solenoid 2206, a plunger 2204 extending axially through the solenoid 2206 and substantially centered in the solenoid, a stopper 2205 coupled to the plunger 2204, and a spring 2208 coupled to the plunger 2204. The solenoid 2206 has a positive lead 2210 and a negative lead 2212 shown as operably coupled (e.g., conductively coupled) to the control circuit 2132.

The solenoid 2206 includes a coil of wire through which the plunger 2204 extends. When a current flows through the solenoid (e.g., when a voltage differential is applied across the solenoid 2206, a magnetic field is created in the solenoid 2206. The magnetic field is substantially aligned with a central axis of the solenoid. The plunger 2204 is made of a magnetic material, such that the magnetic field causes movement of the plunger 2204 when voltage is applied across the solenoid 2206.

As shown in FIG. 19, a voltage of approximately zero volts is applied across the solenoid 2206. That is, the control circuit 2132 prevents a voltage difference between the positive lead 2210 and the negative lead 2212. Accordingly, approximately zero current is created in the solenoid 2206, and approximately zero magnetic field is created by the solenoid 2206. The spring 2208 exerts a force on the plunger 2204 that holds the stopper 2205 adjacent the inlet 2200. The stopper 2205 prevents air from entering the valve 2206 via the inlet 2200. Airflow from the vent 2134 to the channel 2136 is thereby prevented (i.e., the valve 126 is in the closed position).

As shown in FIG. 20, a non-zero voltage is applied across the solenoid (e.g., approximately 5 volts). That is, the control circuit 2132 provides a control signal to the valve 2126 by creating a voltage differential between the positive lead 2210 and the negative lead 2212 of the solenoid 2206. It should be understood that, in various embodiments, various values of the non-zero voltage may be required to operate the valve 2126. When the control circuit 2132 provides a non-zero voltage to the valve 2126 (i.e., across the solenoid 2206), a magnetic field is created that causes the plunger 2204 to compress the spring 2208 and move the stopper 2205 away from the inlet 2200. Air may then flow from the vent 2134 through the valve 2126 to the sealed space (i.e., the valve 2126 is in the open position).

When the non-zero voltage is removed (i.e., when the voltage differential between the positive lead 2210 and the negative lead 2212 is brought to approximately zero), the magnetic field goes to zero and the spring 2208 forces the plunger 2204 and stopper 2205 back to the closed position shown in FIG. 19. Thus, the valve 2126 may be controlled to repeatedly alternate between the closed position shown in FIG. 19 and the open position shown in FIG. 20 by alternating between an approximately zero voltage and an approximately non-zero voltage. Example voltage patterns for controlling the valve 2126 to provide a controlled rate of airflow therethrough are described in detail below.

Referring now to FIG. 21, a cross-sectional view of the first tubing 2106 is shown, according to an exemplary embodiment. In the embodiment shown, the first tubing 2106 includes an inner lumen 2400 and four outer lumens 2402. That is, the first tubing 2106 is shown to include five separate lumens (e.g., channels, bores, pathways) through which air, fluid, and/or other debris may flow. Preferably, fluid and debris flows primarily through the inner lumen 2400, while air flows through the outer lumens 2402. At or near the canister 2104, the path of the outer lumens 2402 is separated from the path of the inner lumen 2400 as shown in FIG. 18. The inner lumen 2400 is connected to the inner volume of the canister to allow fluid and debris from the wound space 2120 to be collected in the canister. The outer lumens 2402 are connected to the sensor 2124 to facilitate the measurement and monitoring of pressure at the wound space.

The connection pad 2121 may include groves and other physical features configured to direct fluid and debris towards the inner lumen 2400 and away from the outer lumens 2402. However, fluid and debris may occasionally reach one or more of the outer lumens 2402 and cause a blockage of the one or more of the outer lumens 2402. A blockage of the inner lumen 2400 may also occur. As described below with reference to FIG. 22, the valve 2126 may be controlled to allow a blast of air to be released through the outer lumens 2402 to clear the fluid or other blockage from the outer lumens 2402, i.e., by pushing air and fluid back towards the dressing 2102 and out of the outer lumens 2402.

Figure 22:
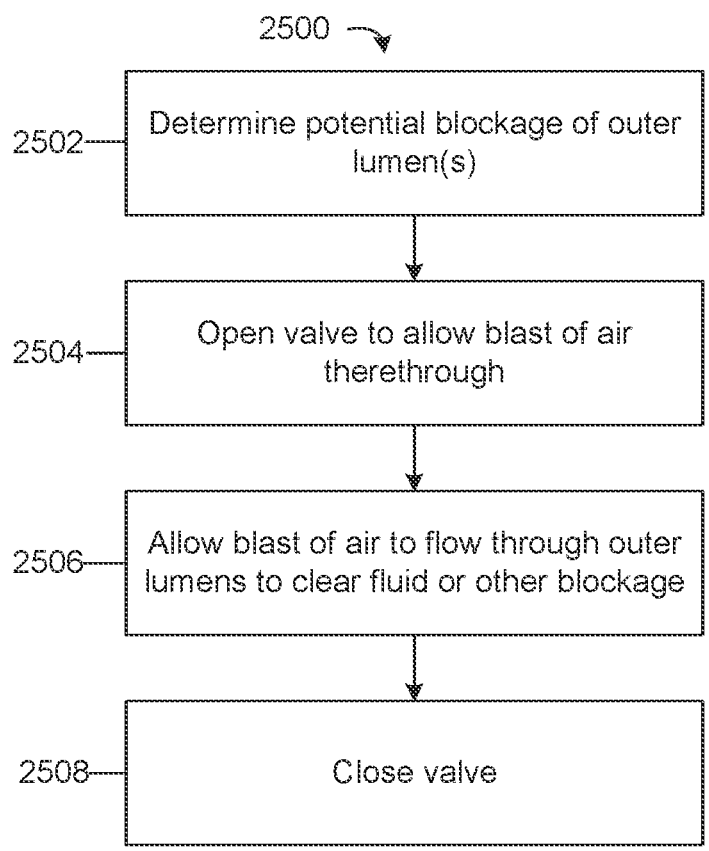
FIG. 22 is a flowchart of a process for managing blockages of the tubing of FIG. 21 using the solenoid valve of FIGS. 19-20, according to an exemplary embodiment.

Referring now to FIG. 22, a flowchart of a process 2500 for clearing blockages in the first tubing 2106 is shown, according to an exemplary embodiment. At step 2502, a potential blockage of one or more outer lumens 2402 is determined. As one example, the control circuit 2132 may detect a blockage based on pressure measurements from the sensor 2124. As another example, the control circuit 2132 assumes a potential blockage exists after a predetermined time period, i.e., such that steps 2504-2508 are triggered at a predetermined frequency.

At step 2504, the valve 2126 is opened to allow a blast of air therethrough. For example, the control circuit 2132 may provide a non-zero voltage to the solenoid 2206 of the valve 2126. The control circuit 2132 may cause the valve 2126 to be held in the open position for an extended time period, i.e., longer than the periods shown in FIG. 22 and discussed with reference thereto below. For example, in one embodiment the non-zero voltage is provided for approximately 500 milliseconds to hold the valve 126 open for approximately 500 milliseconds. When the valve 2126 is held open, a blast of air may flow therethrough at a high airflow rate due to the pressure differential between the surrounding environment (ambient air) and the sealed space. This blast of air may flow into a blocked outer lumen 2402 and push any blockage out of the first tubing 2106 towards the dressing 2106. Blockages in the outer lumens 2402 may thereby be periodically cleared to allow free airflow through the outer lumens 2402, for example to ensure that the measurements of the pressure sensor 2124 accurately represent the pressure at the wound space 2120.

At step 2506, the solenoid valve 2508 is closed. For example, the control circuit 2132 causes approximately zero voltage to be provided across the solenoid 2206. Airflow from the environment to the sealed space is prevented. The pneumatic pump 2122 may be operated to reestablish a desired negative pressure at the wound space 2120.

Figure 23:
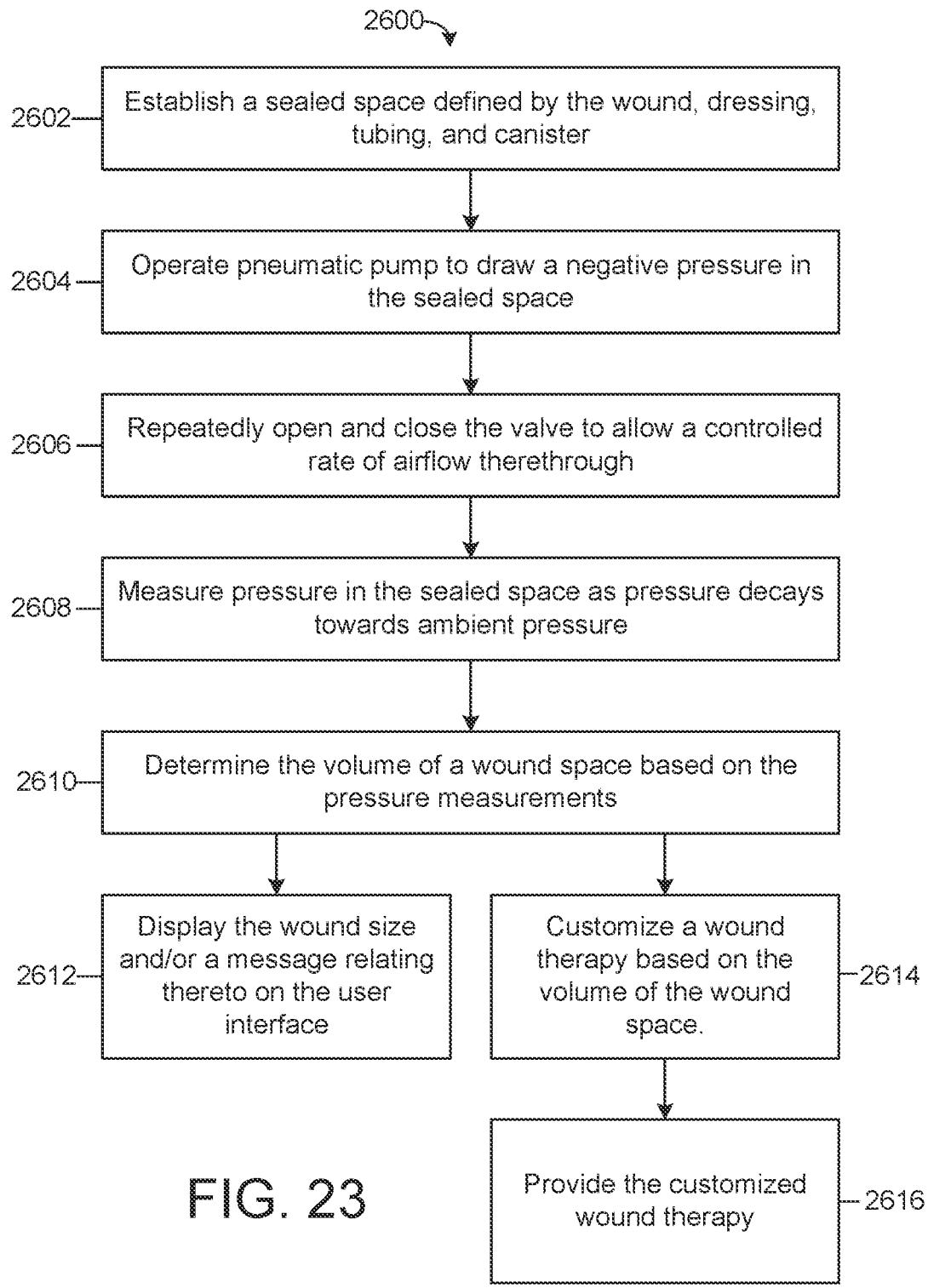
FIG. 23 is a flowchart of a process for volume determination by the NPIWT system of FIG. 18, according to an exemplary embodiment.

Referring now to FIG. 23, a flowchart of a process 2600 for wound volume determination and wound therapy customization is shown, according to an exemplary embodiment. The process 2600 may be carried out by the NPIWT system 100 of FIG. 18.

At step 2602, a sealed space defined by the wound 2114, the dressing 2102, the first tubing 2106, and the canister 2104 is established. The sealed space includes the wound space 2120. In other words, the dressing 2102 is applied to the wound 2114 with the drape 2116 sealed over the wound 2114 and the foam layer 2118 (or other layers included in the dressing 2102 in various embodiments) to define the wound space 2120. The first tubing 2106 is coupled to the drape 2116 in fluid communication with the wound space 2120 via the connection pad 2121. The first tubing 2106 is also coupled to the canister 2104 in fluid communication with the canister 2104.

At step 2604, the pneumatic pump 2122 is operated to draw a negative pressure in the sealed space. That is, the control circuit 2132 provides a control signal to the pneumatic pump 2122 that causes the pneumatic pump to remove air from the sealed space. The control circuit 2132 may receive pressure measurements from pressure sensor 2124 and cause the pneumatic pump 2122 to cease operation when a desired negative pressure is achieved (e.g., −125 mmHg) and/or otherwise control the pneumatic pump 2122 based on the pressure measurements to provide a desired negative pressure or pattern of desired negative pressures.

At step 2606, the valve 2126 is repeatedly opened and closed (e.g., "cycled") to allow a controlled rate of airflow therethrough. The control circuit 2132 may provide a control signal to the valve 2126 that causes the valve 2126 to repeatedly open and close. For example, in an embodiment where the valve 2126 is a solenoid valve, for example as shown in FIGS. 19-20, at step 2606 the control circuit 2132 provides a voltage pattern to the valve 2126. That is, the control circuit 2132 may repeatedly alternate a voltage differential across between the positive lead 2210 and the negative lead 2212 between approximately zero volts and a non-zero voltage (e.g., approximately five volts). For example, the voltage pattern may include a step function that repeatedly steps between approximately zero voltage and the non-zero voltage.

Figure 24:
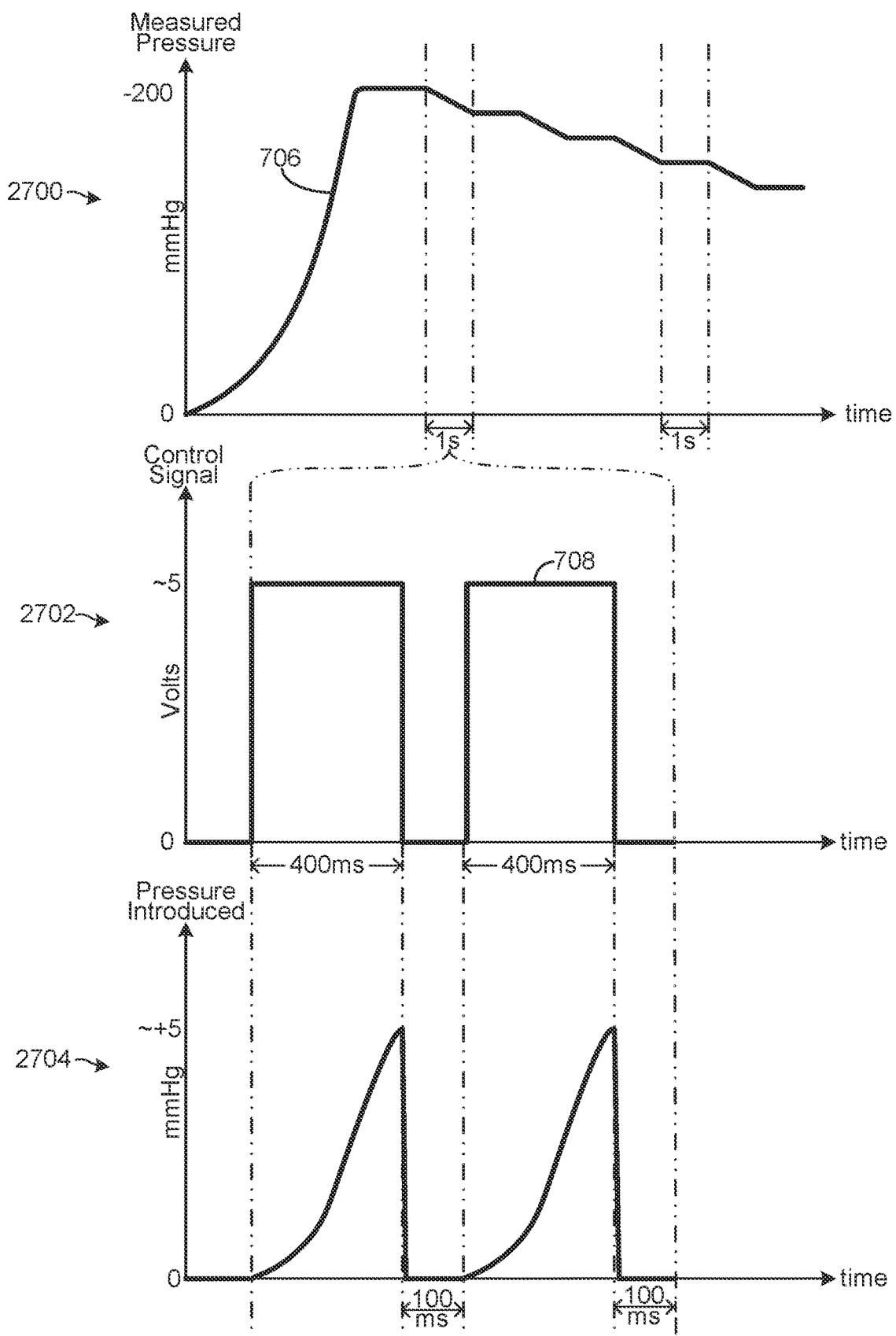
FIG. 24 is a collection of graphs illustrating various aspects of the process of FIG. 23, according to an exemplary embodiment.
Figure 25:
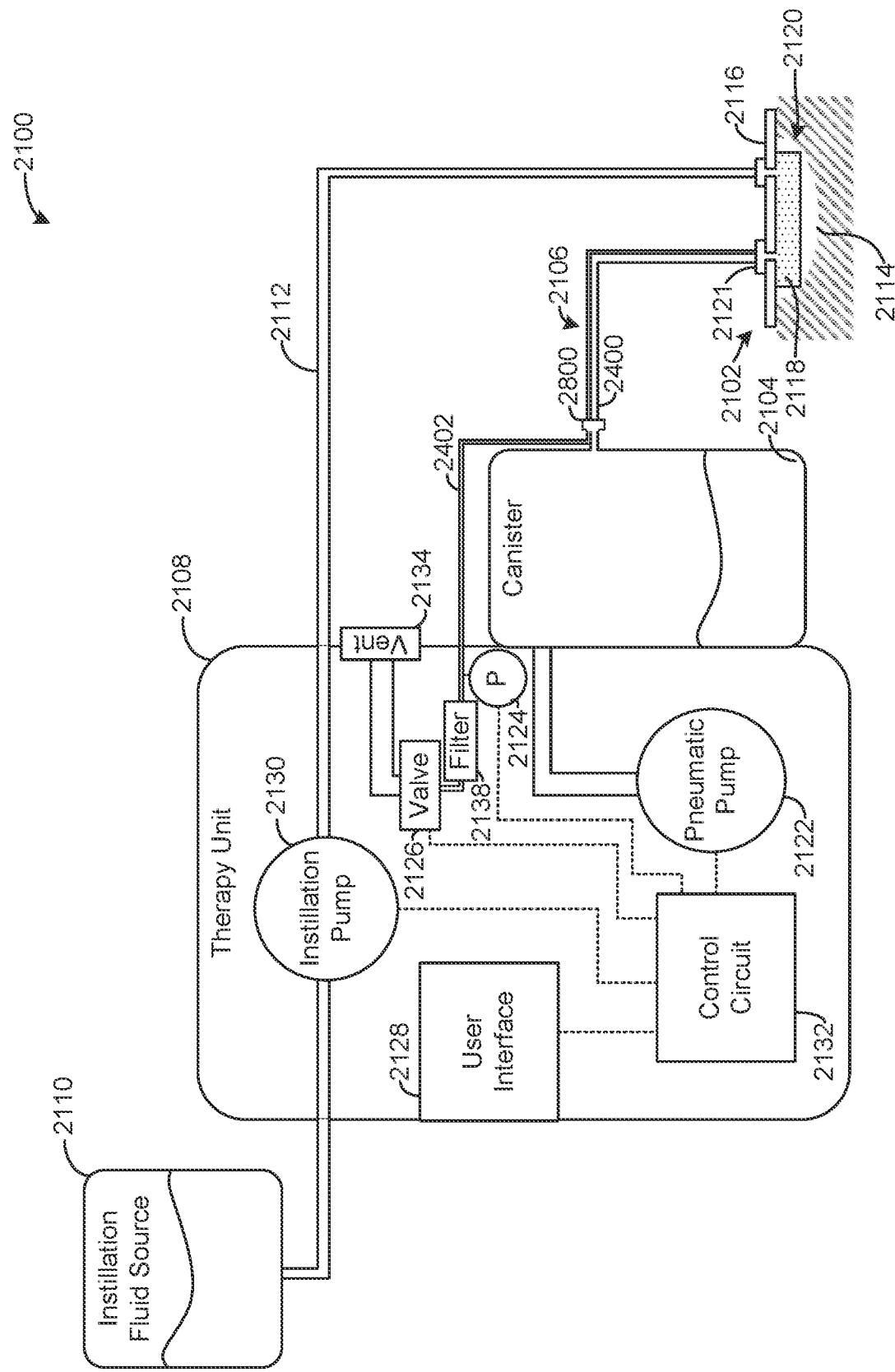
FIG. 25 is a block diagram of the NPIWT system of FIG. 18 with a removable cap, according to an exemplary embodiment.

In one example, as shown in FIG. 24 and described in detail with reference thereto, the voltage pattern may include a repeating pattern of approximately 400 milliseconds at the non-zero voltage, approximately 100 milliseconds at approximately zero voltage, approximately 400 milliseconds at the non-zero voltage, and approximately 100 milliseconds at approximately zero voltage. The voltage pattern may thereby cause the valve 2126 to alternate between the open position and the closed position with a period of approximately 500 milliseconds. In some embodiments, the voltage pattern may include a first set of two repetitions of the repeating pattern, followed by approximately one second at approximately zero voltage, followed by a second set of two repetitions of the repeating pattern. In preferred embodiments, the non-zero voltage is provided, in each repetition, for no more than a maximum continuous duration of approximately 500 milliseconds.

By controlling the valve 2126 to repeatedly alternate between the open position and the closed position, a controlled rate of airflow is allowed therethrough across the repetitions. That is, a lower rate of airflow is allow through the valve 2126 as compared to holding the valve 2126 open for an extended or indefinite amount of time (e.g., as described for process 500), for example 500 milliseconds or longer. The controlled rate may be customized by altering the voltage pattern. Additionally, the controlled rate may be known based on the voltage pattern. For example, the controlled rate may be predetermined by bench testing for each of one or more voltage patterns. In preferred embodiments, the controlled rate is less than a restriction rate of the filter 2138.

At step 608, the pressure in the sealed space is measured as the negative pressure in the sealed space decays towards ambient pressure (i.e., approaches approximately atmospheric pressure). The controlled airflow through the valve 2126 allows air to enter the sealed space and causes the pressure in the sealed space to decay towards ambient pressure. The sensor 2124 may measure the pressure in the sealed space and provide the pressure measurements to the control circuit 2132. The control circuit 2132 may record (store, save) the pressure measurements. In some embodiments, the control circuit 2132 may collect the pressure measurements to form a pressure decay curve.

At step 610, the volume of the wound space 2120 is determined based on the pressure measurements. For example, based on the known controlled rate of airflow through the valve 2126 and the measured pressure decay curve, the volume of the sealed space may be determined. The volume of the wound space may then be determined by removing a volume of the canister and tube from the total volume of the sealed space. In some cases, one or more additional valves, sensors, etc. are included to facilitate generation and collection of data for use in wound size determination. Various methods for calculating wound size are possible in various embodiments, for example as described with reference to FIGS. 1-17.

At step 2612, the wound size (e.g., the volume of the wound space 2120) and/or a message relating thereto is displayed on the user interface 2128. For example, the control circuit 2130 may cause a graphical user interface that includes the wound size to be displayed on a screen of the user interface 2128. As another example, the control circuit 2130 may determine one or more warnings, progress reports, or other wound-related message based on the wound size and control the user interface 2128 to display the warning, report, or other message. For example, the user interface 2128 may display a graphical representation of change in the volume of the wound space over time.

At step 2614, a wound therapy is customized based on the volume of the wound space. In some embodiments, the control circuit 2130 automatically customizes a wound therapy based on the determined volume of the wound space 2120. In other embodiments, a user is facilitated in customizing a wound therapy based on the volume of the wound space 2120 based on information displayed on the user interface 2128.

In the example shown, the control circuit 2130 automatically customizes instillation by automatically determining an amount of instillation fluid to be supplied to the wound space 2120 based on the determined volume of the wound space 2120. For example, the control circuit 2130 may multiple the determined volume of the wound space 2120 by a scaling factor to determine the amount of instillation fluid to be supplied to the wound space 2120. As another example, the control circuit 2130 may determine the amount of instillation to be supplied as equal to the volume of the wound space 2120. Various calculations are possible for various applications, wound types, instillation fluid types, patient and/or caregiver preferences, etc.

At step 2616, the customized wound therapy is provided. For example, the control circuit 2130 may control the instillation pump 2130 to provide the determined amount of instillation fluid from the instillation fluid source 2110 to the wound space 2120. Instillation therapy may thereby be tailored to meet the needs of the healing wound in real time. Various other customized therapies are possible in various embodiments.

Referring now to FIG. 24, a collection of graphs illustrating the operation of the NPIWT system 2100 is shown, according to an exemplary embodiment. FIG. 24 shows a measured pressure graph 2700, a control signal graph 2702, and an introduced pressure graph 2704. The pressure graph 2700 illustrates a change in pressure in the sealed space over time as measured by the pressure sensor 2124. As illustrated by the pressure graph 2700, a measured pressure line 2706 approaches a desired negative pressure (shown as −200 mmHg) as the pneumatic pump 2122 is operated to draw air out of the sealed space. The measured pressure then decays as the valve 2126 is controlled to allow a controlled rate of airflow therethrough.

The control signal graph 2702 illustrates a voltage pattern applied to the valve 2126 (i.e., across the solenoid 2206). As shown, a control signal 2708 alternates between approximately zero voltage and a non-zero voltage, shown as approximately five volts. As shown, the control signal includes approximately 400 milliseconds at the non-zero voltage, approximately 100 milliseconds at approximately zero voltage, another approximately 400 milliseconds at the non-zero voltage, and another approximately 100 milliseconds at approximately zero voltage. After these two repetitions (i.e., after two periods of 500 milliseconds), the control signal may include one second at approximately zero voltage as illustrated in FIG. 24. It should be understood that various other frequencies and periods for a voltage pattern may be used in various embodiments. As one possible additional example, in an alternative embodiment the voltage pattern alternates between approximately 200 milliseconds at a non-zero voltage and 50 milliseconds at approximately zero voltage for three or more repetitions (e.g., four repetitions), followed by approximately one second at approximately zero voltage before repeating the voltage pattern. In various embodiments, the non-zero voltage is repeatedly provided for a duration between a minimum continuous duration of approximately 50 milliseconds and a maximum continuous duration of approximately 500 milliseconds, with alternating periods of approximately zero voltage.

The introduced pressure graph 2704 illustrates the amount of pressure let into the sealed space over time. In the example shown, approximately 5 mmHg is introduced into the sealed space for each 400 millisecond segment of non-zero voltage in the control signal 708. The introduced pressure graph 2704 illustrates that the pressure decay in the sealed space may be managed by the alternating pattern of the valve 2126 (i.e., of the control signal 2708). For example, the introduced pressure graph 2704 indicates that a lag time may exist between the beginning of a non-zero voltage period and a point in time corresponding to peak rate of pressure reduction or peak rate of airflow through the valve 2126.

Referring now to FIG. 8, the NPIWT system 2100 of FIG. 18 is shown in an alternative embodiment. In the embodiment shown, the volume of the sealed space and/or the wound space can be determined by first determining the restriction rate of the filter 2138 (i.e., the rate of airflow through the filter 2138) as part of a calibration process before therapy is started. As shown in FIG. 18, a removable cap (structure, cover, joint) 2800 is placed proximate a point wherein the inner lumen 2400 and the outer lumens 2402 come together to form the first tubing 2106 (e.g., at a port of the canister 2104). For example, the first tubing 2106 may be disconnected at this point and replaced by the removable cap 2800 as shown in FIG. 8. The removable cap 2800 connects the inner lumen 2400 and the outer lumens 2402 and causes air to flow directly therebetween (i.e., without passing through the dressing 2102) during a process for determining the restriction rate of the filter 2138. The removable cap 2800 may then be removed and the first tubing 2106 connected in the configuration described above.

To determine the restriction rate of the filter 2138 while the removable cap 2800 is applied as in FIG. 8, the valve 2126 is closed and the pneumatic pump 2122 is run to remove air from the canister 2104. The valve 2126 may then be opened for an indefinite amount of time to allow air to flow back into the canister 2104 while the pressure sensor 2124 measures the change in pressure over time. Based on a known volume of the canister 2104 and the change in pressure over time while the valve 2126 is open, the control circuit 2132 may calculate the rate of airflow through the filter. The cap 2800 facilitates this process by ensuring that the unknown volume of the wound space does not influence the rate of change of the pressure during such a process.

Configuration of Exemplary Embodiments

As utilized herein, the terms "approximately," "about," "substantially", and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the disclosure as recited in the appended claims.

It should be noted that the term "exemplary" and variations thereof, as used herein to describe various embodiments, are intended to indicate that such embodiments are possible examples, representations, or illustrations of possible embodiments (and such terms are not intended to connote that such embodiments are necessarily extraordinary or superlative examples).

The term "coupled" and variations thereof, as used herein, means the joining of two members directly or indirectly to one another. Such joining may be stationary (e.g., permanent or fixed) or moveable (e.g., removable or releasable). Such joining may be achieved with the two members coupled directly to each other, with the two members coupled to each other using a separate intervening member and any additional intermediate members coupled with one another, or with the two members coupled to each other using an intervening member that is integrally formed as a single unitary body with one of the two members. If "coupled" or variations thereof are modified by an additional term (e.g., directly coupled), the generic definition of "coupled" provided above is modified by the plain language meaning of the additional term (e.g., "directly coupled" means the joining of two members without any separate intervening member), resulting in a narrower definition than the generic definition of "coupled" provided above. Such coupling may be mechanical, electrical, or fluidic.

References herein to the positions of elements (e.g., "top," "bottom," "above," "below") are merely used to describe the orientation of various elements in the FIGURES. It should be noted that the orientation of various elements may differ according to other exemplary embodiments, and that such variations are intended to be encompassed by the present disclosure. Although the figures show a specific order of method steps, the order of the steps may differ from what is depicted. Also two or more steps can be performed concurrently or with partial concurrence. Such variation will depend on the software and hardware systems chosen and on designer choice. All such variations are within the scope of the disclosure. Likewise, software implementations could be accomplished with standard programming techniques with rule based logic and other logic to accomplish the various connection steps, calculation steps, processing steps, comparison steps, and decision steps.

The construction and arrangement of the systems and methods as shown in the various exemplary embodiments are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.). For example, the position of elements can be reversed or otherwise varied and the nature or number of discrete elements or positions can be altered or varied. Accordingly, all such modifications are intended to be included within the scope of the present disclosure. The order or sequence of any process or method steps can be varied or re-sequenced according to alternative embodiments. Other substitutions, modifications, changes, and omissions can be made in the design, operating conditions and arrangement of the exemplary embodiments without departing from the scope of the present disclosure.

As used herein, the term "circuit" may include hardware structured to execute the functions described herein. In some embodiments, each respective "circuit" may include machine-readable media for configuring the hardware to execute the functions described herein. The circuit may be embodied as one or more circuitry components including, but not limited to, processing circuitry, network interfaces, peripheral devices, input devices, output devices, sensors, etc. In some embodiments, a circuit may take the form of one or more analog circuits, electronic circuits (e.g., integrated circuits (IC), discrete circuits, system on a chip (SOCs) circuits, etc.), telecommunication circuits, hybrid circuits, and any other type of "circuit." In this regard, the "circuit" may include any type of component for accomplishing or facilitating achievement of the operations described herein. For example, a circuit as described herein may include one or more transistors, logic gates (e.g., NAND, AND, NOR, OR, XOR, NOT, XNOR, etc.), resistors, multiplexers, registers, capacitors, inductors, diodes, wiring, and so on).

The "circuit" may also include one or more processors communicably coupled to one or more memory or memory devices. In this regard, the one or more processors may execute instructions stored in the memory or may execute instructions otherwise accessible to the one or more processors. In some embodiments, the one or more processors may be embodied in various ways. The one or more processors may be constructed in a manner sufficient to perform at least the operations described herein. In some embodiments, the one or more processors may be shared by multiple circuits (e.g., circuit A and circuit B may comprise or otherwise share the same processor which, in some example embodiments, may execute instructions stored, or otherwise accessed, via different areas of memory). Alternatively or additionally, the one or more processors may be structured to perform or otherwise execute certain operations independent of one or more co-processors. In other example embodiments, two or more processors may be coupled via a bus to enable independent, parallel, pipelined, or multi-threaded instruction execution. Each processor may be implemented as one or more general-purpose processors, application specific integrated circuits (ASICs), field programmable gate arrays (FPGAs), digital signal processors (DSPs), or other suitable electronic data processing components structured to execute instructions provided by memory. The one or more processors may take the form of a single core processor, multi-core processor (e.g., a dual core processor, triple core processor, quad core processor, etc.), microprocessor, etc. In some embodiments, the one or more processors may be external to the apparatus, for example the one or more processors may be a remote processor (e.g., a cloud based processor). Alternatively or additionally, the one or more processors may be internal and/or local to the apparatus. In this regard, a given circuit or components thereof may be disposed locally (e.g., as part of a local server, a local computing system, etc.) or remotely (e.g., as part of a remote server such as a cloud based server). To that end, a "circuit" as described herein may include components that are distributed across one or more locations. The present disclosure contemplates methods, systems and program products on any machine-readable media for accomplishing various operations. The embodiments of the present disclosure can be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, CD-ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. Combinations of the above are also included within the scope of machine-readable media. Machine-executable instructions include, for example, instructions and data which cause a general purpose computer, special purpose computer, or special purpose processing machines to perform a certain function or group of functions.

What is claimed is:

1. A control circuit for a negative pressure therapy system, the control circuit communicatively coupled to a pump that is fluidly communicable with a sealed space, a sensor fluidly coupled to the sealed space, and a valve fluidly coupled between a sealed space and a surrounding environment, the control circuit configured to:
   actuate the pump to draw fluid from the sealed space,
   repeatedly actuate the valve between an open position and a closed position, allowing a controlled rate of airflow through the valve;
   receive measurements of a pressure in the sealed space generated by the sensor during a pressure decay in response to the controlled rate of airflow through the valve; and
   in response to the measurements of the pressure and the controlled rate of airflow, determine a volume of the sealed space.

2. The control circuit of claim 1, wherein the controlled rate of airflow is less than a restriction rate of a filter fluidly coupled between the valve and a canister.

3. The control circuit of claim 1, wherein the valve comprises a solenoid valve and the control circuit is further configured to actuate the valve by providing a voltage pattern to the solenoid valve.

4. The control circuit of claim 3, wherein the voltage pattern comprises a step function between a zero voltage and a non-zero voltage.

5. The control circuit of claim 4, wherein the voltage pattern remains at the non-zero voltage for no more than a maximum continuous duration of 500 milliseconds.

6. The control circuit of claim 5, wherein voltage pattern comprises a repeating pattern of 400 milliseconds at a non-zero voltage, 100 milliseconds at zero voltage, 400 milliseconds at the non-zero voltage, and 100 milliseconds at zero voltage.

7. The control circuit of claim 6, wherein the voltage pattern comprises a first set of two periods of the repeating pattern, one second at zero voltage, and a second set of two periods of the repeating pattern.

8. The control circuit of claim 3, wherein the voltage pattern causes the solenoid valve to alternate between the open position and the closed position with a period of 500 milliseconds.

9. The control circuit of claim 1, wherein the control circuit is further configured to determine a customized wound therapy based on the volume of the sealed space and to provide the customized wound therapy.

10. The control circuit of claim 9, wherein the customized wound therapy comprises instillation therapy.

11. The control circuit of claim 10, wherein the control circuit is configured to customize the instillation therapy by determining an amount of instillation fluid to supply to the sealed space based on the volume of the sealed space.

12. The control circuit of claim 11, wherein the control circuit is further configured to actuate an instillation pump to provide the amount of the instillation fluid to the sealed space.

\* \* \* \* \*